(12) United States Patent
Besemer et al.

(10) Patent No.: US 7,364,895 B2
(45) Date of Patent: Apr. 29, 2008

(54) BIOARRAY CHIP REACTION APPARATUS AND ITS MANUFACTURE

(75) Inventors: Donald M. Besemer, Los Altos Hills, CA (US); Virginia W. Goss, Santa Barbara, CA (US); James L. Winkler, Sunnyvale, CA (US)

(73) Assignee: Affymetrix, Inc., Santa Clara, CA (US)

( * ) Notice: Subject to any disclaimer, the term of this patent is extended or adjusted under 35 U.S.C. 154(b) by 570 days.

(21) Appl. No.: 10/639,696

(22) Filed: Aug. 11, 2003

(65) Prior Publication Data

US 2005/0191630 A1    Sep. 1, 2005

Related U.S. Application Data

(63) Continuation of application No. 10/229,759, filed on Aug. 28, 2002, now Pat. No. 6,733,977, which is a continuation of application No. 10/046,623, filed on Jan. 14, 2002, now Pat. No. 6,551,817, which is a continuation of application No. 09/907,196, filed on Jul. 17, 2001, now Pat. No. 6,399,365, which is a continuation of application No. 09/302,052, filed on Apr. 29, 1999, now Pat. No. 6,287,850, which is a continuation of application No. 08/485,452, filed on Jun. 7, 1995, now Pat. No. 5,945,334, which is a continuation-in-part of application No. 08/255,682, filed on Jun. 8, 1994, now abandoned.

(51) Int. Cl.
*A61L 9/01* (2006.01)
*C12M 1/34* (2006.01)
*B01F 11/00* (2006.01)
*B01F 15/02* (2006.01)
*B01L 3/00* (2006.01)

(52) U.S. Cl. .................. 435/266; 435/288.3; 366/261; 366/183.3; 422/102

(58) Field of Classification Search ............ 435/286.7, 435/288.3; 366/261, 183.3; 422/102
See application file for complete search history.

(56) References Cited

U.S. PATENT DOCUMENTS

| | | | |
|---|---|---|---|
| 3,281,860 A | 10/1966 | Adams et al. | |
| 3,690,836 A | 9/1972 | Buissiere et al. | ............ 23/253 |
| 3,710,933 A | 1/1973 | Fulwlyer et al. | |
| 3,802,966 A | 4/1974 | Delekto et al. | |
| 4,016,855 A | 4/1977 | Mimata | |
| 4,121,222 A | 10/1978 | Diebold et al. | |
| 4,125,828 A | 11/1978 | Resnick et al. | ............ 382/134 |
| 4,204,929 A | 5/1980 | Bier | |
| 4,373,071 A | 2/1983 | Itakura | |
| 4,458,066 A | 7/1984 | Caruthers et al. | |
| 4,500,707 A | 2/1985 | Caruthers et al. | |
| 4,728,502 A | 3/1988 | Hamill | |
| 4,731,325 A | 3/1988 | Palva et al. | |
| 4,753,775 A | 6/1988 | Ebersole et al. | ............ 422/81 |
| 4,780,504 A | 10/1988 | Buendia et al. | |
| 4,812,512 A | 3/1989 | Buendia et al. | |
| 4,815,274 A | 3/1989 | Piatti | |
| 4,845,552 A | 7/1989 | Jaggi et al. | ............ 382/128 |
| 4,853,335 A | 8/1989 | Olsen et al. | |
| 4,877,745 A | 10/1989 | Hayes et al. | |
| 4,878,971 A | 11/1989 | Tsunekawa et al. | |
| 4,912,035 A | 3/1990 | Belly et al. | |
| 4,963,498 A | 10/1990 | Hillman et al. | |
| 4,992,383 A | 2/1991 | Farnsworth | |
| 5,021,550 A | 6/1991 | Zeiger | |
| 5,047,524 A | 9/1991 | Andrus et al. | |
| 5,091,652 A | 2/1992 | Mathies et al. | ............ 250/458.1 |
| 5,141,813 A | 8/1992 | Nelson | |
| 5,143,854 A | 9/1992 | Pirrung et al. | |
| 5,153,319 A | 10/1992 | Caruthers et al. | |
| 5,188,963 A | 2/1993 | Stapleton | |
| 5,196,305 A | 3/1993 | Findlay et al. | |
| 5,200,051 A | 4/1993 | Cozzette et al. | |
| 5,204,253 A | 4/1993 | Sanford | |
| 5,256,549 A | 10/1993 | Urdea | |
| 5,281,516 A | 1/1994 | Stapleton et al. | |
| 5,281,540 A | 1/1994 | Merkh et al. | ............ 436/530 |

(Continued)

FOREIGN PATENT DOCUMENTS

EP    0 378 968    12/1989

(Continued)

OTHER PUBLICATIONS

Blaheta, et al., A rapid non-radioactive fluorescence assay for the measurement of both cell number and proliferation, Journal of Immunological Methods, May 21, 1991.

(Continued)

*Primary Examiner*—Kenneth R. Horlick
*Assistant Examiner*—Joyce Tung
(74) *Attorney, Agent, or Firm*—Wei Zhou; Lisa T. Kajisa; Philip L. McGarrigle

(57) ABSTRACT

A body 300 having a cavity 310 for mounting a substrate 120 fabricated with probe sequences at known locations according to the methods disclosed in U.S. Pat. No. 5,143,854 and PCT WO 92/10092 or others, is provided. The cavity includes inlets 350 and 360 for introducing selected fluids into the cavity to contact the probes. Accordingly, a commercially feasible device for use in high throughput assay systems is provided.

28 Claims, 46 Drawing Sheets

U.S. PATENT DOCUMENTS

| | | |
|---|---|---|
| 5,287,272 A | 2/1994 | Rutenberg et al. ..... 364/413.01 |
| 5,288,514 A | 2/1994 | Ellman |
| 5,300,779 A | 4/1994 | Hillman et al. |
| 5,304,487 A | 4/1994 | Wilding et al. |
| 5,310,469 A | 5/1994 | Cunningham et al. |
| 5,314,829 A | 5/1994 | Coles ......................... 436/165 |
| 5,320,808 A | 6/1994 | Holen et al. |
| 5,322,799 A | 6/1994 | Miller ........................ 436/165 |
| 5,346,672 A | 9/1994 | Stapleton et al. |
| 5,348,855 A | 9/1994 | Dattagupta et al. |
| 5,358,691 A | 10/1994 | Clark et al. |
| 5,374,395 A | 12/1994 | Robinson et al. ............. 422/64 |
| 5,382,511 A | 1/1995 | Stapleton |
| 5,382,512 A | 1/1995 | Smethers et al. |
| 5,384,261 A | 1/1995 | Winkler et al. |
| 5,436,129 A | 7/1995 | Stapleton |
| 5,443,985 A | 8/1995 | Lu et al. |
| 5,451,500 A | 9/1995 | Stapleton |
| 5,466,575 A | 11/1995 | Cozzette et al. |
| 5,474,796 A | 12/1995 | Brennan |
| 5,486,335 A | 1/1996 | Wilding et al. |
| 5,486,452 A | 1/1996 | Gordon et al. |
| 5,494,124 A | 2/1996 | Dove et al. |
| 5,498,392 A | 3/1996 | Wilding et al. |
| 5,545,531 A | 8/1996 | Rava et al. |
| 5,571,639 A | 11/1996 | Hubbell et al. |
| 5,578,832 A | 11/1996 | Trulson et al. ............ 250/458.1 |
| 5,589,136 A | 12/1996 | Northrup et al. ........... 422/102 |
| 5,605,653 A | 2/1997 | DeVos |
| 5,631,734 A | 5/1997 | Stern et al. .................. 356/317 |
| 5,637,469 A | 6/1997 | Wilding et al. |
| 5,639,423 A | 6/1997 | Northrup et al. |
| 5,639,612 A | 6/1997 | Mitsuhashi et al. ............. 435/6 |
| 5,677,195 A | 10/1997 | Winkler et al. |
| 5,698,393 A | 12/1997 | Macioszek et al. |
| 5,700,637 A | 12/1997 | Southern |
| 5,757,666 A | 5/1998 | Schreiber et al. ........... 364/509 |
| 5,800,992 A | 9/1998 | Fodor et al. |
| 5,807,522 A | 9/1998 | Brown et al. |
| 5,834,758 A | 11/1998 | Trulson et al. |
| 5,846,708 A | 12/1998 | Hollis et al. |
| 5,851,488 A | 12/1998 | Saul et al. ..................... 422/67 |
| 5,856,174 A | 1/1999 | Lipshutz et al. |
| 5,874,219 A | 2/1999 | Rava et al. |
| 5,910,288 A | 6/1999 | Schembri ..................... 422/102 |
| 5,922,591 A | 7/1999 | Anderson et al. |
| 5,925,517 A | 7/1999 | Tyagi et al. |
| 5,945,334 A | 8/1999 | Besemer et al. .......... 435/287.2 |
| 5,961,923 A | 10/1999 | Nova et al. .................. 422/68.1 |
| 6,096,561 A | 8/2000 | Tayi ............................ 436/518 |
| 6,103,463 A | 8/2000 | Chetverin et al. |
| 6,114,122 A | 9/2000 | Besemer et al. |
| 6,121,048 A | 9/2000 | Zaffaroni et al. |
| 6,140,044 A | 10/2000 | Besemer et al. ................ 435/6 |
| 6,180,351 B1 | 1/2001 | Cattell ............................ 435/6 |
| 6,186,659 B1 | 2/2001 | Schembri ..................... 366/262 |
| 6,215,894 B1 | 4/2001 | Zeleny ........................ 382/133 |
| 6,238,910 B1 | 5/2001 | Custance et al. ......... 435/287.2 |
| 6,258,593 B1 | 7/2001 | Schembri et al. ........ 435/287.2 |
| 6,270,961 B1 | 8/2001 | Drmanac |
| 6,287,850 B1 | 9/2001 | Besemer et al. ......... 435/287.2 |
| 6,322,971 B1 | 11/2001 | Chetverin et al. |
| 6,355,431 B1 | 3/2002 | Chee et al. |
| 6,355,432 B1 | 3/2002 | Fodor et al. |
| 6,391,623 B1 | 5/2002 | Besemer et al. |
| 6,396,995 B1 | 5/2002 | Stuelpnagel et al. |
| 6,399,365 B2 | 6/2002 | Besemer et al. ......... 435/287.2 |
| 6,420,114 B1 | 7/2002 | Bedilion et al. ................ 435/6 |
| 6,429,027 B1 | 8/2002 | Chee et al. |
| 6,432,696 B2 | 8/2002 | Custance et al. ......... 435/287.2 |
| 6,513,968 B2 | 2/2003 | Schembri ..................... 366/341 |
| 6,544,732 B1 | 4/2003 | Chee et al. |
| 6,551,817 B2 | 4/2003 | Besemer et al. |
| 6,613,529 B2 | 9/2003 | Bedilion et al. |
| 6,620,584 B1 | 9/2003 | Chee et al. |
| 6,648,853 B1 | 11/2003 | McEntee |
| 6,663,832 B2 | 12/2003 | Lebl et al. |
| 6,682,702 B2 | 1/2004 | Barth et al. |
| 6,720,149 B1 | 4/2004 | Rava et al. |
| 6,733,977 B2 | 5/2004 | Besemer et al. |
| 6,835,938 B2 | 12/2004 | Ghosh et al. |
| 6,905,816 B2 | 6/2005 | Jacobs et al. |
| 2002/0095073 A1 | 7/2002 | Jacobs et al. |
| 2002/0132221 A1 | 9/2002 | Chee et al. |
| 2002/0132241 A1 | 9/2002 | Fan et al. |
| 2002/0150909 A1 | 10/2002 | Stuelkpnagel et al. |
| 2002/0177141 A1 | 11/2002 | Chee et al. |
| 2002/0177159 A1 | 11/2002 | Bedilion et al. |
| 2003/0032204 A1 | 2/2003 | Walt et al. |
| 2003/0096239 A1 | 5/2003 | Gunderson et al. |
| 2003/0108867 A1 | 6/2003 | Chee et al. |
| 2003/0108900 A1 | 6/2003 | Oliphant et al. |
| 2003/0113724 A1 | 6/2003 | Schembri et al. |
| 2003/0124029 A1 | 7/2003 | Webb et al. |
| 2003/0203492 A1 | 10/2003 | Sillman |
| 2003/0232379 A1 | 12/2003 | Amorese et al. |
| 2003/0235520 A1 | 12/2003 | Shea et al. |
| 2004/0096914 A1 | 5/2004 | Fang et al. |
| 2004/0208800 A1 | 10/2004 | Barth et al. |
| 2005/0026299 A1 | 2/2005 | Bhattacharjee et al. |

FOREIGN PATENT DOCUMENTS

| | | |
|---|---|---|
| EP | 0 417 305 | 9/1990 |
| EP | 0 583 078 A | 2/1994 |
| EP | 0 695 941 A | 2/1996 |
| EP | 0 260 965 | 3/1998 |
| EP | 0675966 | 10/2004 |
| WO | WO 89/10977 | 11/1989 |
| WO | WO 90/00626 | 1/1990 |
| WO | WO 90/03382 | 4/1990 |
| WO | WO 90/15070 | 12/1990 |
| WO | WO 92/10092 | 6/1992 |
| WO | WO 92/10587 | 6/1992 |
| WO | WO 92/10588 | 6/1992 |
| WO | WO 93/09668 | 5/1993 |
| WO | WO 93/11262 | 6/1993 |
| WO | 93/17126 | 9/1993 |
| WO | WO 93/22053 | 11/1993 |
| WO | WO 93/22058 | 11/1993 |
| WO | 95/09248 | 4/1995 |
| WO | 95/33846 | 12/1995 |
| WO | 01/43874 | 6/2001 |
| WO | WO 02/00336 | 1/2002 |

OTHER PUBLICATIONS

Manns, et al., Microplate History 2nd Edition, May 1999, presented at MipTec-ICAR'99, Montreux, Switzerland.

Manns, Roy L. Necessity is the Mother of Invention—the History of Microplates, Business Briefing: Future Drug Discovery, 2003.

New Falcon (R) Cell Culture Inserts Fit 24 Well Plates, News Release, Apr. 2, 1991, p. 1.

Drmanac, "Genome Sequencing Machine," Integral Genetics Group, Center for Mechanistic Biology and Biotechnology, Argonne National Laboratory, Argonne, IL 60439, p. 60, May 11-May 15, 1994.

Drmanac et al., *Towards Genome DNA Sequencing Chip Based on Oligonucleotide Hybridization*, Modelling and Computer Methods In Molecular Biology and Genetics, Abstracts of the Int'l Conference, Novosibirsk, U.S.S.R. (1990).

Fisher, Lawrence M., "Technology; Microchips for Drug Compounds," *New York Times*, Late Ed., p. 7, col. 1, Mar. 3, 1991.

Fodor et al., "Light-Directed, Spatially Addressable Parallel Chemical Synthesis," Science 251:767-773 (Feb. 15, 1991).

Maskos et al., "A novel method for the analysis of multiple sequence variants by hybridisation to oligonucleotides," *Nucleic Acids Research* 21(9):2267-2268 (1993).

Maskos, "A novel method of nucleic acids sequence analysis," *Thesis submitted for the degree of Doctor of Phiosophy at the University of Oxford*, Hylry Term 1991.

U.S. Appl. No. 11/212,551, to Pirrung et al., filed Aug. 25, 2005.

R. Drmanac, "Abstracts of papers presented at the 1994 meeting on Genome Mapping & Sequencing"; "Genome Sequencing Machine," p. 60, Intergral Genetics Group, Center for Mechanistic Biology and Biotechnology, Argonne National Laboratory, Argonne, IL 60439, Cold Spring Harbor Laboratory, May 11-15, 1994 (Cover page; "Arranged by" page; Funding page; Program pp. iii, vi, xii, xiii; and p. 60).

Schembri Notice of Judicial Review Under 35 U.S.C.§ 146 (Paper No. 74), filed Oct. 3, 2006, in Interference No. 105,285.

Schembri Status Report of Judicial Review Under 35 U.S.C. § 146 (Paper No. 78), filed Apr. 6, 2007, in Interference No. 105,285.

Schembri Second Status Report (Paper No. 79), filed Oct. 5, 2007, in Interference No. 105,285.

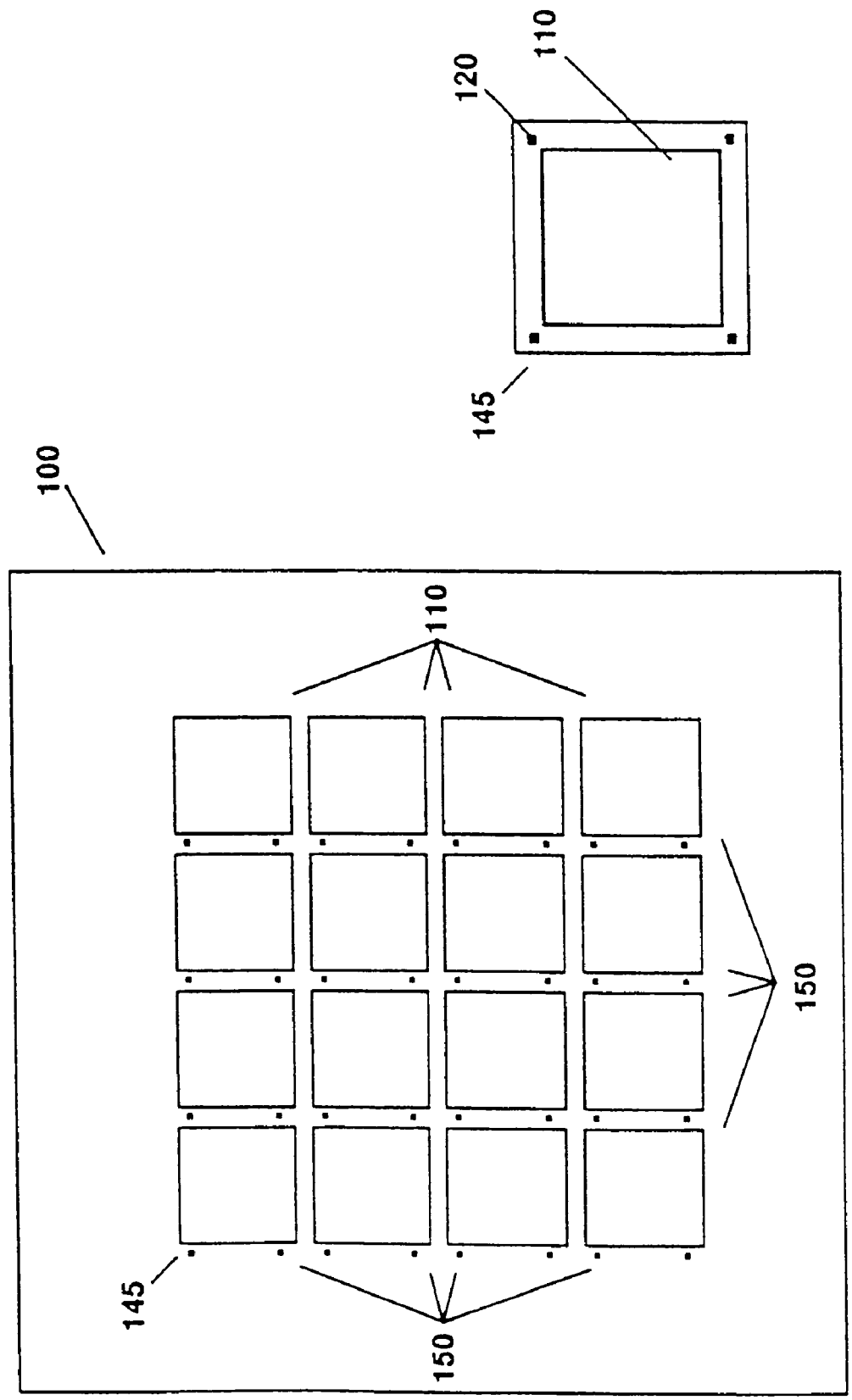

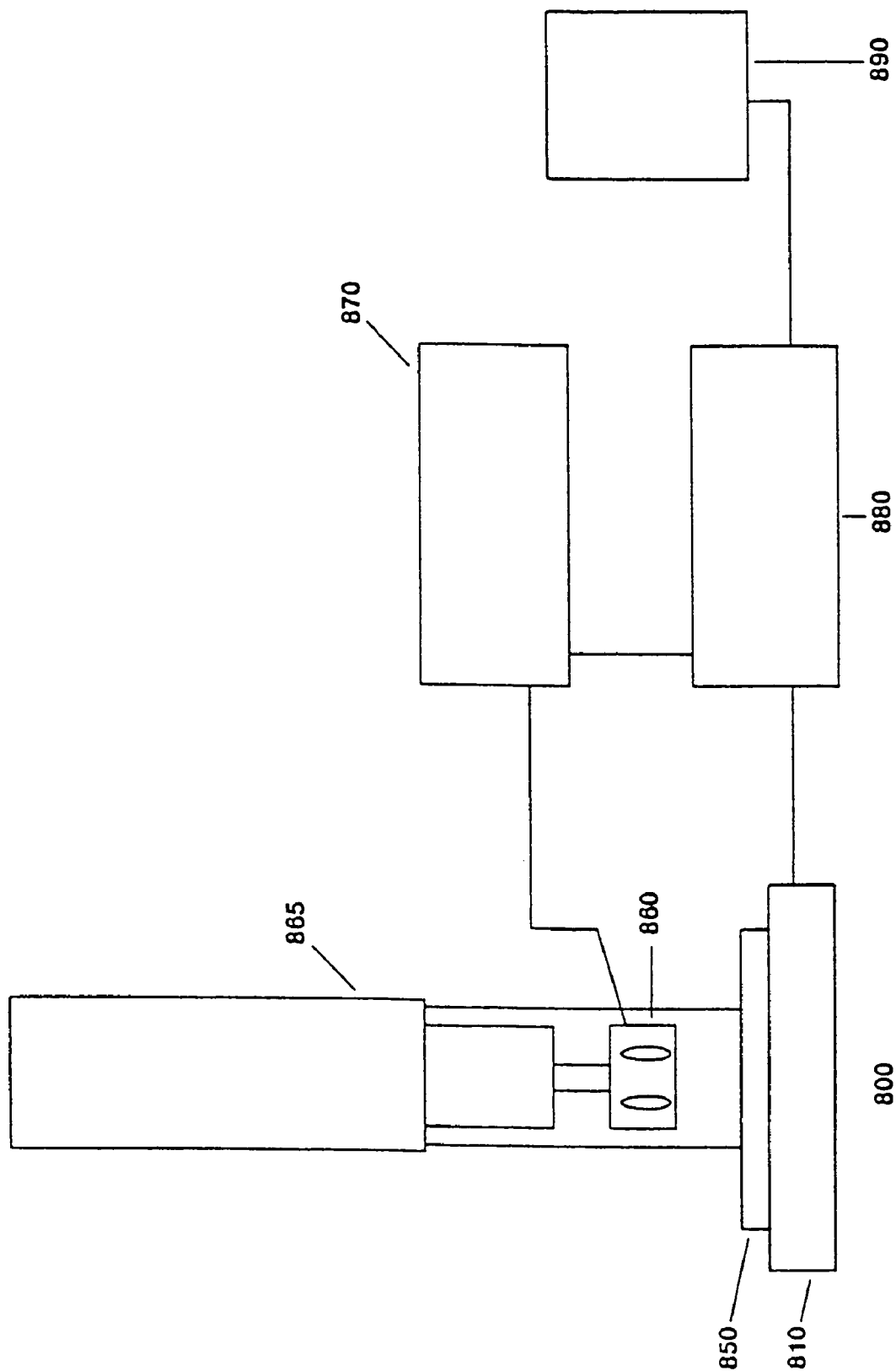

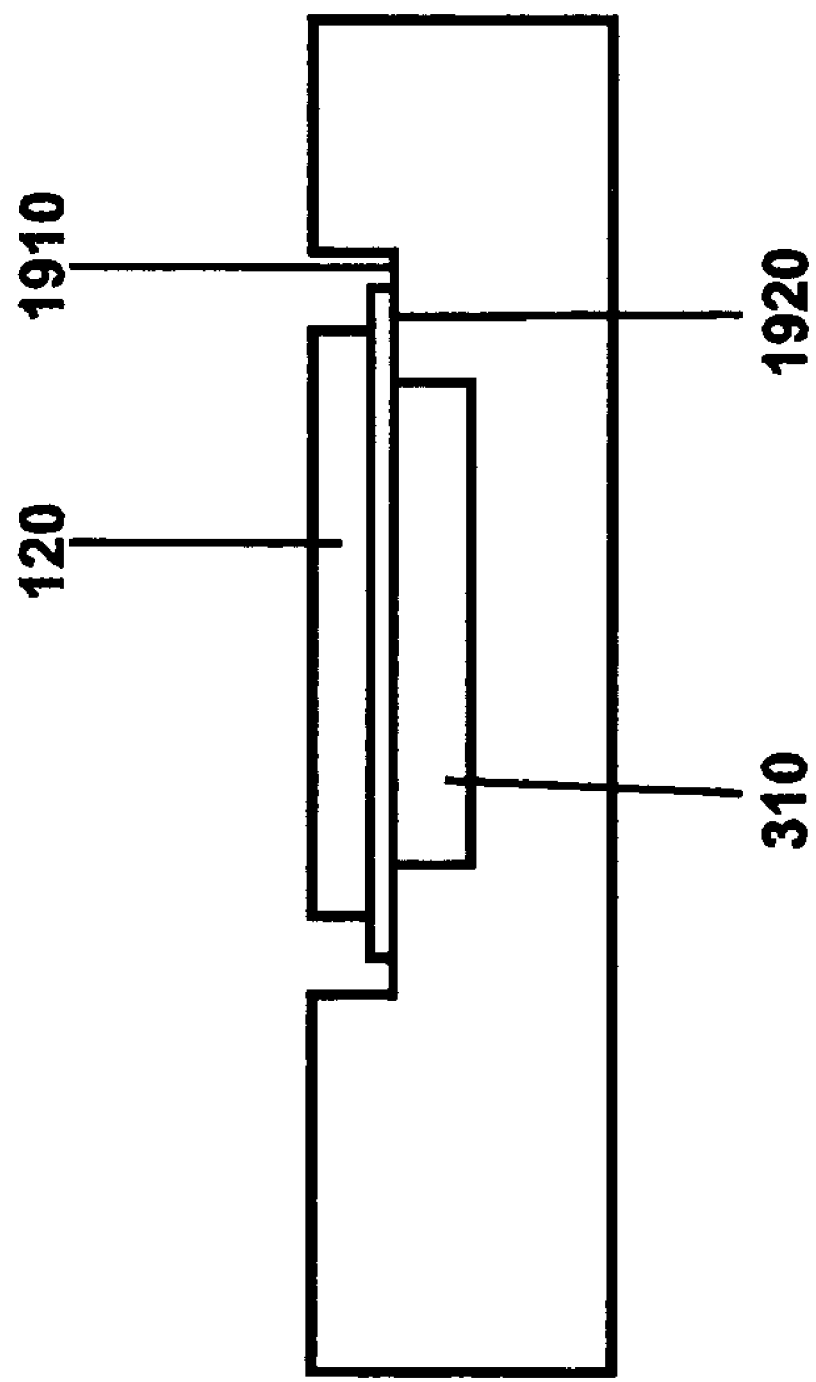

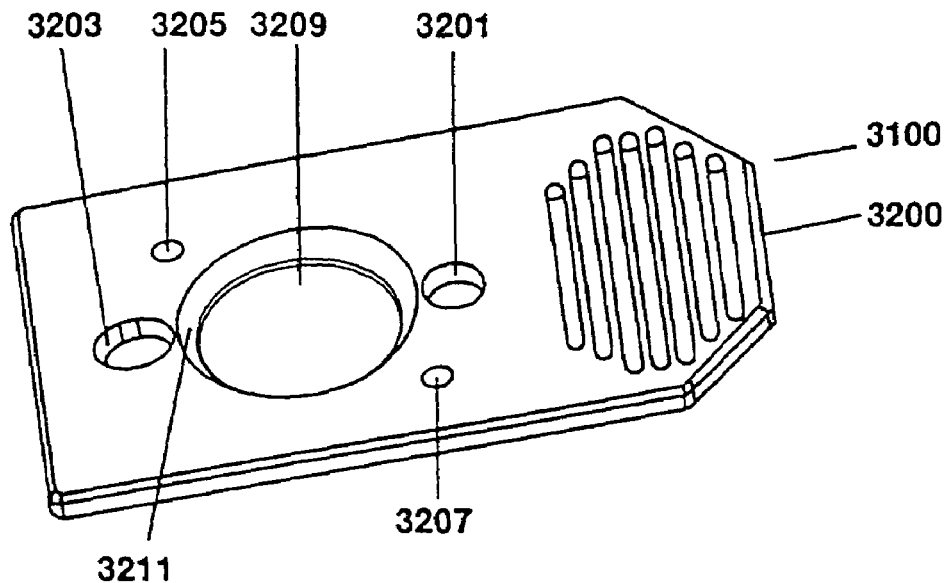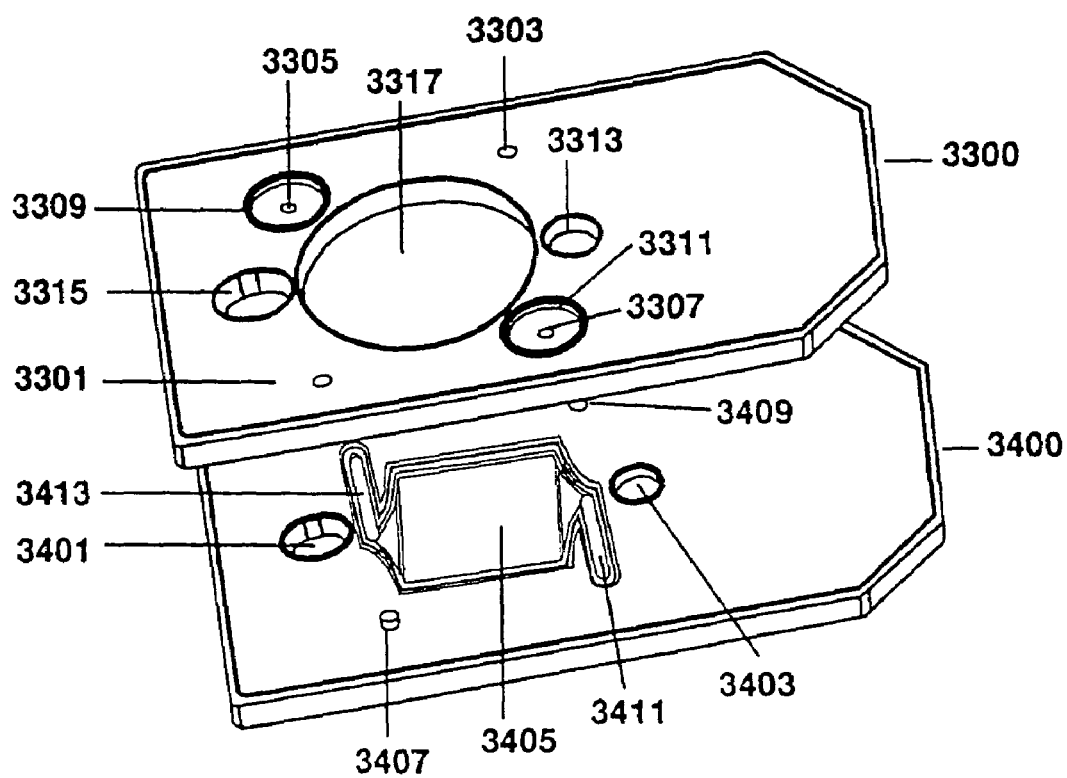
FIG. 31

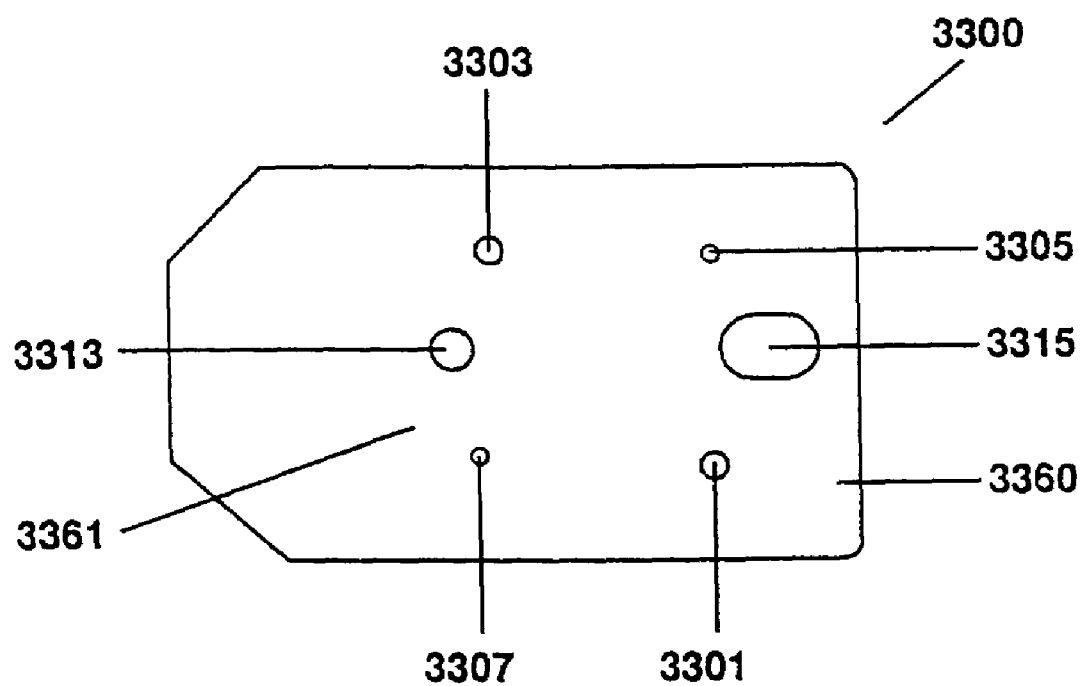
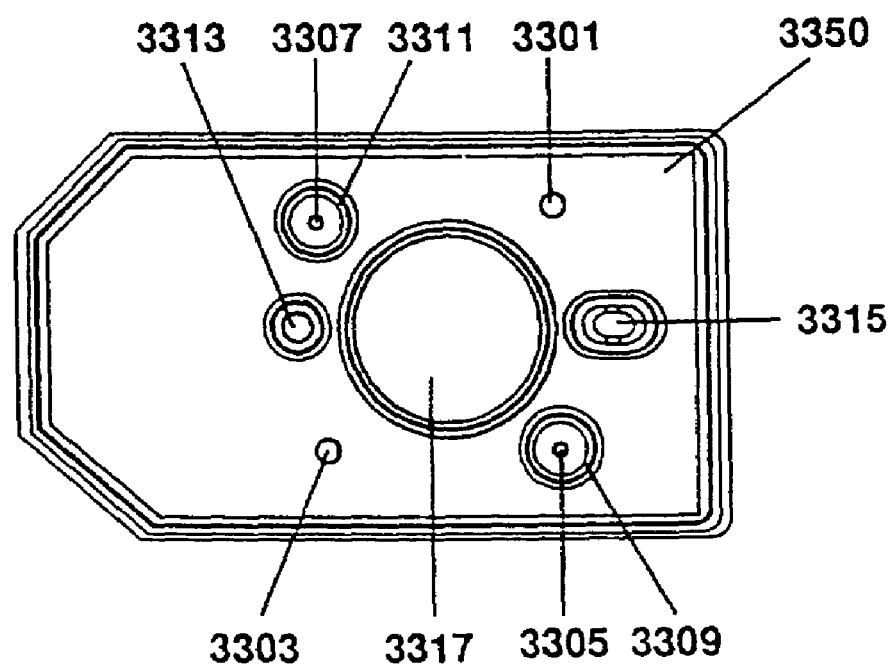
FIG. 34

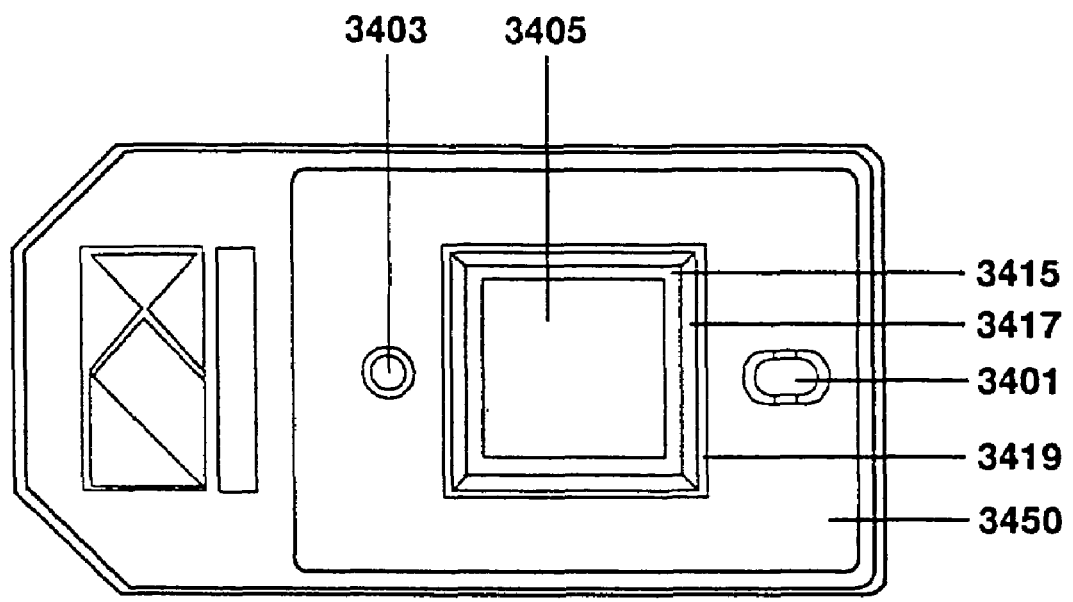
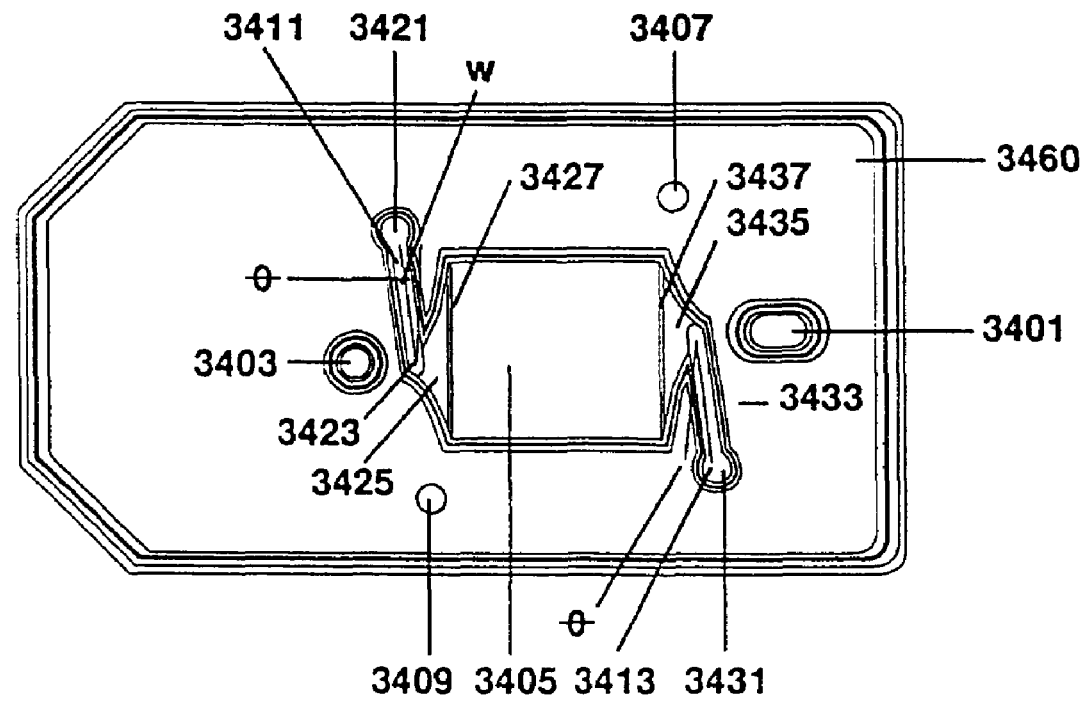
FIG. 35

BIOARRAY CHIP REACTION APPARATUS AND ITS MANUFACTURE

CROSS-REFERENCES TO RELATED APPLICATIONS

This application is a continuation of U.S. application Ser. No. 10/229,759, filed on Aug. 28, 2002, now U.S. Pat. No. 6,733,977 which is a continuation of U.S. patent application Ser. No.10/046,623, filed Jan. 14, 2002, now U.S. Pat. No. 6,551,817, which is a continuation of U.S. patent application Ser. No. 09/907,196, filed Jul. 17, 2001, now U.S. Pat. No. 6,399,365, which is a continuation of U.S. patent application Ser. No. 09/302,052, filed Apr. 29, 1999, now U.S. Pat. No. 6,287,850, which is a continuation of U.S. patent application Ser. No. 08/485,452, filed Jun. 7, 1995, now U.S. Pat. No. 5,945,334, which is continuation-in-part U.S. patent application Ser. No. 08/255,682, filed Jun. 8, 1994, now abandoned. Each of these applications is incorporated herein by reference in its entirety for all purposes.

BACKGROUND OF THE INVENTION

The present inventions relate to the fabrication and placement of materials at known locations on a substrate. In particular, one embodiment of the invention provides a method and associated apparatus for packaging a substrate having diverse sequences at known locations on its surface.

Techniques for forming sequences on a substrate are known. For example, the sequences may be formed according to the pioneering techniques disclosed in U.S. Pat. No. 5,143,854 (Pirrung et al.), PCT WO 92/10092, or U.S. application Ser. No. 08/249,188, now U.S. Pat. No. 5,571,639, incorporated herein by reference for all purposes. The prepared substrates will have a wide range of applications. For example, the substrates may be used for understanding the structure-activity relationship between different materials or determining the sequence of an unknown material. The sequence of such unknown material may be determined by, for example, a process known as sequencing by hybridization. In one method of sequencing by hybridization, a sequences of diverse materials are formed at known locations on the surface of a substrate. A solution containing one or more targets to be sequenced is applied to the surface of the substrate. The targets will bind or hybridize with only complementary sequences on the substrate.

The locations at which hybridization occurs can be detected with appropriate detection systems by labeling the targets with a fluorescent dye, radioactive isotope, enzyme, or other marker. Exemplary systems are described in U.S. Pat. No. 5,143,854 (Pirrung et al.) and U.S. patent application Ser. No. 08/143,312, also incorporated herein by reference for all purposes. Information regarding target sequences can be extracted from the data obtained by such detection systems.

By combining various available technologies, such as photolithography and fabrication techniques, substantial progress has been made in the fabrication and placement of diverse materials on a substrate. For example, thousands of different sequences may be fabricated on a single substrate of about 1.28 $cm^2$ in only a small fraction of the time required by conventional methods. Such improvements make these substrates practical for use in various applications, such as biomedical research, clinical diagnostics, and other industrial markets, as well as the emerging field of genomics, which focuses on determining the relationship between genetic sequences and human physiology.

As commercialization of such substrates becomes widespread, an economically feasible and high-throughput device and method for packaging the substrates are desired.

SUMMARY OF THE INVENTION

Methods and devices for packaging a substrate having an array of probes fabricated on its surface are disclosed. In some embodiments, a body containing a cavity is provided. A substrate having an array of probes is attached to the cavity using, for example, an adhesive. The body includes inlets that allow fluids into and through the cavity. A seal is provided for each inlet to retain the fluid within the cavity. An opening is formed below the cavity to receive a temperature controller for controlling the temperature in the cavity. By forming a sealed thermostatically controlled chamber in which fluids can easily be introduced, a practical medium for sequencing by hybridization is provided.

In other embodiments, the body is formed by acoustically welding two pieces together. The concept of assembling the body from two pieces is advantageous. For example, the various features of the package (i.e., the channels, sealing means, and orientation means) are formed without requiring complex machining or designing. Thus, the packages are produced at a relatively low cost.

In connection with one aspect of the invention, a method for making the chip package is disclosed. In particular, the method comprises the steps of first forming a plurality of probe arrays on a substrate and separating the substrate into a plurality of chips. Typically, each chip contains at least one probe array. A chip is then mated to a package having a reaction chamber with fluid inlets. When mated, the probe array is in fluid communication with the reaction chamber.

In a specific embodiment, the present invention provides an apparatus for packaging a substrate. The present apparatus includes a substrate having a first surface and a second surface. The first surface includes a probe array and the second surface is an outer periphery of the first surface. The present apparatus also includes a body having a mounting surface, an upper surface, and a cavity bounded by the mounting surface and the upper surface. The second surface is attached to the cavity and the first surface is within the cavity. A cover attached to the mounting surface for defining an upper boundary to the cavity is also included. The cavity includes a diffuser and a concentrator. The diffuser and the concentrator permit laminar fluid flow through the cavity.

A further understanding of the nature and advantages of the inventions herein may be realized by reference to the remaining portions of the specification and the attached drawings.

BRIEF DESCRIPTION OF THE DRAWINGS

FIG. 1a illustrates a wafer fabricated with a plurality of probe arrays.

FIG. 1b illustrates a chip.

FIGS. 8a-8b illustrate an acoustic welding system.

FIG. 19 illustrates another embodiment for attaching the chip to the packaging device.

FIG. 31 illustrates an alternative embodiment of a chip packaging device.

FIGS. 33-35 illustrate in greater detail the chip packaging device of FIG. 31.

Figure 2A:
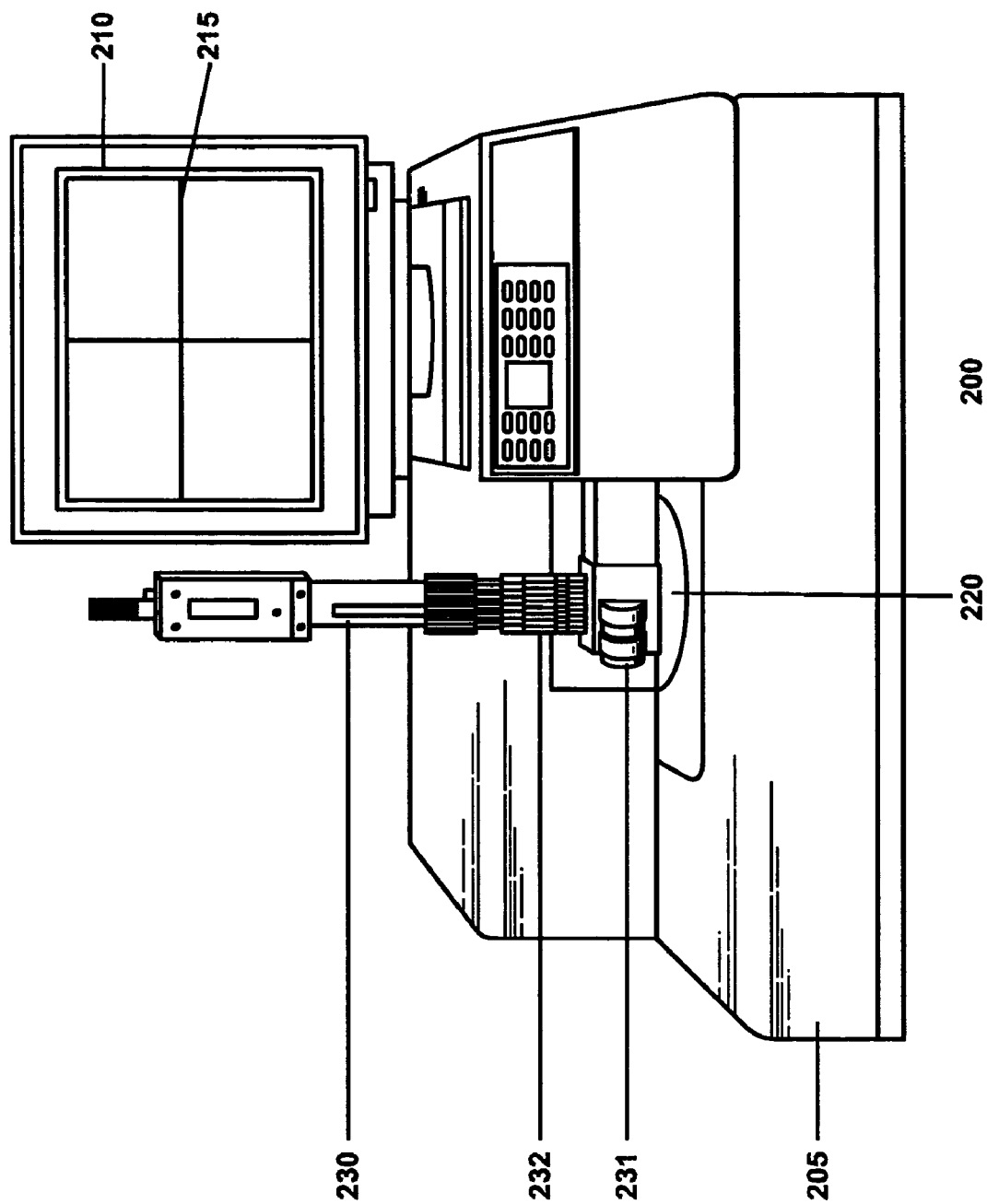
FIG. 2a illustrates a scribe and break device.

| DESCRIPTION OF THE SPECIFIC EMBODIMENTS CONTENTS | | |
|---|---|---|
| I. | Definitions | |
| II. | General | |
| III. | Details of One Embodiment of Invention | |
| | a. | Chip Package |
| | b. | Assembly of Chip Package |
| | c. | Chip Attachment |
| IV. | Details on Alternative Embodiments | |
| | a. | Chip Package |
| | b. | Chip Attachment |

| DESCRIPTION OF THE SPECIFIC EMBODIMENTS CONTENTS | | |
|---|---|---|
| -continued | | |
| | c. | Fluid Retention |
| | d. | Chip Orientation |
| | e. | Parallel Diagnostics |
| V. | Details of an Agitation System | |

I. DEFINITIONS

The following terms are intended to have the following general meanings as they are used herein:

1. Probe: A probe is a surface-immobilized molecule that is recognized by a particular target and is sometimes referred to as a ligand. Examples of probes that can be investigated by this invention include, but are not restricted to, agonists and antagonists for cell membrane receptors, toxins and venoms, viral epitopes, hormones (e.g., opioid peptides, steroids, etc.), hormone receptors, peptides, enzymes, enzyme substrates, cofactors, drugs, lectins, sugars, oligonucleotides or nucleic acids, oligosaccharides, proteins, and monoclonal antibodies.

2. Target: A target is a molecule that has an affinity for a given probe and is sometimes referred to as a receptor. Targets may be naturally-occurring or manmade molecules. Also, they can be employed in their unaltered state or as aggregates with other species. Targets may be attached, covalently or noncovalently, to a binding member, either directly or via a specific binding substance. Examples of targets which can be employed by this invention include, but are not restricted to, antibodies, cell membrane receptors, monoclonal antibodies and antisera reactive with specific antigenic determinants (such as on viruses, cells or other materials), drugs, oligonucleotides or nucleic acids, peptides, cofactors, lectins, sugars, polysaccharides, cells, cellular membranes, and organelles. Targets are sometimes referred to in the art as anti-probes or anti-ligands. As the term "targets" is used herein, no difference in meaning is intended. A "Probe Target Pair" is formed when two macromolecules have combined through molecular recognition to form a complex.

II. GENERAL

The present invention provides economical and efficient packaging devices for a substrate having an array of probes fabricated thereon. The probe arrays may be fabricated according to the pioneering techniques disclosed in U.S. Pat. No. 5,143,854 (Pirrung et al.), PCT WO 92/10092, or U.S. application Ser. No. 08/249,188 filed May 24, 1994, already incorporated herein by reference for all purposes. According to one aspect of the techniques described therein, a plurality of probe arrays are immobilized at known locations on a large substrate or wafer.

FIG. 1a illustrates a wafer 100 on which numerous probe arrays 110 are fabricated. The wafer 100 may be composed of a wide range of material, either biological, nonbiological, organic, inorganic, or a combination of any of these, existing as particles, strands, precipitates, gels, sheets, tubing, spheres, containers, capillaries, pads, slices, films, plates, slides, etc. The wafer may have any convenient shape, such as a disc, square, sphere, circle, etc. The wafer is preferably flat but may take on a variety of alternative surface configurations. For example, the wafer may contain raised or depressed regions on which a sample is located. The wafer and its surface preferably form a rigid support on which the sample can be formed. The wafer and its surface are also chosen to provide appropriate light-absorbing characteristics. For instance, the wafer may be a polymerized Langmuir Blodgett film, functionalized glass, Si, Ge, GaAs, GaP, SiO2, SiN4, modified silicon, or any one of a wide variety of gels or polymers such as (poly)tetrafluoroethylene, (poly)vinylidenedifluoride, polystyrene, polycarbonate, or combinations thereof. Other materials with which the wafer can be composed of will be readily apparent to those skilled in the art upon review of this disclosure. In a preferred embodiment, the wafer is flat glass or single-crystal silicon.

Surfaces on the solid wafer will usually, though not always, be composed of the same material as the wafer. Thus, the surface may be composed of any of a wide variety of materials, for example, polymers, plastics, resins, polysaccharides, silica or silica-based materials, carbon, metals, inorganic glasses, membranes, or any of the above-listed wafer materials.

Wafer 100 includes a plurality of marks 145 that are located in streets 150 (area adjacent to the probe arrays). Such marks may be used for aligning the masks during the probe fabrication process. In effect, the marks identify the location at which each array 110 is to be fabricated. The probe arrays may be formed in any geometric shape. In some embodiments, the shape of the array may be squared to minimize wasted wafer area. After the probe arrays have been fabricated, the wafer is separated into smaller units known as chips. The wafer, for example, may be about 5×5 inches on which 16 probe arrays, each occupying an area of about 12.8 cm$^2$, are fabricated.

FIG. 1b illustrates a chip that has been separated from the wafer. As illustrated, chip 120 contains a probe array 110 and a plurality of alignment marks 145. The marks serve multiple functions, such as: 1) aligning the masks for fabricating the probe arrays, 2) aligning the scriber for separating the wafer into chips, and 3) aligning the chip to the package during the attachment process. In some embodiments, such chips may be of the type known as Very Large Scale Immobilized Polymer Synthesis (VLSIPS™) chips.

According to a specific embodiment, the chip contains an array of genetic probes, such as an array of diverse RNA or DNA probes. In some embodiments, the probe array will be designed to detect or study a genetic tendency, characteristic, or disease. For example, the probe array may be designed to detect or identify genetic diseases such as cystic fibrosis or certain cancers (such as P53 gene relevant to some cancers), as disclosed in U.S. patent application Ser. No. 08/143,312, already incorporated by reference.

According to one embodiment, the wafer is separated into a plurality of chips using a technique known as scribe and break. FIG. 2a illustrates a fully programmable computer controlled scribe and break device, which in some embodiments is a DX-III Scriber breaker manufactured by Dynatex International™. As shown, the device 200 includes a base 205 with a rotation stage 220 on which a wafer is mounted. The rotation stage includes a vacuum chuck for fixing the wafer thereon. A stepper motor, which is controlled by the system, rotates stage 220. Located above the stage is a head unit 230 that includes a camera 232 and cutter 231. Head unit 230 is mounted on a dual-axis frame. The camera generates an image of the wafer on video display 210. The video display 210 includes a cross hair alignment mark 215. The camera, which includes a zoom lens and a fiber optic light, allows a user to inspect the wafer on the video display 210. A control panel 240 is located on the base for operating device 200.

Figure 2B:
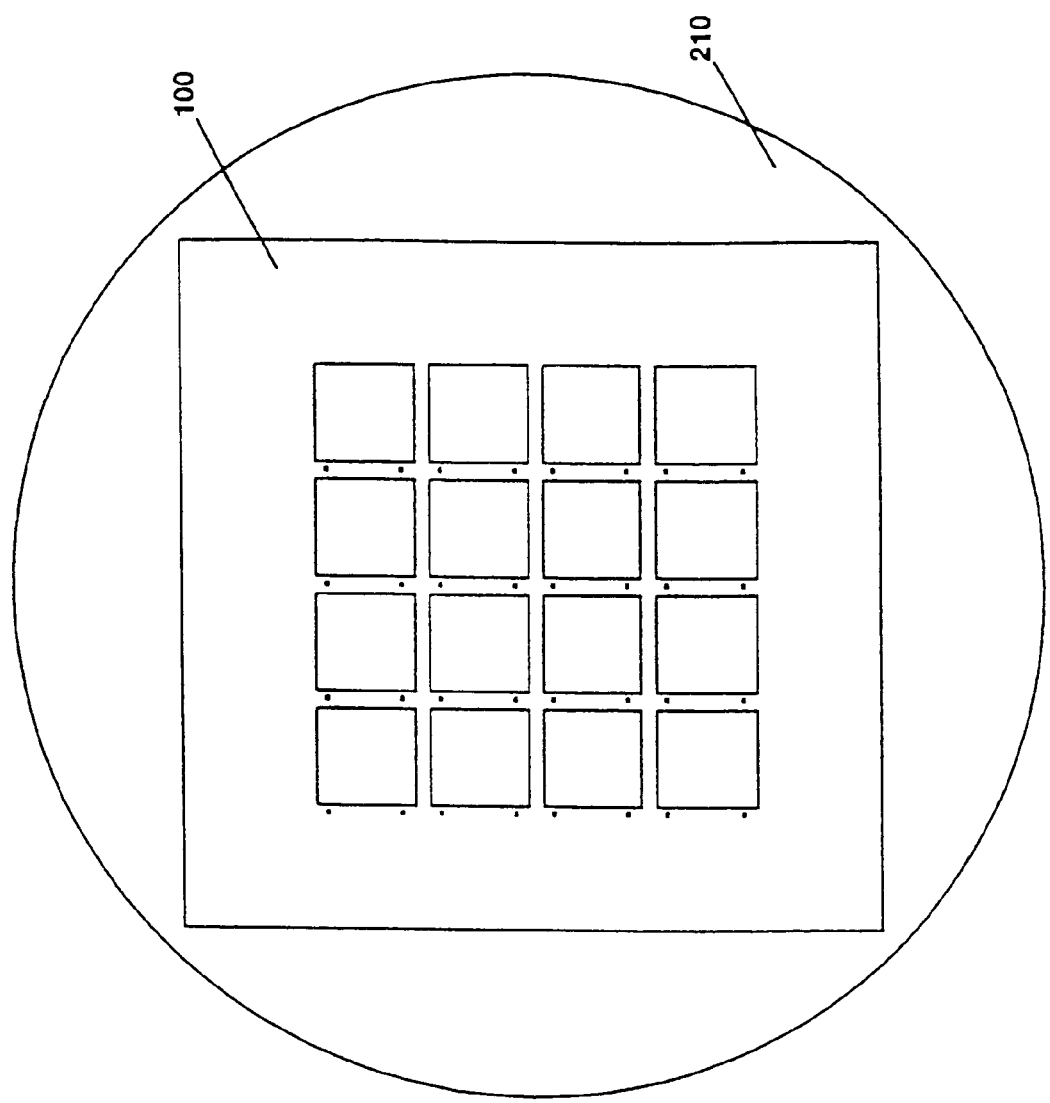
FIG. 2b illustrates the wafer mounted on a pick and place frame.

In operation, a user places a wafer 100 on a frame 210 as illustrated in FIG. 2b. The surface of frame 210 is composed of a flexible and sticky material. The tackiness of the frame prevents the chips from being dispersed and damaged during the breaking process. Frame 210 may be a pick and place frame or a hoop that is commonly associated with fabrication of semiconductors. Referring back to FIG. 2a, a user places the frame with the wafer on the rotation stage 220. In some embodiments, the frame is held on the rotation stage by vacuum pressure. The user then aligns the wafer by examining the image displayed on the video display 210.

Figure 2C:
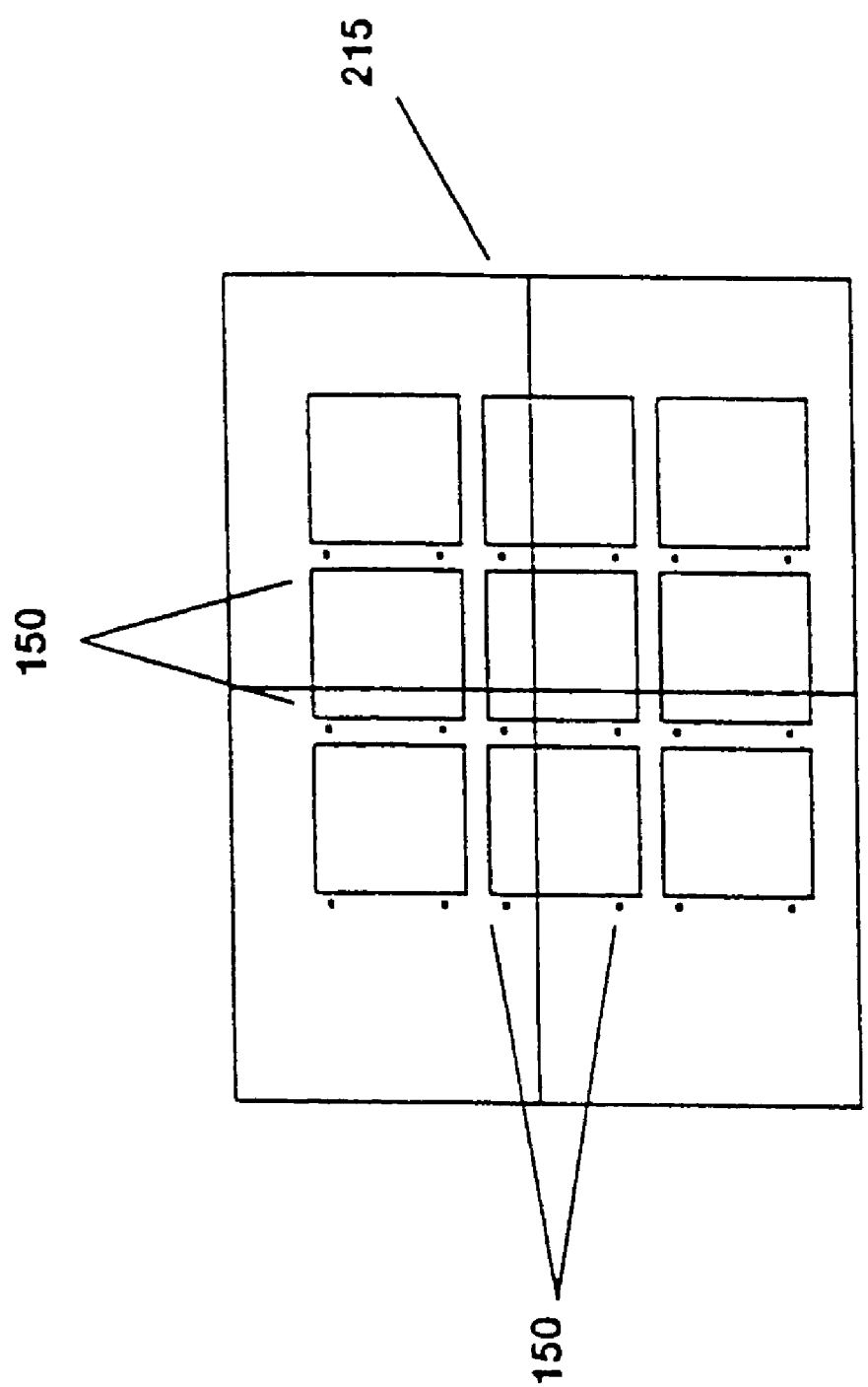
FIGS. 2c-2d illustrate the wafer, as displayed by the scribe and break device during alignment.
Figure 2D:
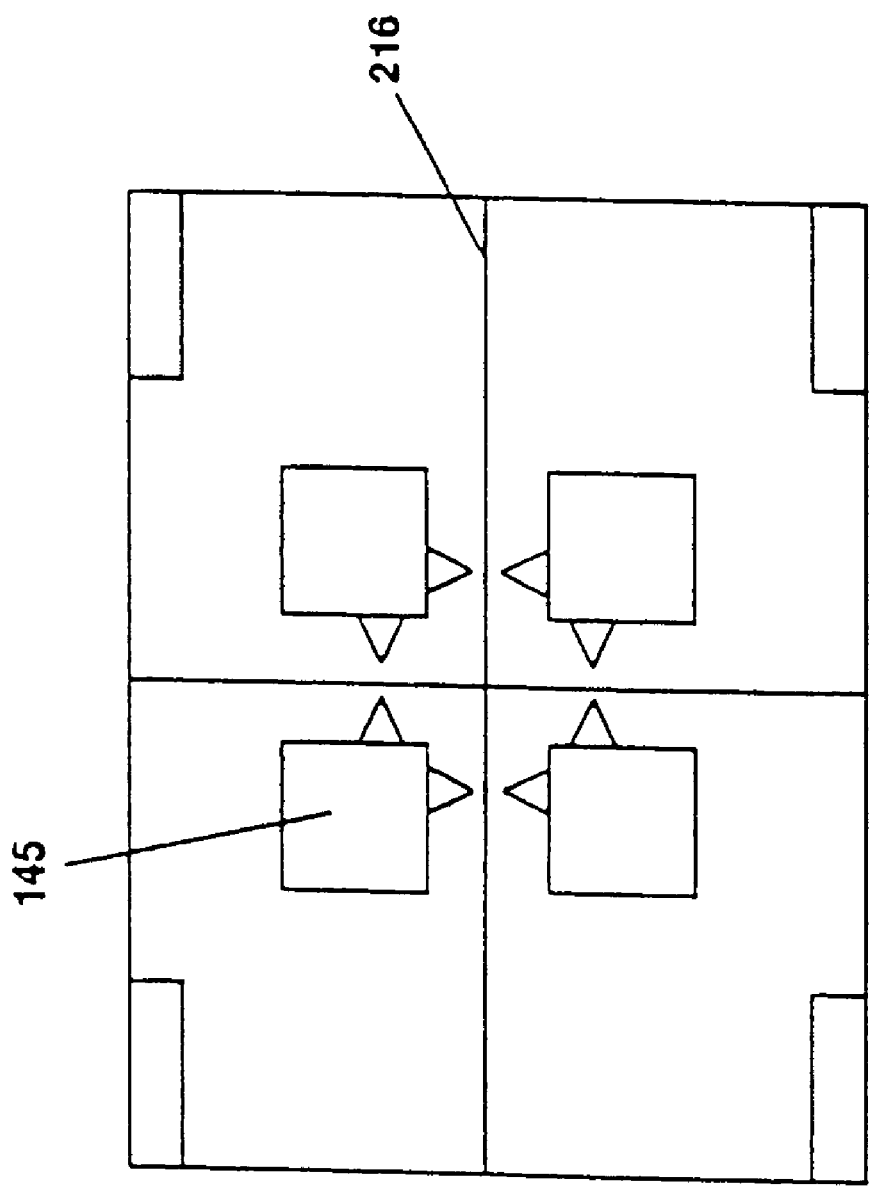

According to one embodiment, wafer alignment is achieved in two steps. First, using the control panel 240, the user rotates stage 220. The stage is rotated until streets 150 are aligned with the cross hair 215 on the display, as illustrated in FIG. 2c. Next, the user moves the cutter until it is aligned at the center of one of the streets. This step is performed by aligning horizontal line 216 of the cross hair between alignment marks 145, as shown in FIG. 2d.

Once the cutter is aligned, the user instructs the device to scribe the wafer. In some embodiments, various options are available to the user, such as scribe angle, scribe pressure, and scribe depth. These parameters will vary depending on the composition and/or thickness of the wafer. Preferably, the parameters are set to scribe and break the wafer without causing any damage thereto or penetrating through the frame. The device repeatedly scribes the wafer until all the streets in one axis have been scribed, which in one embodiment is repeated 5 times (a 4×4 matrix of probe arrays). The user then rotates the stage 90° to scribe the perpendicular streets.

Once the wafer has been scribed, the user instructs the device to break or separate the wafer into chips. Referring back to FIG. 2a, the device 200 breaks the wafer by striking it beneath the scribe with an impulse bar located under the rotation table 220. The shock from the impulse bar fractures the wafer along the scribe. Since most of the force is dissipated along the scribe, device 200 is able to produce high breaking forces without exerting significant forces on the wafer. Thus, the chips are separated without causing any damage to the wafer. Once separated, the chips are then packaged. Of course, other more conventional techniques, such as the sawing technique disclosed in U.S. Pat. No. 4,016,855, incorporated herein by reference for all purposes, may be employed.

III. DETAILS OF ONE EMBODIMENT OF THE INVENTION a. Chip Package

Figure 3:
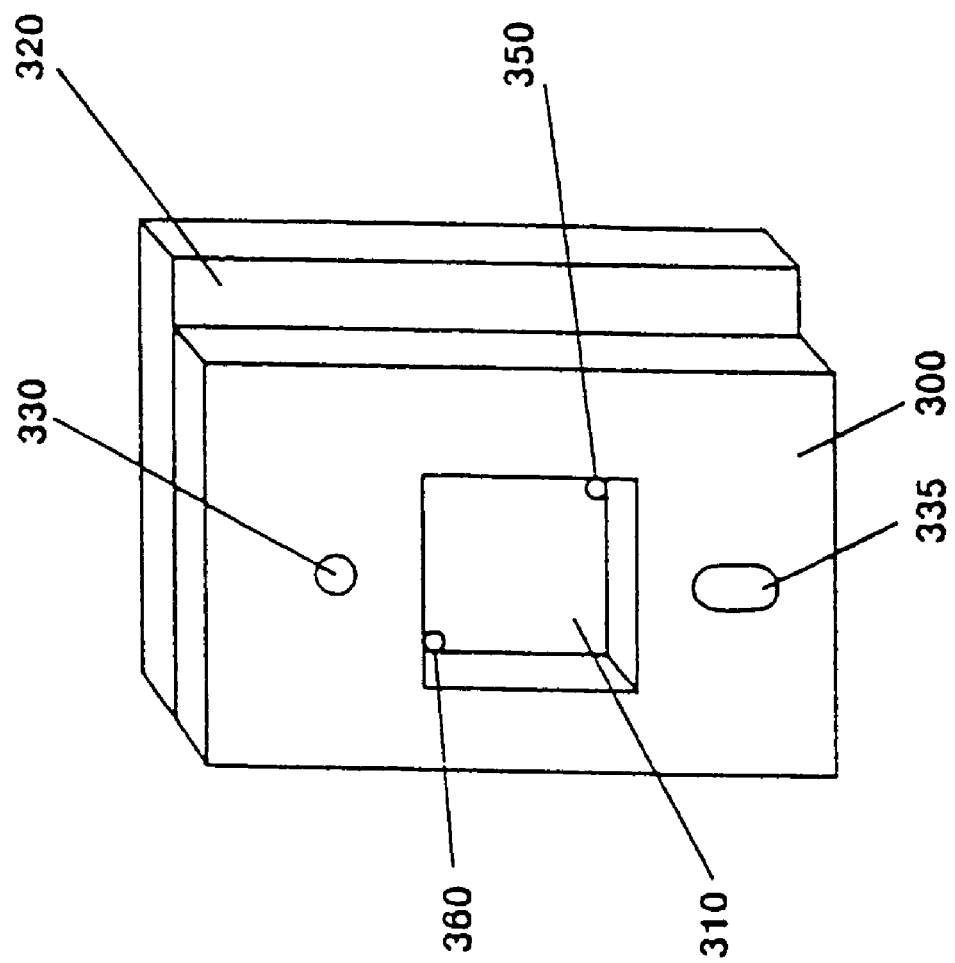
FIG. 3 illustrates a chip packaging device.

FIG. 3 illustrates a device for packaging the chips. Package 300 contains a cavity 310 on which a chip is mounted. The package includes inlets 350 and 360 which communicate with cavity 310. Fluids are circulated through the cavity via inlets 350 and 360. A septum, plug, or other seal may be employed to seal the fluids in the cavity. Alignment holes 330 and 335 may be provided for alignment purposes. In some embodiments, the package may include a non-flush edge 320. In some detection systems, the packages may be inserted into a holder similar to an audio cassette tape. The asymmetrical design of the package will assure correct package orientation when inserted into the holder.

Figure 4:
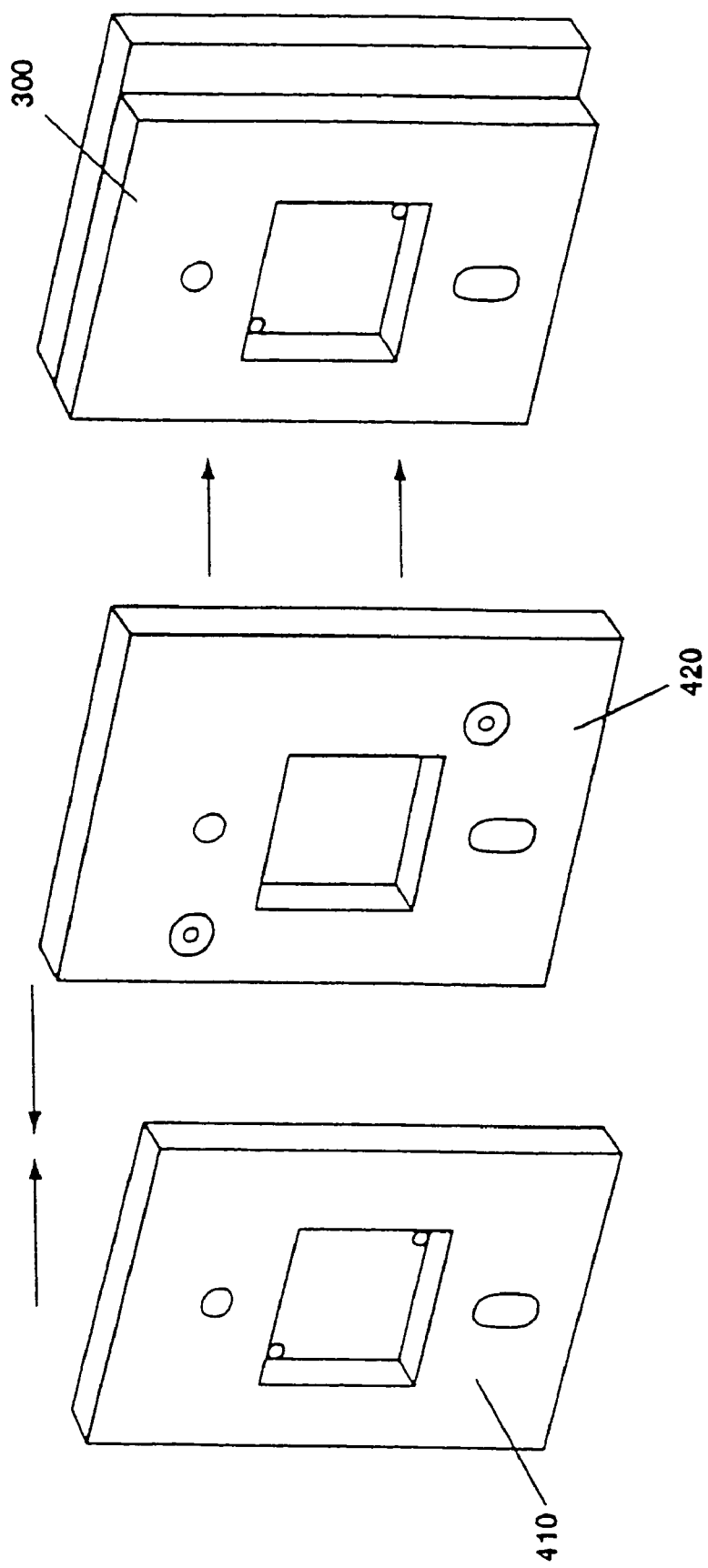
FIG. 4 illustrates the chip packaging device assembled from two components.

FIG. 4 illustrates one embodiment of the package. As shown in FIG. 4, the chip package is manufactured by mating two substantially complementary casings 410 and 420 to form finished assembly 300. Preferably, casings 410 and 420 are made from injection molded plastic. Injection molding enables the casings to be formed inexpensively. Also, assembling the package from two parts simplifies the construction of various features, such as the internal channels for introducing fluids into the cavity. As a result, the packages may be manufactured at a relatively low cost.

Figure 5B:
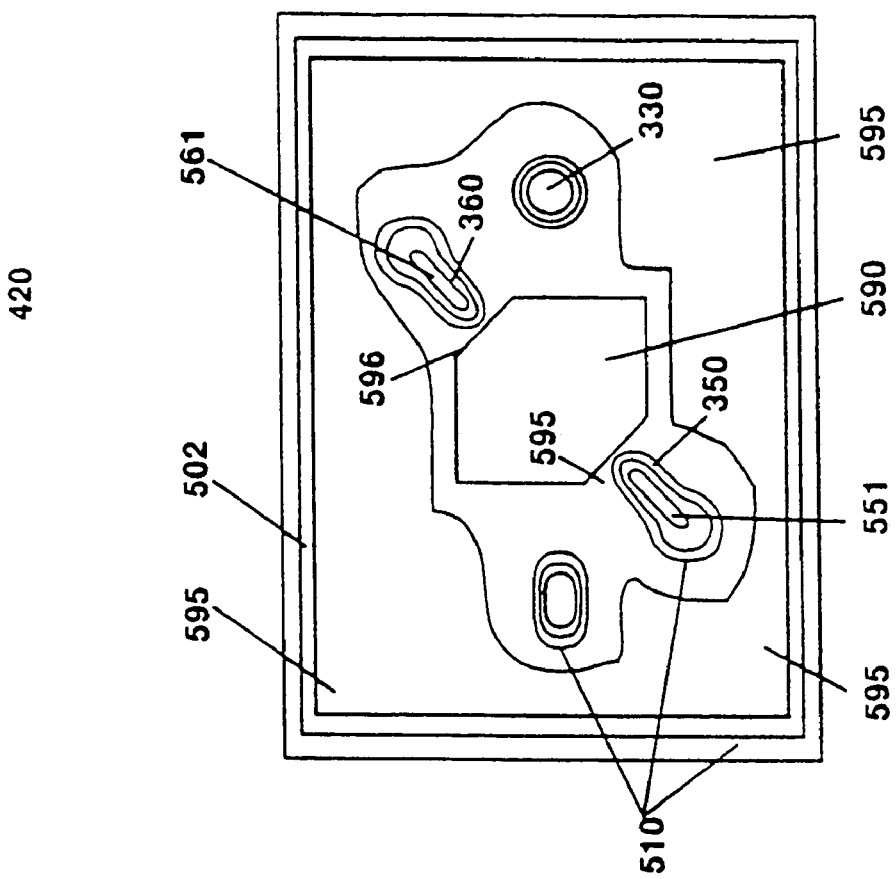
FIGS. 5a-5b illustrate the top and bottom view of a top casing of the chip packaging device.
Figure 5A:
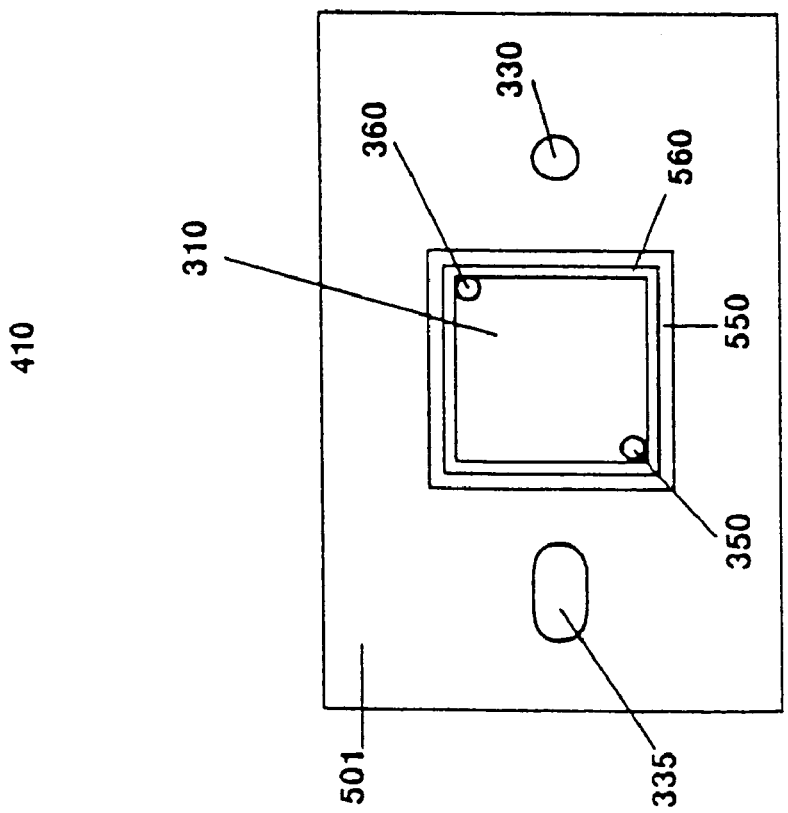

FIGS. 5a-5b show the top casing 410 in greater detail. FIG. 5a shows a top view and FIG. 5b shows a bottom view. Referring to FIG. 5a, top casing 410 includes an external planar surface 501 having a cavity 310 therein. In some embodiments, the surface area of casing 410 sufficiently accommodates the cavity. Preferably, the top casing is of sufficient size to accommodate identification labels or bar codes in addition to the cavity. In a specific embodiment, the top casing is about 1.5" wide, 2" long, and 0.2" high.

Cavity 310 is usually, though not always, located substantially at the center of surface 501. The cavity may have any conceivable size, shape, or orientation. Preferably, the cavity is slightly smaller than the surface area of the chip to be placed thereon and has a volume sufficient to perform hybridization. In one embodiment, the cavity may be about 0.58" wide, 0.58" long, and 0.2" deep.

Cavity 310 may include inlets 350 and 360. Selected fluids are introduced into and out of the cavity via the inlets. In some embodiments, the inlets are located at opposite ends of the cavity. This configuration improves fluid circulation and regulation of bubble formation in the cavity. The bubbles agitate the fluid, increasing the hybridization rate between the targets and complementary probe sequences. In one embodiment, the inlets are located at the top and bottom end of the cavity when the package is oriented vertically such as at the opposite corners of the cavity. Locating the inlet at the highest and lowest positions in the cavity facilitates the removal of bubbles from the cavity.

Figure 5C:
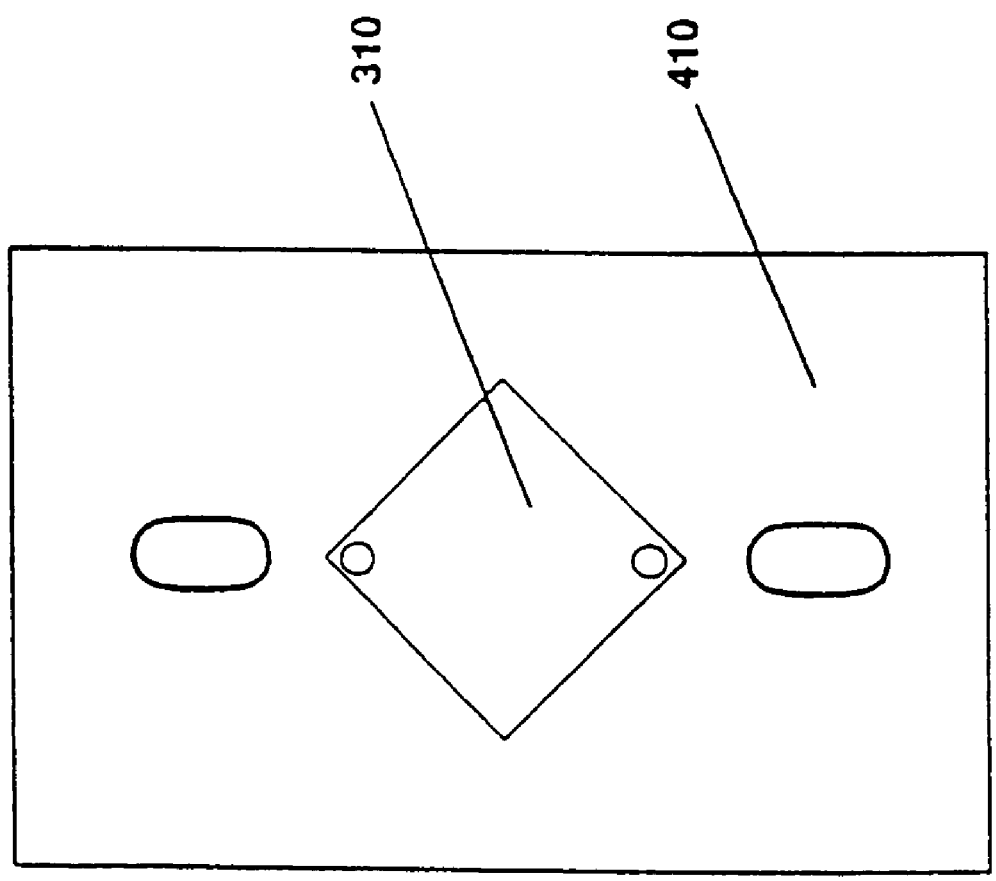
FIG. 5c illustrates a different cavity orientation.

FIG. 5c illustrates an alternative embodiment in which cavity 310 is oriented such that the edges of the cavity 310 and the casing 410 are non-parallel. This configuration allows inlets 350 and 360 to be situated at the absolute highest and lowest locations in the cavity when the package is vertically oriented. As a result, bubbles or fluid droplets are prevented from being potentially trapped in the cavity.

Referring back to FIG. 5a, a depression 550 surrounds the cavity. In some embodiments, a ridge 560 may be provided at the edge of the depression so as to form a trough. The ridge serves to support the chip above the cavity. To attach the chip to the package, an adhesive may be deposited in the trough. This configuration promotes efficient use of chip surface area, thus increasing the number of chips yielded from a wafer.

Top casing 410 includes alignment holes 330 and 335. In some embodiments, holes 330 and 335 are different in size to ensure correct orientation of the package when mounted on an alignment table. Alternatively, the holes may have different shapes to achieve this objective. Optionally, the holes taper radially inward from surface 501 toward 502 to reduce the friction against alignment pins while still maintaining adequate contact to prevent slippage.

Referring to FIG. 5b, channels 551 and 561 are optionally formed on internal surface 502. Channels 551 and 561 communicate with inlets 350 and 360 respectively. A depression 590 is formed below cavity. According to some embodiments, the shape of depression 590 is symmetrical to the cavity with exception to corners 595 and 596, which accommodate the inlets. The depth of depression 590 may be, for example, about 0.7". As a result, the bottom wall of the cavity is about 0.05" thick. Depression 590 may receive a temperature controller to monitor and maintain the cavity at the desired temperature. By separating the temperature controller and cavity with a minimum amount of material, the temperature within the cavity may be controlled more efficiently and accurately. Alternatively, channels may be formed on surface 502 for circulating air or water to control the temperature within the cavity.

In some embodiments, certain portions 595 of internal surface 502 may be eliminated or cored without interfering with the structural integrity of the package when assembled. Coring the casing reduces the wall thickness, causing less heat to be retained during the injection molding process; potential shrinkage or warpage of the casing is significantly reduced. Also, coring decreases the time required to cool the casing during the manufacturing process. Thus, manufacturing efficiency is improved.

In one embodiment, the top casing and bottom casing are mated together using a technique known as acoustic or ultrasonic welding. Accordingly, "energy directors" 510 are provided. Energy directors are raised ridges or points, preferably v-shaped, that are used in an acoustic welding process. The energy directors are strategically located, for example, to seal the channels without interfering with other features of the package and to provide an adequate bond between the two casings. Alternatively, the casings may be mated together by screws, glue, clips, or other mating techniques.

Figure 6:
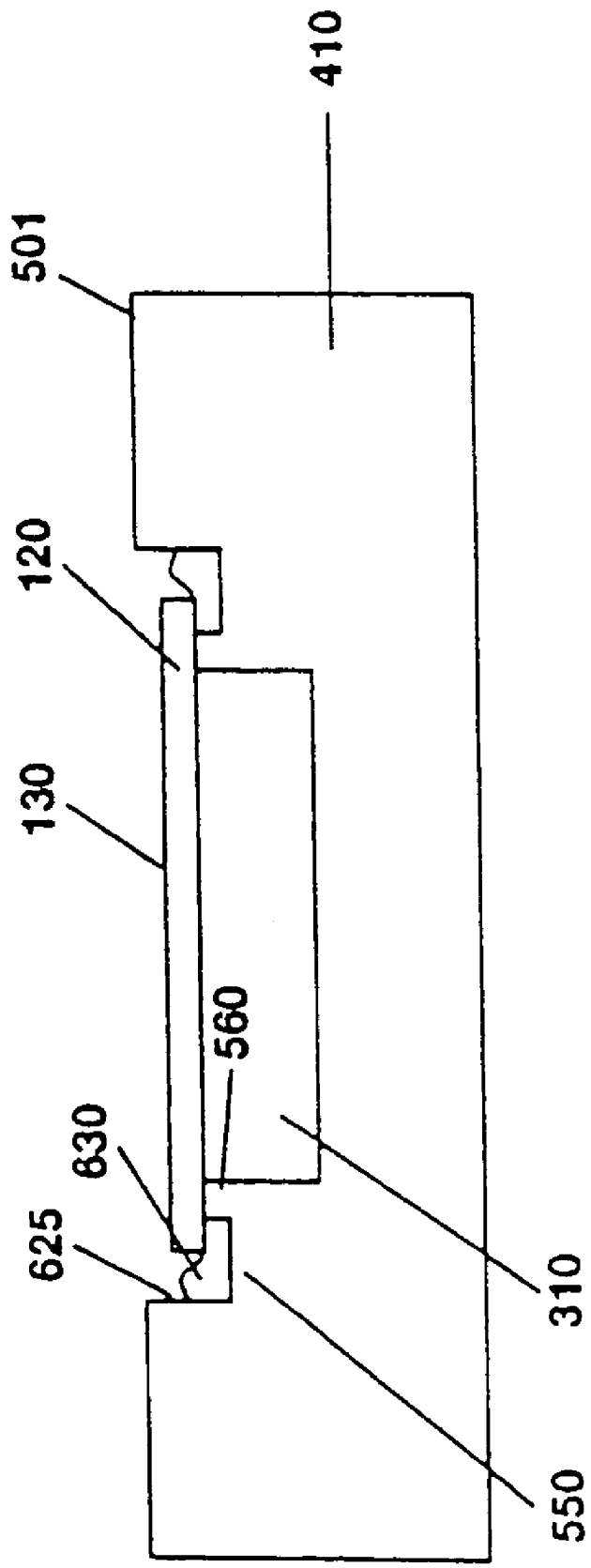
FIG. 6 illustrates a cross sectional view of the packaging device.

FIG. 6 shows a cross sectional view of the cavity 310 with chip 120 mounted thereon in detail. As shown, a depression 550 is formed around cavity 310. The depression includes a ridge 560 which supports chip 120. The ridge and the depression create a trough around cavity 310. In some embodiments, the trough is sufficiently large to receive an adhesive 630 for attaching the chip to the package. In one embodiment, the trough is about 0.08" wide and 0.06" deep. When mounted, the edge of the chip protrudes slightly beyond ridge 550, but without contacting side 625 of the depression. This configuration permits the adhesive to be dispensed onto the trough and provides adequate surface area for the adhesive to attach chip 120 to the package.

According to some embodiments, the back surface 130 of chip 120 is at least flush or below the plane formed by surface 501 of casing 410. As a result, chip 120 is shielded by surface 501 from potential damage. This configuration also allows the packages to be easily stored with minimal storage area since the surfaces are substantially flat.

Optionally, the bottom of the cavity includes a light absorptive material, such as a glass filter or carbon dye, to prevent impinging light from being scattered or reflected during imaging by detection systems. This feature improves the signal-to-noise ratio of such systems by significantly reducing the potential imaging of undesired reflected light.

Figure 7:
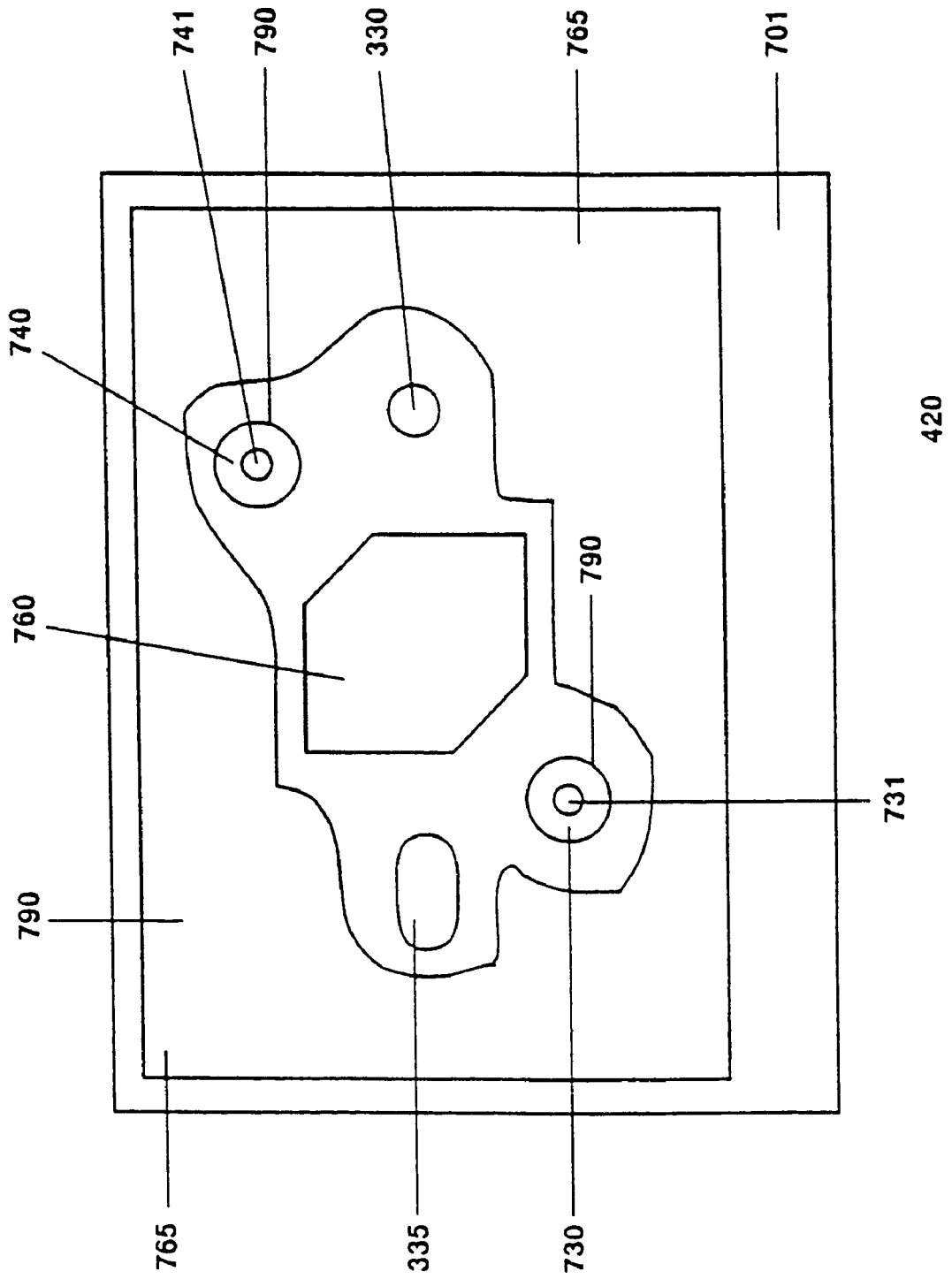
FIG. 7 illustrates the bottom view of a bottom casing of the chip packaging device.

FIG. 7 shows the internal surface of bottom casing 420 in greater detail. As shown, the bottom casing 420 is substantially planar and contains an opening 760 therein. Preferably, the casing 420 is slightly wider or slightly longer than the top casing. In one embodiment, casing 420 is about 1.6" wide, 2.0" long, and 0.1" deep, which creates a non-flush edge on the finish assembly. As previously mentioned, this design ensures that the package is correctly oriented when mounted onto the detection systems.

In some embodiments, opening 760 is spatially located at about the depression below the cavity. The opening also has substantially the same geometric configuration as the depression to allow the temperature controller to contact as much of the bottom of the cavity as possible.

Internal surface 701 of casing 420 includes depressions 730 and 740. A port 731 is located in depression 730 and a port 741 is located in depression 740. Ports 731 and 741 communicate with channels on the top casing (350 and 360 in FIG. 5b) when the package is assembled. A seal 790, which may be a septum composed of rubber, teflon/rubber laminate, or other sealing material is provided for each depression. The septum may be of the type commonly used to seal and reseal vessels when a needle is inserted into the septum for addition/removal of fluids. The septums, when seated in the depressions, extend slightly above surface, which in some embodiments is about 0.01".

This design causes casings 410 and 420 to exert pressure on the septum, forming a seal between the ports and the channels. The seal is maintained even after fluid is injected into the cavity since the pressure immediately forces the septum to reseal itself after the needle or other fluid injecting means is removed from the port. Thus, an efficient and economical seal for retaining fluid in the cavity is provided.

Also, casing 420 includes the complementary half alignment holes 330 and 335, each tapering radially inward from the external surface. Further, certain areas 765 on internal surface 701 may be cored, as similar to the internal surface of the top casing.

FIG. 31 is a simplified illustration of an alternative embodiment of a chip packaging device 3100 according to the present invention. The chip packaging device includes a plurality of casings 3200, 3300, and 3400. The casings may be defined as a top casing 3200, a middle casing 3300, and a bottom casing 3400. The casings are made of known plastic materials such as ABS plastic, polyvinylchloride, polyethylene, products sold under the trademarks TEFLON™ and KALREZ™ and the like, among others. Preferably, the casings can be made by way of injection molding and the like. Assembling the chip packaging device from three casings simplifies construction for the fabrication of internal channels and the like, and can also be made at a relatively low cost.

Support structures (or alignment holes) exist at selected locations of the chip packing device. The support structures can be used to mount or position the chip packaging device to an apparatus, e.g., scanner or the like. In an embodiment, the top casing 3200 includes support structures 3201 and 3203 on each side of a center opening 3209. The middle casing 3300 includes similar support structures 3313 and 3315 which are complementary to the support structures 3201 and 3203, respectively, in the top casing. The bottom casing also includes similar support structures 3403 and 3401, respectively, which are complementary to the support structures in the top casing and the middle casing. As shown, each of the support structures on each side of the center opening align with each other. Each support structure is, for example, an aperture through the casing. The aperture includes an outer periphery defined by a geometrical shape which may be round, rectangular, trapezoidal, hexagonal, or the like.

The present chip packaging device assembles with use of complementary alignment pins and bores on the casings. By way of alignment pins (not shown), the top casing aligns with and inserts into alignment bores 3301, 3303 in the middle casing 3300. Alternatively, the middle casing can have alignment pins or the like and the top casing has the alignment bores or the like. The bottom casing includes alignment pins 3407 and 3409 which align to and insert into alignment bores (not shown) in bottom portions of the middle casing. The use of alignment bores and pins provide for ease in assembly of the chip carrier. Upon assembly, the alignment bores and pins on the casings prevent the casings from moving laterally relative to each other.

A center opening 3209 in the top casing overlies a center portion 3317 of the middle casing 3300. The center portion 3317 of the middle casing includes an inner annular region (or cavity edges) with a bottom portion which is preferably a flat bottom portion. The flat bottom portion of the middle casing and portions of the bottom casing including edges define a cavity 3405. A chip is placed overlying an underlying portion of the cavity 3407.

Optionally, a temperature control mechanism such as a heater, a cooler, or a combination thereof is disposed into the center opening against the bottom portion of the middle casing. The temperature control mechanism can be any suitable thermally controlled element such as a resistive element, a temperature controlled block or mass, thermoelectric modules, or the like. The temperature control mechanism transfers heat via conduction to the bottom center portion, which transfers heat to, for example, fluid in the cavity or the chip. Alternatively, the temperature control mechanism sinks heat away from, for example, fluid in the cavity or the chip through the bottom center portion. The temperature control mechanism maintains a selected temperature in the cavity. The temperature control mechanism also includes a temperature detection device such as a thermocouple which provides signals corresponding to temperature readings. A controller receives the signals corresponding to the temperature readings, and adjusts power output to the temperature control mechanism to maintain the selected temperature.

The top casing 3200 also includes channels 3205 and 3207 for fluid transfer. The channels 3205 and 3207 communicate with annular regions 3309 and 3311, respectively, on the middle casing 3300 for fluid transfer. A septum, a plug, an o-ring, a gasket, or the like via annular regions 3309 and 3311 seals fluids within the top casing channels 3205 and 3207 and the middle casing. The bottom casing includes channels 3411 and 3413 in communication with channels 3307 and 3305, respectively. A septum, a plug, an o-ring, a gasket, or the like seals the fluids within the bottom casing channels 3411 and 3413 and the middle casing channels 3305 and 3307.

The chip packaging device provides an even distribution of fluid (or fluid flow) through the cavity over a top surface (or inner or active surface) of the chip. For example, a selected fluid enters channel 3207, flows through channel 3307, changes direction and flows through channel 3411, and evenly distributes into the cavity 3405 over the top surface of the chip. As previously noted, the cavity is defined by the flat bottom portion and cavity edges. A selected fluid exits the cavity by way of channel 3413, channel 3305, and channel 3205. The fluid flow over the top surface of the chip is preferably laminar, but may also be turbulent, a combination thereof or the like. By way of the present chip packaging device, a substantial portion of turbulent flow remains at an upper portion of the channel 3411, and does not enter the cavity.

Preferably, a selected fluid enters the cavity by way of channel 3205, channel 3305, and channel 3413. The selected fluid exits the cavity through channel 3411, channel 3307, and channel 3207. In a preferred embodiment, the fluid flows against the direction of gravity through the cavity. Of course, other fluid flow routes may also be employed depending upon the particular application.

Figure 32:
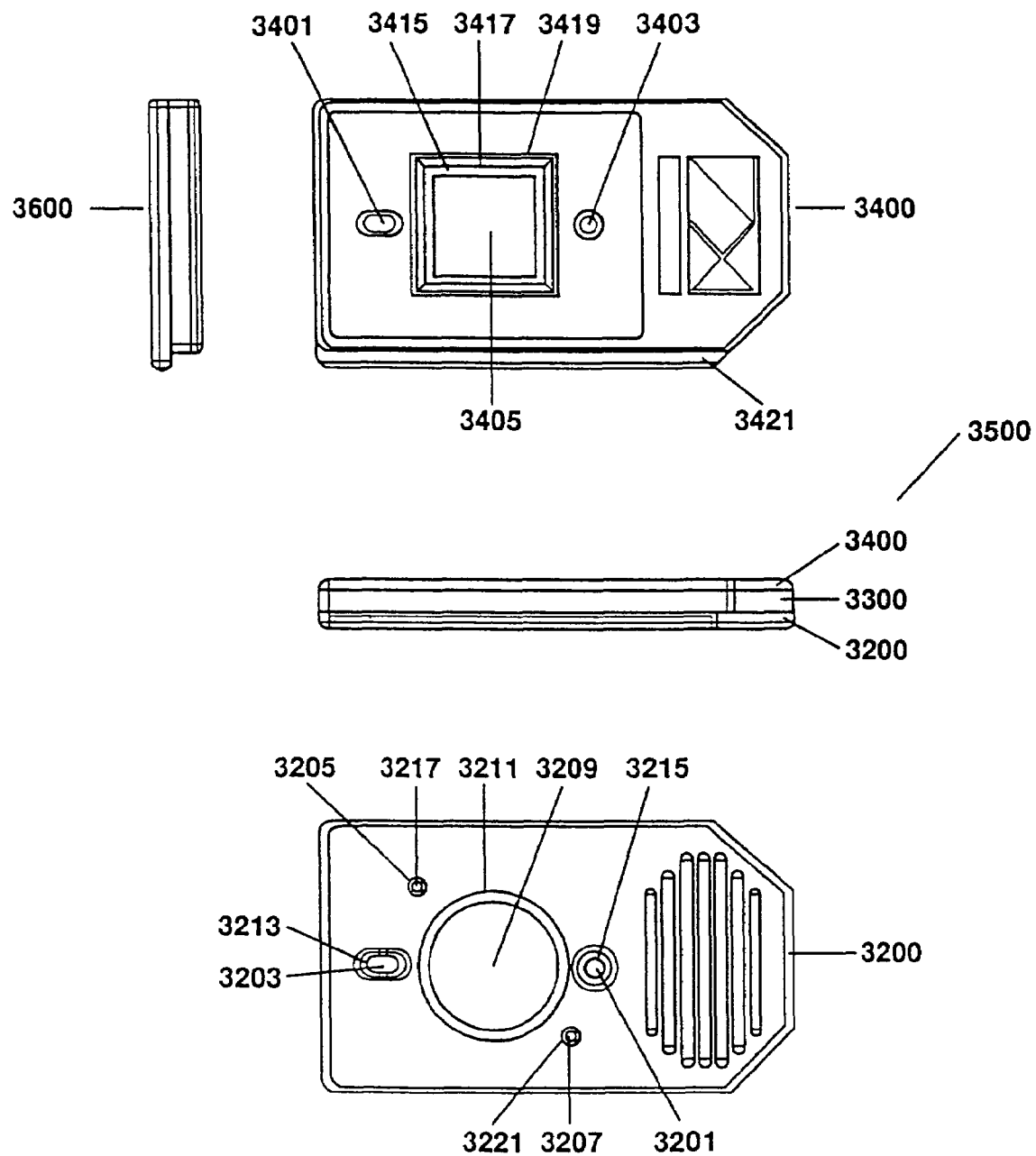
FIG. 32 illustrates side-views of the chip packaging device of FIG. 31.

FIG. 32 illustrates an assembled chip packaging device 3100 according to the present invention. As shown are a top-view 3200, a side-view 3500, a bottom-view 3400, and a front-view 3600 of the assembled chip packaging device 3100. The assembled chip packaging device 3100 includes the bottom casing 3400, the middle casing 3300, and the top casing 3200.

The top-view 3200 of the top casing includes alignment structures 3205, 3215 surrounding opening 3209. The opening 3209 includes a bevelled annular region 3211 surrounding the periphery of the channel 3209. The alignment bores 3203 and 3201 also include bevelled annular regions 3213 and 3215, respectively. A bevelled annular region 3217, 3221 also surrounds each fluid channel 3205, 3207 to assist with fluid flow therethrough.

The bottom-view 3400 of the bottom casing includes alignment structures 3401, 3403 surrounding the cavity 3405. The cavity includes a flat bottom peripheral portion 3415, a bevelled portion 3417 extending from the flat bottom peripheral portion, and a flat upper portion 3419 surrounding the bevelled portion. The chip includes an outer periphery which rests against the flat bottom peripheral portion 3415. The bevelled portion aligns the chip onto the flat bottom peripheral portion 3415. Similar to the previous embodiments, the top casing extends outside 3421 the middle and bottom casings.

The cavity 3405 is preferably located at a center of the bottom casing, but may also be at other locations. The cavity may be round, square, rectangular, or any other shape, and orientation. The cavity is preferably smaller than the surface area of the chip to be placed thereon, and has a volume sufficient to perform hybridization and the like. In one embodiment, the cavity includes dimensions such as a length of about 0.6 inch, a width of about 0.6 inch and a depth of about 0.07 inch.

In a preferred embodiment, the bottom casing with selected cavity dimensions may be removed from the middle and top casings, and replaced with another bottom casing with different cavity dimensions. This allows a user to attach a chip having a different size or shape by changing the bottom casing, thereby providing ease in using different chip sizes, shapes, and the like. Of course, the size, shape, and orientation of the cavity will depend upon the particular application.

Figure 33:
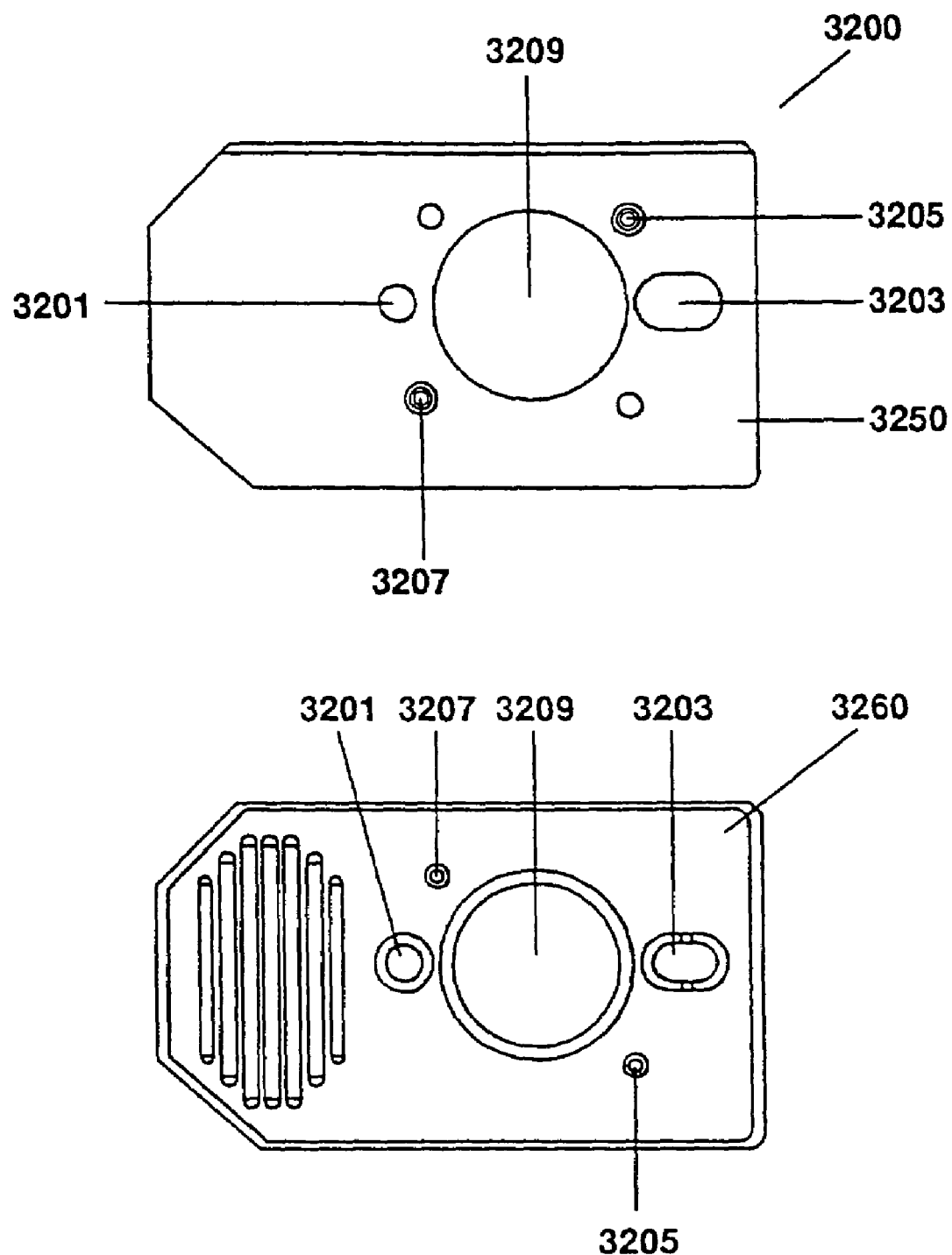

FIGS. 33-35 illustrate in greater detail the chip packaging device of FIG. 31. FIG. 33 illustrates simplified top-view 3260 and bottom-view 3250 diagrams of the top casing 3200. As shown, the reference numerals refer to the same elements as the top casing of FIG. 31. FIG. 34 illustrates a simplified top-view 3350 and bottom-view 3360 diagrams of the middle casing 3300. As shown, the reference numerals refer to the same elements as the middle casing of FIG. 31. In addition, the bottom-view of the casing includes a substantially smooth and planar bottom surface 3361. A portion of the bottom surface defines an upper portion of the cavity. But the bottom surface can also be textured, ridged, or the like to create turbulence or a selected fluid flow through the cavity. The bottom surface is preferably a hydrophobic surface which enhances laminar flow through the cavity. Of course, the type of bottom surface depends upon the particular application.

FIG. 35 illustrates simplified top-view 3460 and bottom-view 3450 diagrams of the bottom casing 3400. As shown, the reference numerals refer to the same elements as the bottom casing of FIG. 31. In an embodiment, fluid from channel 3305 changes direction at an upper portion 3431 of the channel and flows to a lower portion 3433 of the channel. Fluid evenly distributes from the lower portion 3433 via a fluid distribution point 3435. The distributed fluid evenly passes over a slanted edge (or bevelled edge) 3437 which drops fluid evenly to a top surface of the chip in the cavity. By way of slanted edge 3427 which slopes up to a fluid concentration point 3425, fluid leaves the cavity and enters the channel 3411. In particular, fluid leaves the cavity and enters a lower portion 3423 of the channel, flows through the channel, and changes directions at an upper portion 3421 of the channel. Each channel includes a length L and a width W. The distribution point and the concentration point are positioned at a distance away from the cavity to substantially prevent turbulence from forming in the cavity, and in particular over the top surface of the chip. The channels are each angled at an angle $\Theta$ ranging from about 2 degrees to about 90 degrees, but is preferably about 5 degrees to about 45 degrees. The angle enhances an even distribution of laminar flow into the cavity. Of course, the exact angle, channel shape, and dimensions depend upon the particular application.

Figure 36:
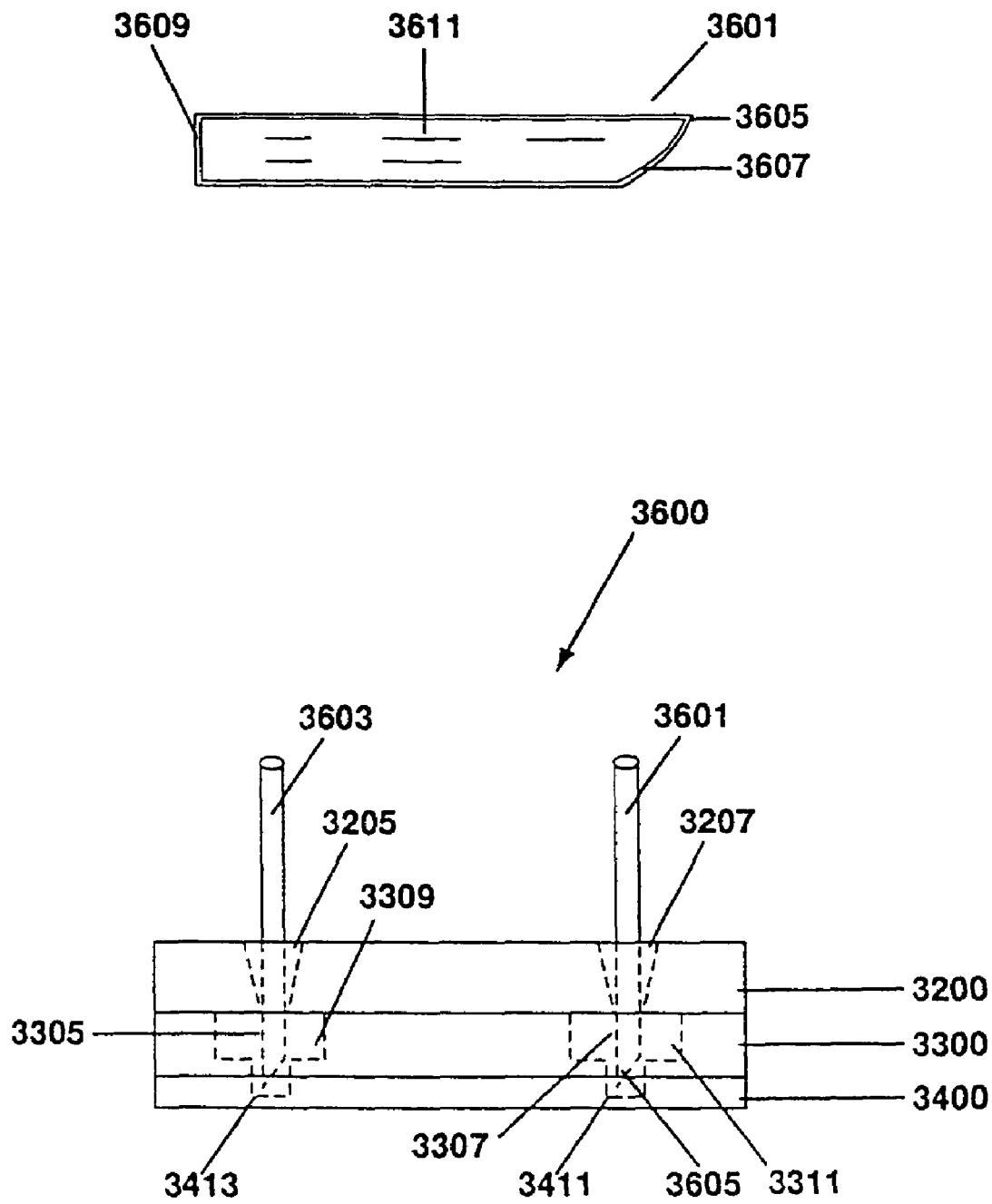
FIG. 36 illustrates a further alternative embodiment of a chip packaging device.

FIG. 36 illustrates a simplified cross-sectional view of an alternative embodiment 3600 of the chip packaging device. The chip packaging device includes the three casings 3200, 3300, and 3400 of the previous embodiment, and also includes hollow pins, needles, or the like 3601 and 3603. Each of the pins transfers a selected fluid to and from the cavity 3405. Preferably, each pin 3601 includes an external opening 3609, a tubular region 3611, an inner opening 3607, a pointed tip 3605, and other elements. The pin is made from a suitable material such as a glass, a stainless steel or any other high quality material to transfer fluids to and from the cavity 3405.

In a preferred embodiment, each pin is inserted into its channel region 3205 or 3207. A point on the pin tip pierces through, for example, a septum at an annular region 3309 or 3311. A selected fluid travels through pin 3603 (through channel 3205 and at least a portion of 3305), enters the upper region of channel 3413, and into the cavity 3405. The selected fluid travels from the cavity, through pin 3601, and to the external apparatus. Alternatively, the selected fluid enters the cavity via pin 3601 and exits the cavity via pin 3603. The selected fluid may also enter the cavity via pin and exit the cavity through the channels without use of a pin. The selected fluid may further enter the cavity through the channels without use of a pin and exit through a pin. Of course, the particular pin used and fluid flow will depend upon the application.

It should be noted that the even distribution of fluid flow through the cavity prevents "hot spots" from occurring in the cavity. For example, the even distribution of fluid through the cavity by way of the previous embodiment substantially prevents fluid from becoming substantially turbulent at certain locations. This prevents "hot spots" caused by such turbulent fluid. The hot spots are often caused by higher chemical activity or exothermic reactions and the like by way of turbulence in such certain locations.

b. Assembly of Chip Package

According to one embodiment, the top and bottom casing are attached by a technique known as ultrasonic or acoustic welding. FIG. 8a is a schematic diagram of acoustic welding system used for assembling the package. In some embodiments, the welding system 800 is a HS Dialog ultrasonic welder manufactured by Herrmann Ultrasonics Inc. System 800 includes a platform 850 mounted on base 810. Platform 850 accommodates the top and bottom casings during the assembling process.

An acoustic horn 860 is mounted on a frame above platform 850. The horn translates vertically (toward and away from platform 850) on the frame by air pressure. The horn is connected to a frequency generator 870, which in some embodiments is a 20 KHz generator manufactured by Herrmann Ultrasonics Inc. System 800 is controlled by a controller 880, which, for example, may be a Dialog 2012 manufactured by Herrmann Ultrasonics Inc. Controller 880 may be configured to accept commands from a digital computer system 890. Computer 890 may be any appropriately programmed digital computer of the type that is well known to those skilled in the art such as a Gateway 486DX operating at 33 MHz.

Figure 8B:
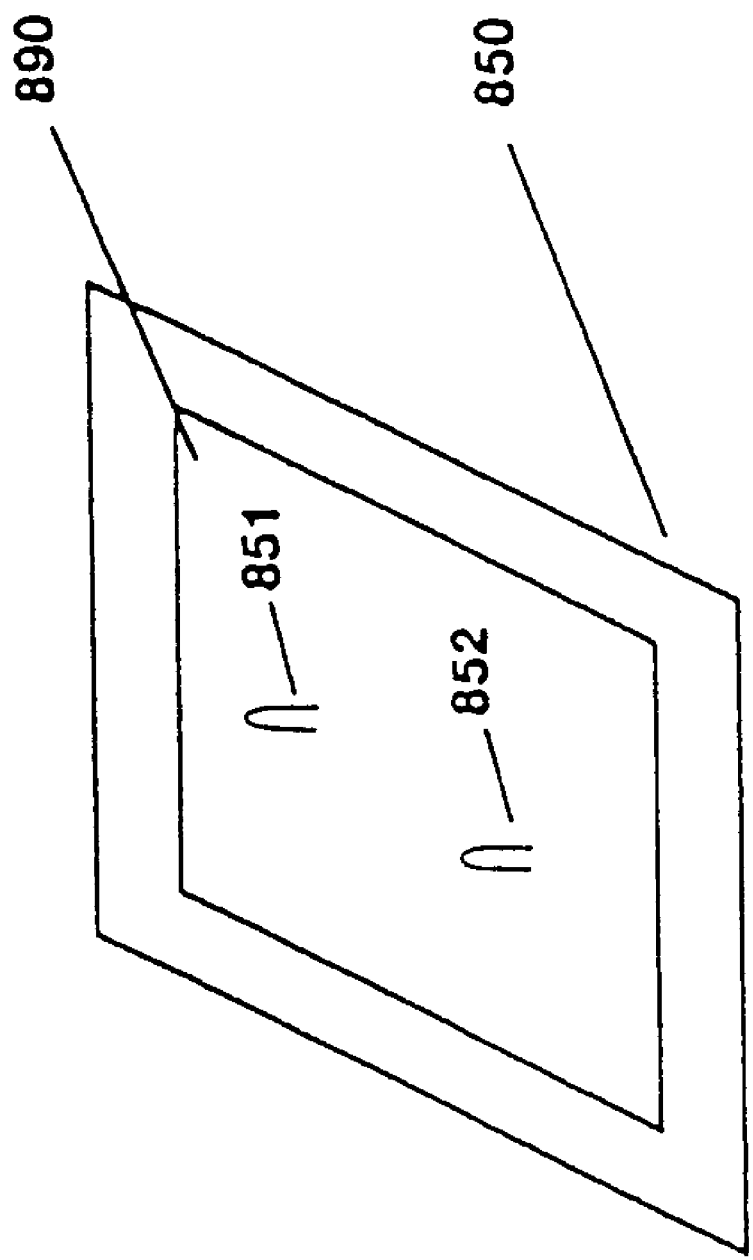

FIG. 8*b* illustrates platform 850 in greater detail. The platform 850 is substantially planar and includes alignment pins 851 and 852. Alignment pins 851 and 852 are used to align both the top and bottom casings during the welding process. In some embodiments, a pad 890, which may be composed of silicone rubber or other energy absorbing material, is located on platform 850 to prevent damage to the package during assembly.

Figure 9A:
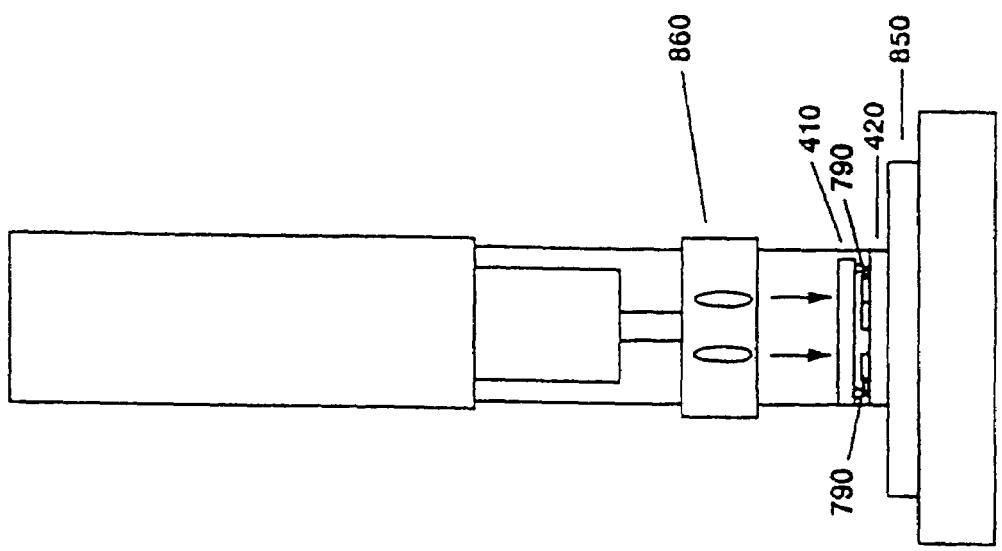
FIGS. 9a-9c illustrate the acoustic welding process used in assembling the chip packaging device.

FIG. 9*a* illustrates the acoustic welding system in operation. As shown, bottom casing 420, having a septum 790 seated in each depression, is mounted onto platform table 850 and held in place by alignment pins. Top casing 410 is then aligned above the bottom casing with alignment pins. The system then commences the welding process by lowering horn 860 until it contacts the top surface of casing 410.

Figure 9B:
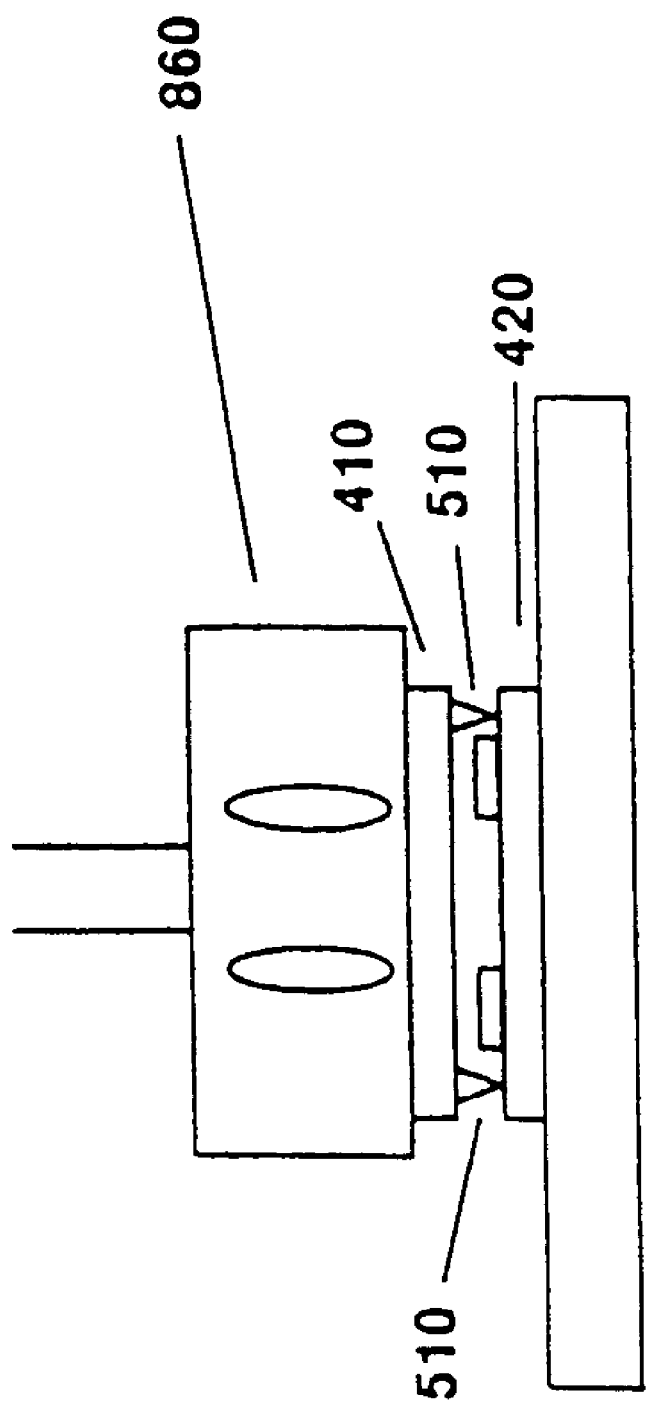

FIG. 9*b* illustrates the casing and horn in detail. As shown, the horn 860 presses against top casing 410, thereby forcing energy directors 510 to interface with bottom casing 420. The system then activates the frequency generator, causing the welding horn to vibrate.

Figure 9C:
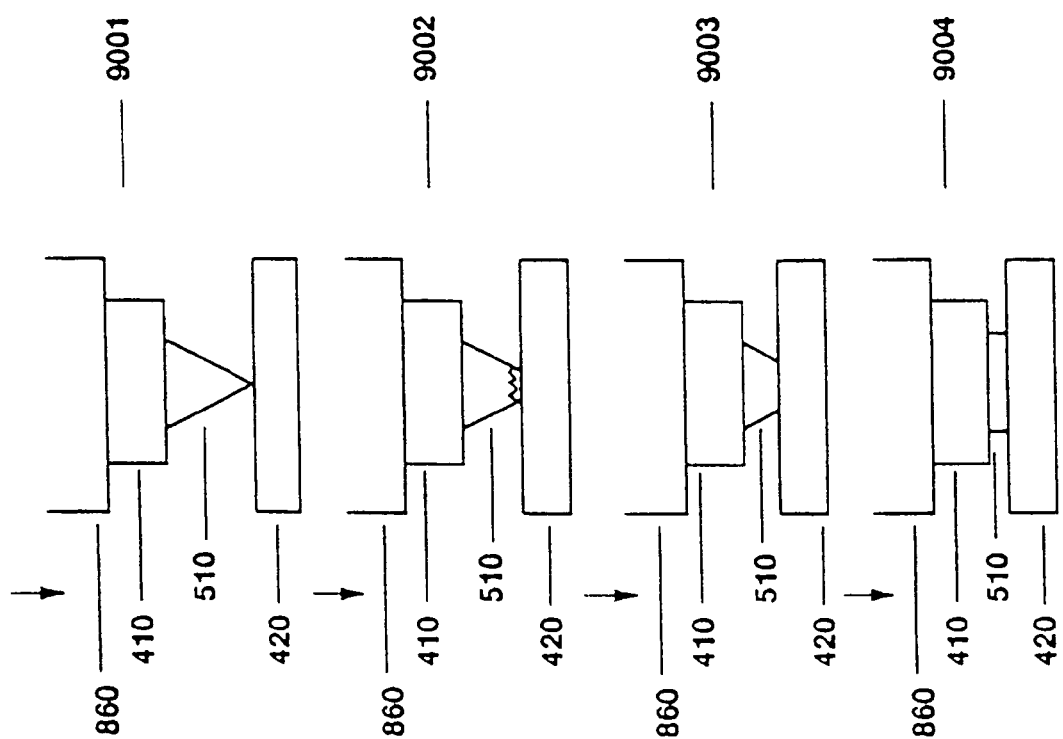

FIG. 9*c* illustrates in detail the energy directors during the welding process. As shown in step 9001, welding horn 860 forces energy directors 510 against bottom casing 420. At step 9002, the system vibrates the welding horn, which in some embodiments is at 20 KHz. The energy generated by the horn melts the energy directors. Simultaneously, the horn translates downward against the package. At step 9003, the pressure exerted by the horn causes the energy directors to fuse with the bottom casing. At step 9004, the welding process is completed when the horn reaches its weld depth, for example, of about 0.01". Of course, the various welding parameters may be varied, according to the composition of the materials used, to achieve optimum results.

c. Chip Attachment

Figure 10:
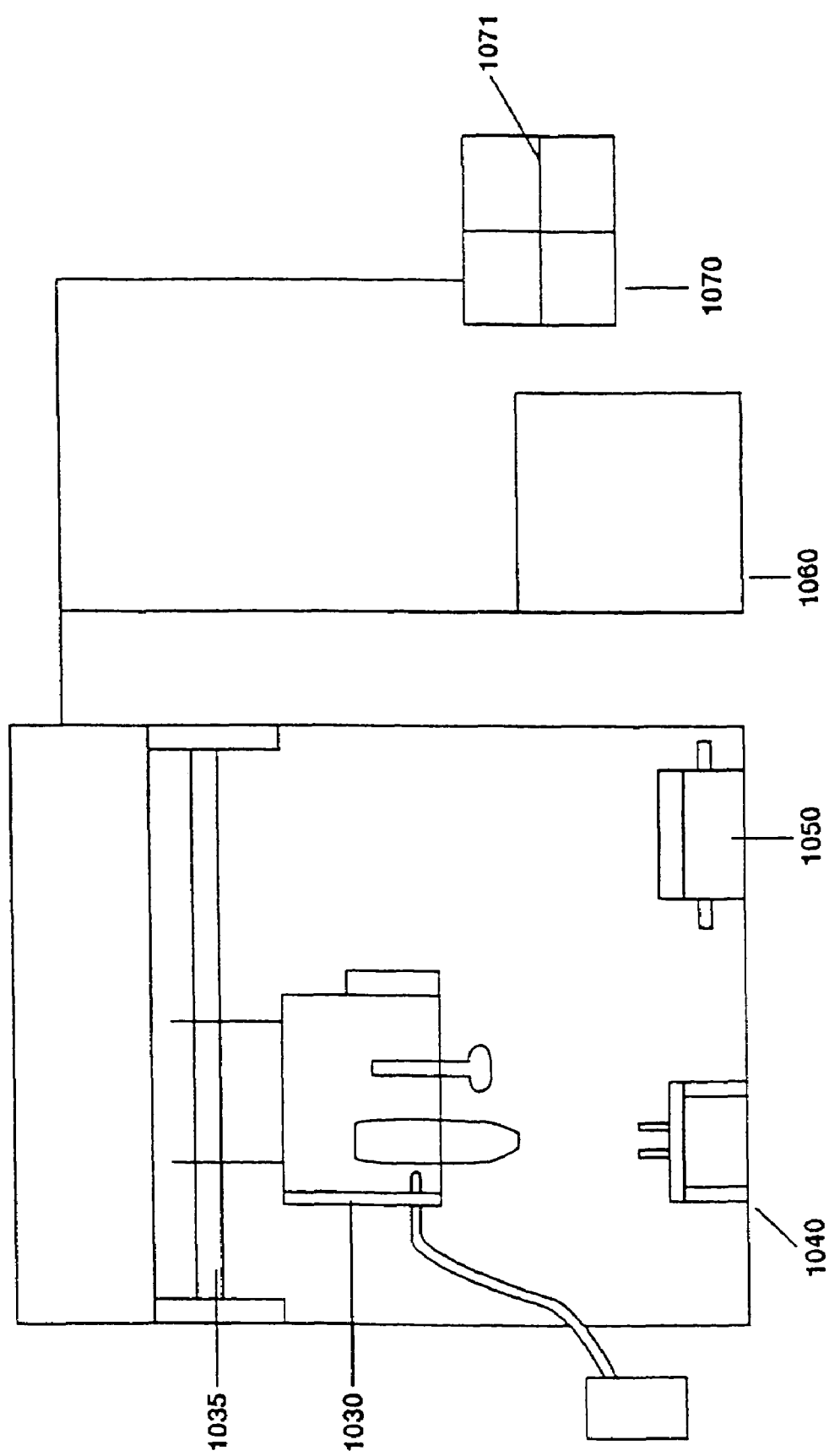
FIG. 10 illustrates an adhesive dispensing system used in attaching the chip to the chip packaging device.

According to some embodiments, an ultraviolet cured adhesive attaches the chip to the package. FIG. 10 schematically illustrates an adhesive dispensing system used in attaching the chip. The dispensing system 1000 includes an attachment table 1040 to accommodate the package during the attachment process. A chip alignment table 1050 for aligning the chip is located adjacent to attachment table 1040. A head unit 1030 for dispensing the adhesive is located above tables 1040 and 1050. The head unit 1030 also includes a camera that generates an output to video display 1070. Video display 1070, in some embodiments, includes a cross hair alignment mark 1071. The head unit is mounted on a dual-axis (x-y) frame for positioning during alignment and attachment of the chip. The operation of the dispensing system is controlled by a computer 1060, which in some embodiments may be Gateway 486DX operating at 33 MHz.

Figure 11:
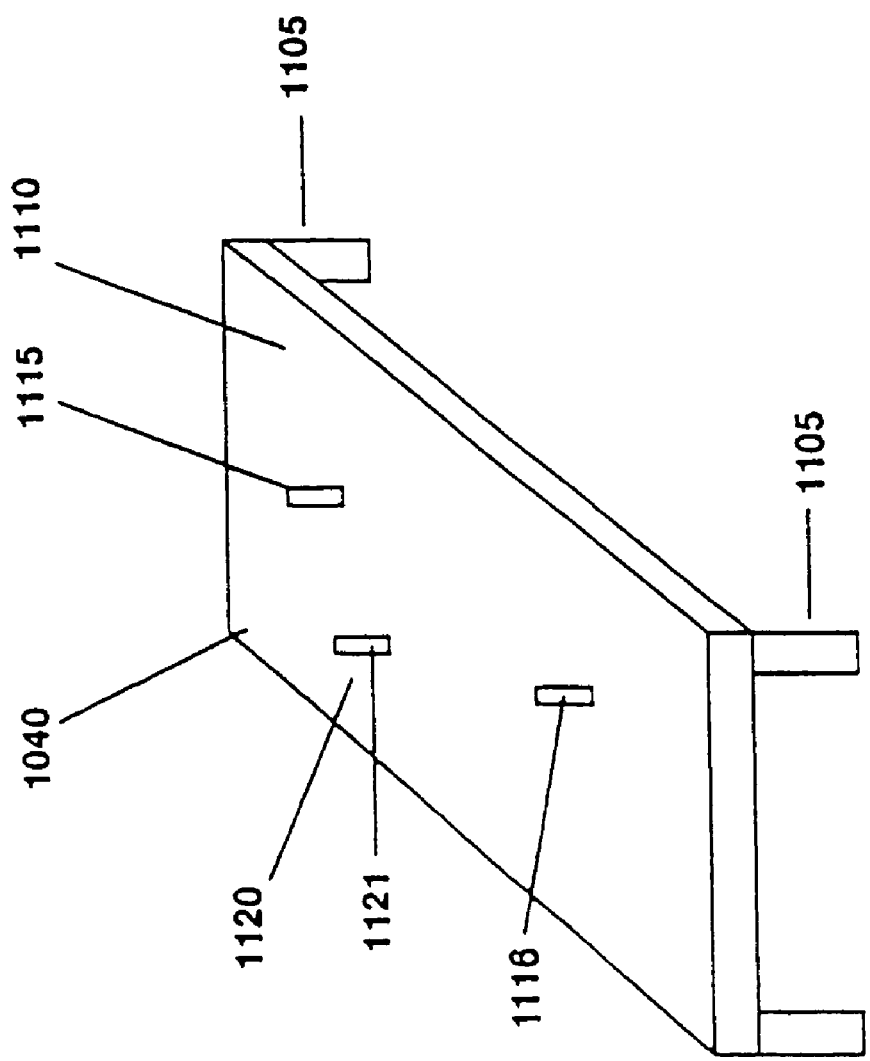
FIGS. 11-13 illustrate in greater detail the adhesive dispensing system of FIG. 10.

FIG. 11 illustrates the attachment table in greater detail. The attachment table 1040 has a substantially flat platform 1110 supported by a plurality of legs 1105. Alignment pins 1115 and 1116, which secure the package during the attachment process, are located on the surface of platform 1110.

Optionally, a needle 1120 is provided. Needle 1120 includes a channel 1121 and is connected to a vacuum pump. In operation, the needle is inserted into one of the ports of the package in order to generate a vacuum in the cavity. The vacuum pressure secures the chip to the package during the attachment process.

Figure 12A:
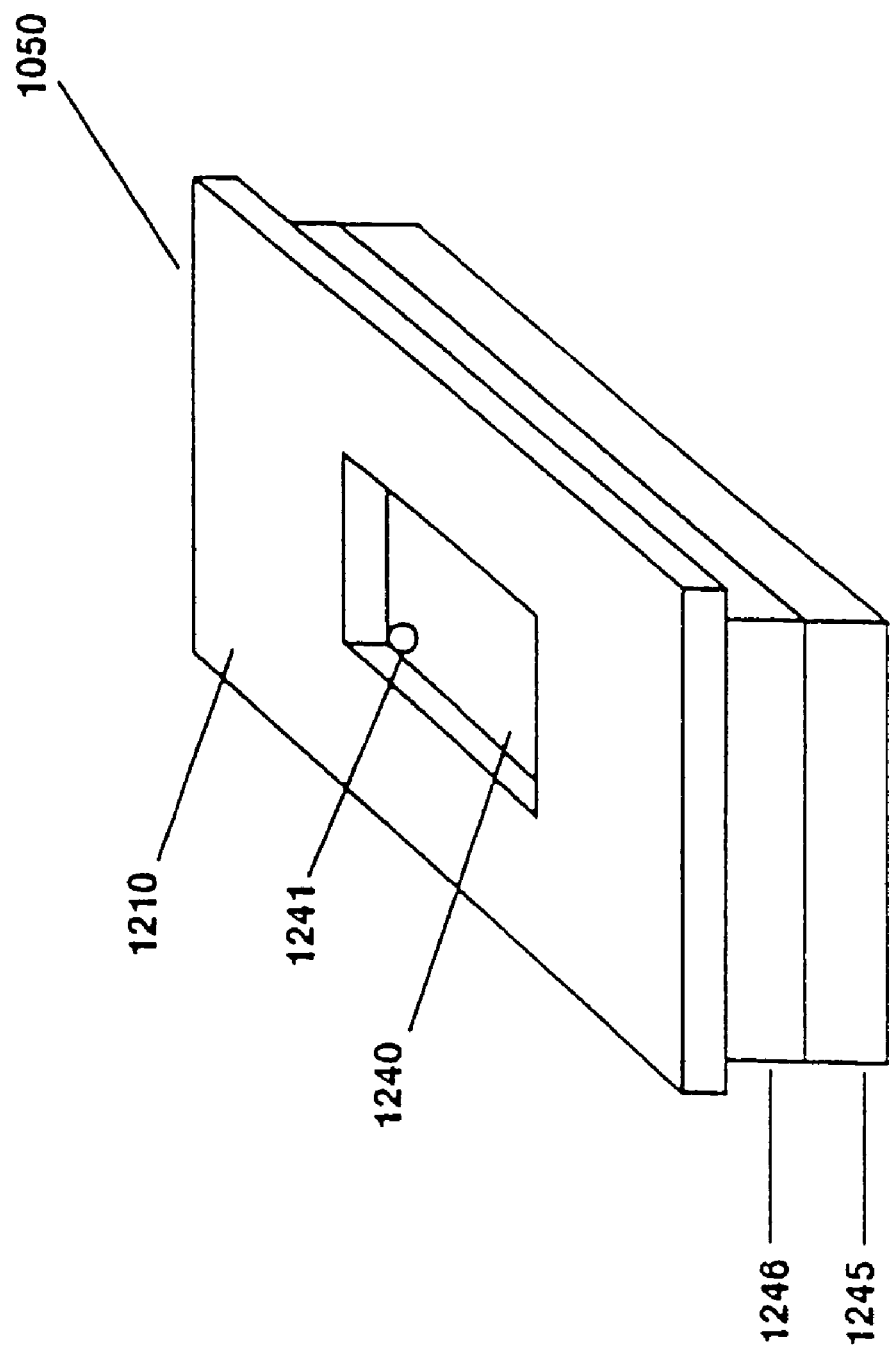

FIG. 12*a* shows table 1050 in greater detail. Table 1050 includes a substantially flat platform 1210 having a depression 1240 for holding a chip. In some embodiments, a port 1241 is provided in depression 1240. Port 1241 is connected to a vacuum pump which creates a vacuum in the depression for immobilizing the chip therein. Platform 1210 is mounted on a combination linear rotary stage 1246, which in some embodiments may be a model 26LR manufactured by DARDAL, and a single axis translation stage 1245, which may be a model CR2226HSE2 manufactured by DARDAL.

Figure 12B:
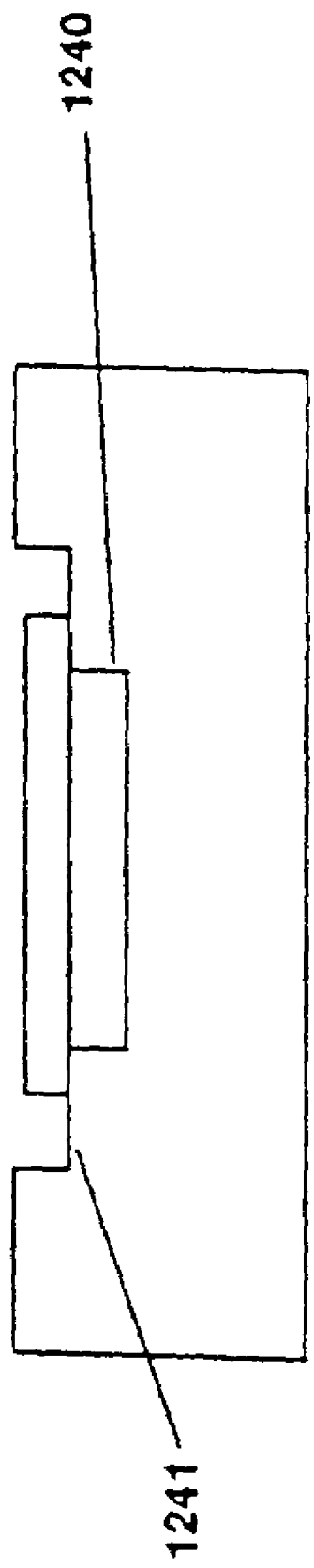

FIG. 12*b* illustrates depression 1240 in greater detail. As shown, a ledge 1241 surrounds the depression 1240. Ledge 1241 supports the chip when it is placed above depression 1240. Since the chips are placed over the depression with the probes facing the table, this design protects the probes from being potentially damaged during alignment.

Figure 13:
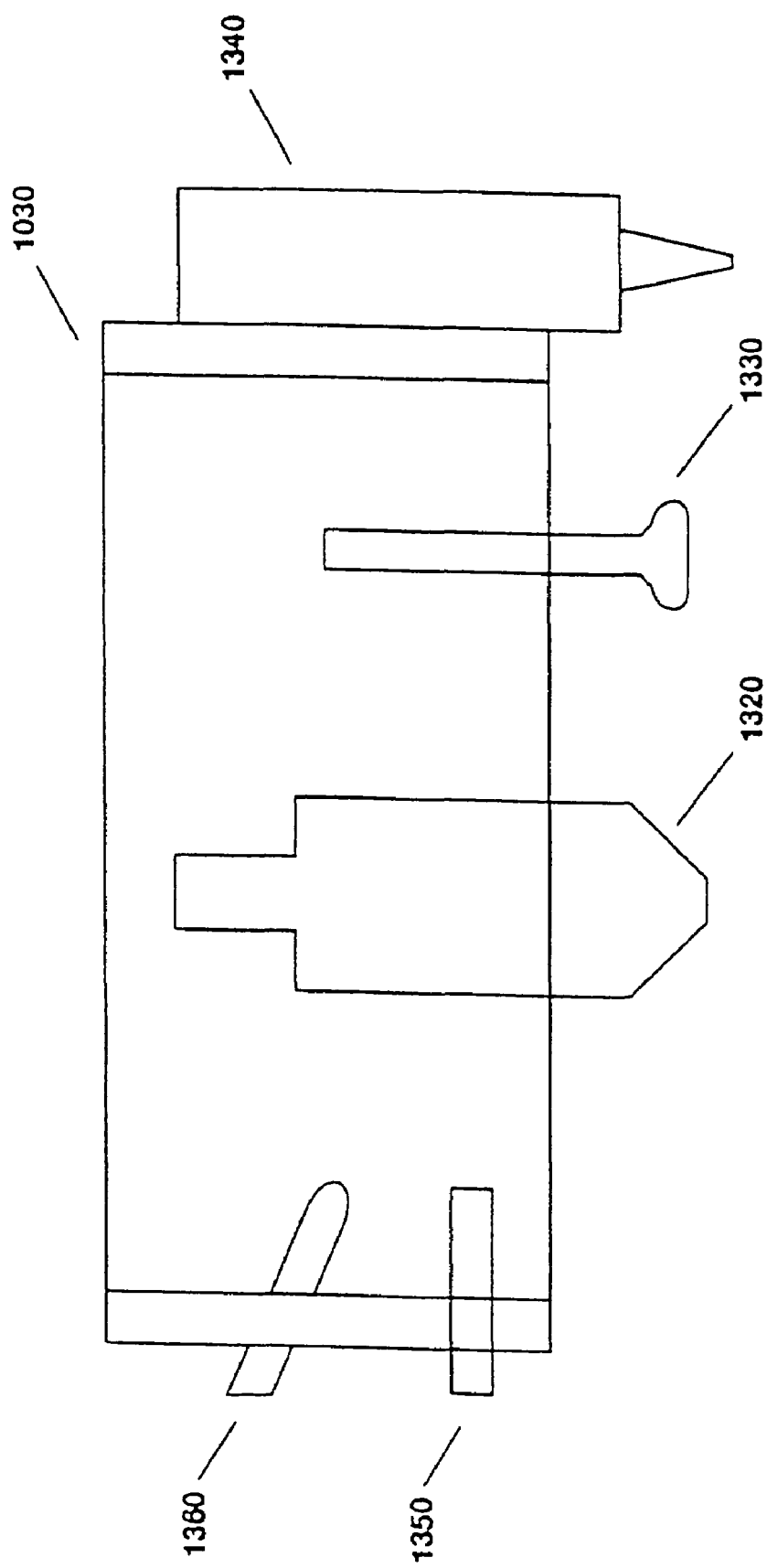

FIG. 13 illustrates the head unit 1030 in greater detail. As shown, the head unit 1030 includes a camera assembly 1320 that generates an output to a video display. A light 1360 is provided to enable the camera to focus and image an object of interest. The head unit also includes an ultraviolet light 1350 for curing the adhesive, a vacuum pickup 1330 for moving chip during the attachment process, and an adhesive dispenser 1340.

Figure 14A:
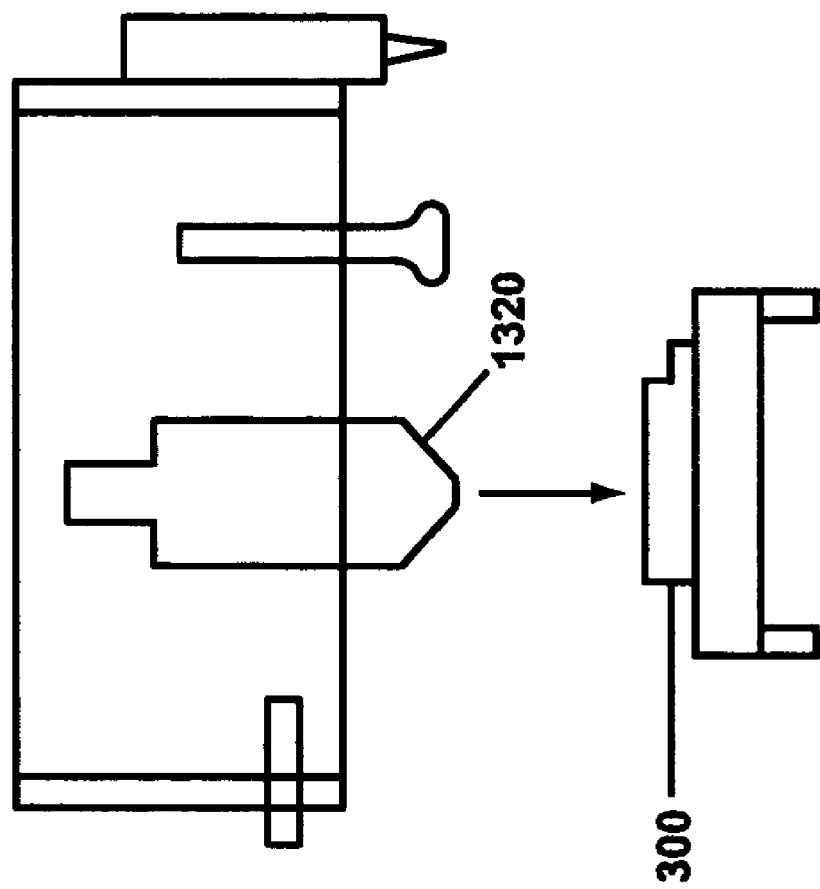
FIGS. 14a-14d illustrate the procedure for aligning the system of FIG. 10.
Figure 14B:
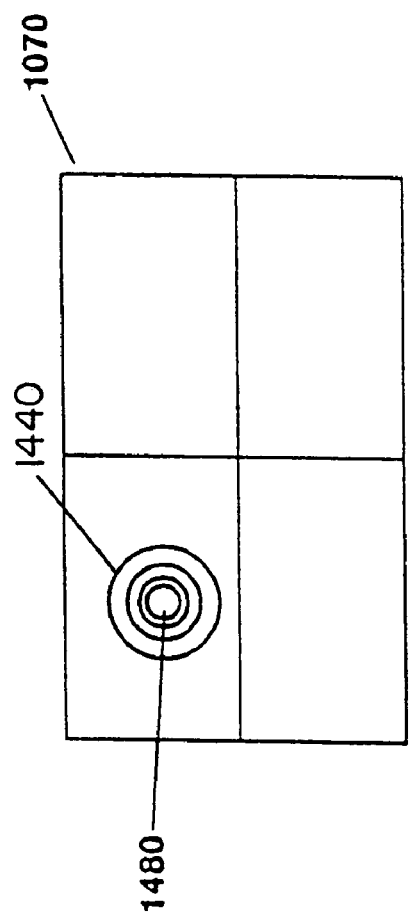
Figure 14C:
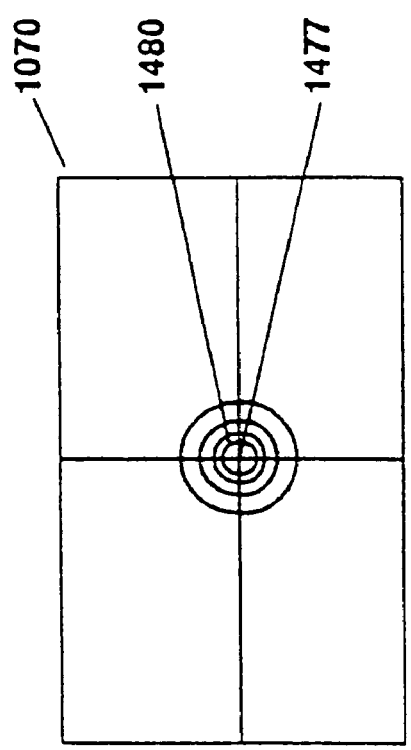
Figure 14D:
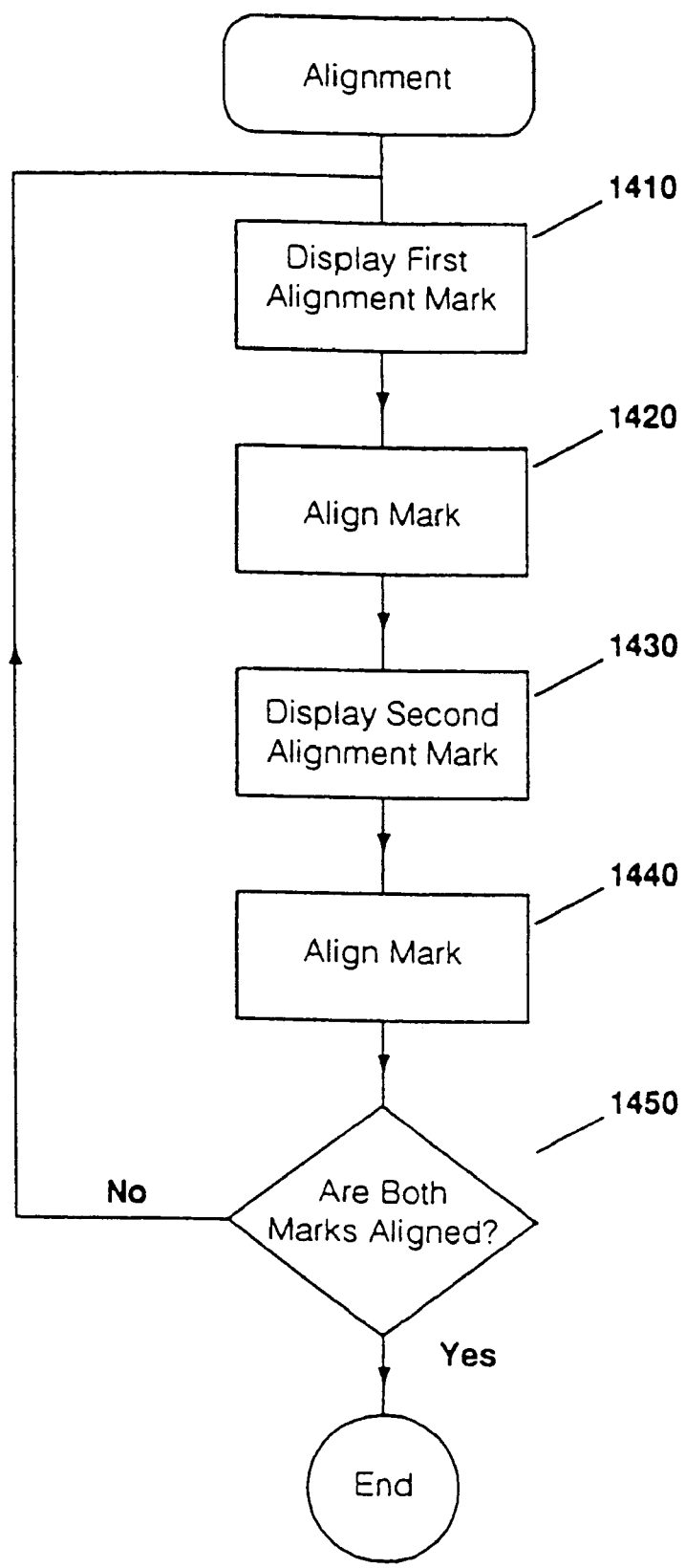

In operation, a chip package is placed onto table 1040. As previously described, the alignment pins on the table immobilize the package. The user begins the chip attachment process by calibrating the head unit. This may be done by moving the camera above the package and aligning it with a mark on the package, as shown in FIG. 14*a*. For convenience, one of the alignment pins may be used as an alignment mark. FIG. 14*b* illustrates a typical image 1440 generated by the camera during this step. As shown, the head unit is not aligned with pin 1480. To align the head unit, the user translates it in both the x and y direction until pin 1480 is located at the intersection 1477 of the cross hair on the video display, as illustrated in FIG. 14*c*.

Next, the chip is inserted into the depression on the chip alignment table. FIG. 14*c* is a flow chart indicating the steps for aligning the chip. At step 1410, the system positions the camera (head unit) above one of the chip's alignment marks. The camera images the alignment mark on the video display. At this point, the mark is normally misaligned (i.e., the mark is not located at the intersection of the cross hair alignment mark). At step 1420, the user adjusts the chip alignment table in both the x and y direction until the mark is substantially located at the intersection of the cross hair. Since no rotational adjustments were made, the mark may be misaligned angularly.

At step 1430, the user instructs the system to move the camera above a second alignment mark, which usually is at an opposite corner of the chip. Again, an image of the alignment mark is displayed. At this stage, the alignment mark is probably misaligned in the x, y, and angular directions. At step 1440, the user adjusts the rotational stage, x-stage, and y-stage, if necessary, to align the mark with the cross hair on the video display. In instances where the rotational stage has been rotated, the first alignment mark will become slightly misaligned. To compensate for this shift, the user repeats the alignment process beginning at step 1450 until both marks are aligned. Of course, image processing techniques may be applied for automated head unit and chip alignment.

Figure 15E:
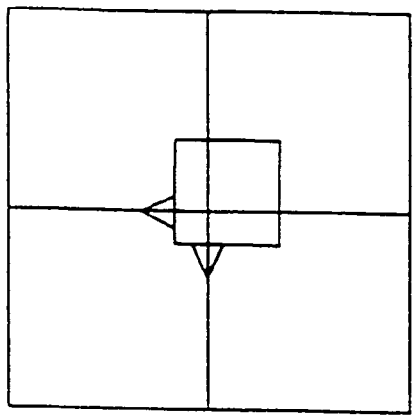
FIGS. 15a-15e illustrate images obtained during the alignment process of FIGS. 14a-14d.
Figure 15B:
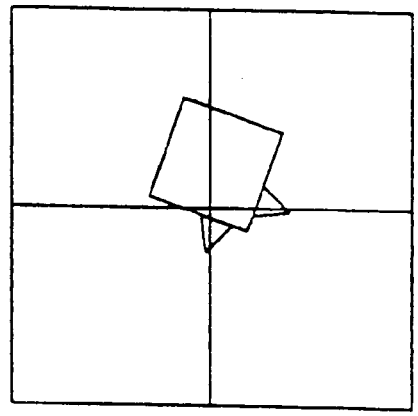
Figure 15D:
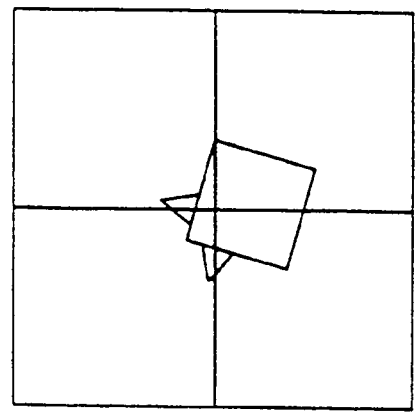
Figure 15A:
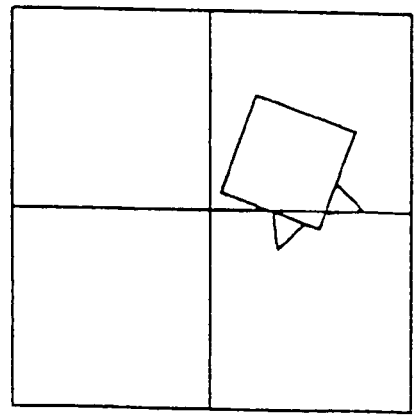
Figure 15C:
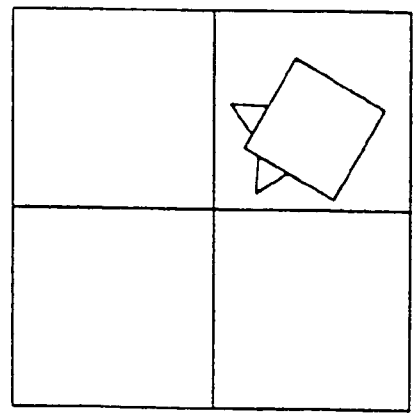

FIG. 15a is an example of an image displayed by the video screen during step 1410. As shown, the first alignment mark (lower left corner of the chip) is not aligned with the cross hair marking. FIG. 15b exemplifies an image of the first alignment mark after adjustments were made by the user. FIG. 15c illustrates a typical image displayed by video screen during step 1430. As illustrated, the second alignment mark (upper right corner of the chip) is misaligned in the x, y, and angular directions. FIG. 15d illustrates an image of the second mark following initial adjustments by the user at step 1440. FIG. 15e illustrates the orientation of the second alignment mark after the chip has been aligned.

Once the chip is aligned, the vacuum holding the chip on the attachment table is released. Thereafter, the pickup on the head unit removes the chip from the table and aligns it on the cavity of the package. In some embodiments, the chip is mated to the pickup by a vacuum.

Optionally, the user may check to ensure that the chip is correctly aligned on the cavity by examining the chip's alignment marks with the camera. If the chip is out of position, the chip is removed and realigned on the alignment table. If the chip is correctly positioned, the system deposits an adhesive by moving the dispenser along the trough surrounding the cavity. In some embodiments, the vacuum is released before depositing the adhesive in the trough. This step is merely precautionary and implemented to ensure that the vacuum does not cause any adhesive to seep into the cavity. Once the adhesive is deposited, the system reexamines the chip to determine if the adhesive had moved the chip out of position. If the chip is still aligned, the head unit locates the ultraviolet light above the adhesive and cures it for a time sufficient to harden the adhesive, which in one embodiment is about 10 seconds. Otherwise, the chip is realigned.

Upon completion, the chip package will have a variety of uses. For example, the chip package will be useful in sequencing genetic material by hybridization. In sequencing by hybridization, the chip package is mounted on a hybridization station where it is connected to a fluid delivery system. Such system is connected to the package by inserting needles into the ports and puncturing the septums therein. In this manner, various fluids are introduced into the cavity for contacting the probes during the hybridization process.

Usually, hybridization is performed by first exposing the sample with a prehybridization solution. Next, the sample is incubated under binding conditions with a solution containing targets for a suitable binding period. Binding conditions will vary depending on the application and are selected in accordance with the general binding methods known including those referred to in: Maniatis et al., *Molecular Cloning: A Laboratory Manual* (1989), 2nd Ed., Cold Spring Harbor, N.Y. and Berger and Kimmel, *Methods in Enzymology, Volume* 152, *Guide to Molecular Cloning Techniques* (1987), Academic Press, Inc., San Diego, Calif.; Young and Davis (1983) *Proc. Natl. Acad. Sci.* (*U.S.A.*) 80: 1194, which are incorporated herein by reference. In some embodiments, the solution may contain about 1 molar of salt and about 1 to 50 nanomolar of targets. Optionally, the fluid delivery system includes an agitator to improve mixing in the cavity, which shortens the incubation period. Finally, the sample is washed with a buffer, which may be 6× SSPE buffer, to remove the unbound targets. In some embodiments, the cavity is filled with the buffer after washing the sample.

Thereafter, the package may be aligned on a detection or imaging system, such as those disclosed in U.S. Pat. No. 5,143,854 (Pirrung et al.) or U.S. patent application Ser. No. 08/495,889 already incorporated herein by reference for all purposes. Such detection systems may take advantage of the package's asymmetry (i.e., non-flush edge) by employing a holder to match the shape of the package specifically. Thus, the package is assured of being properly oriented and aligned for scanning. The imaging systems are capable of qualitatively analyzing the reaction between the probes and targets. Based on this analysis, sequence information of the targets is extracted.

IV. DETAILS ON ALTERNATIVE EMBODIMENTS a. Chip Package Orientation

Figure 16A:
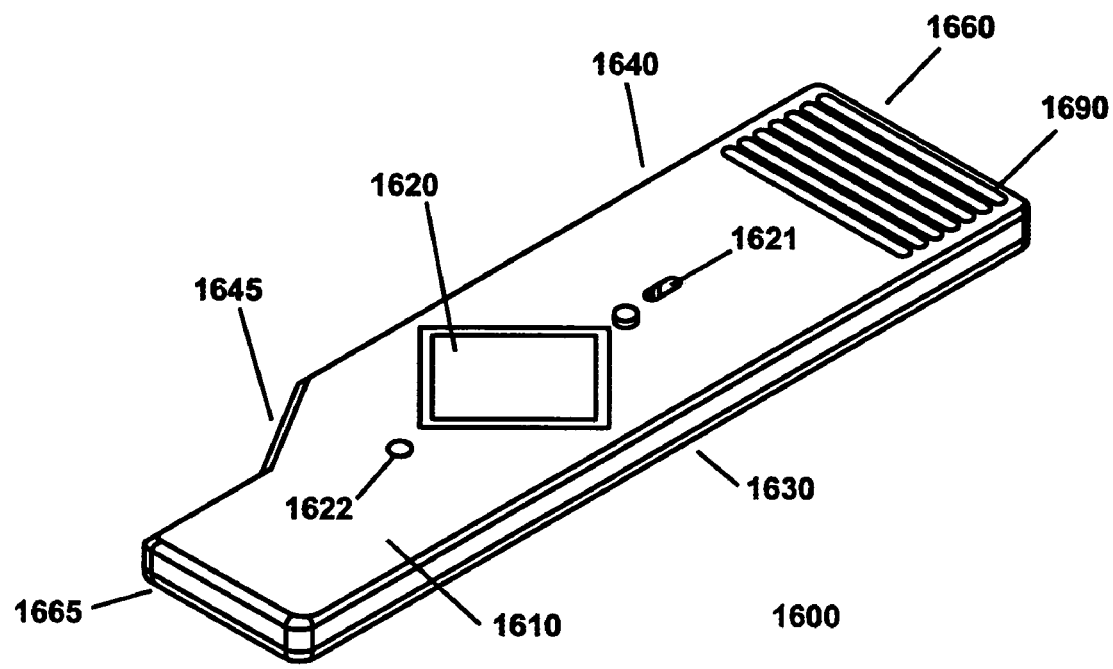
FIGS. 16a-16b illustrate an alternative embodiment of a packaging device.
Figure 16B:
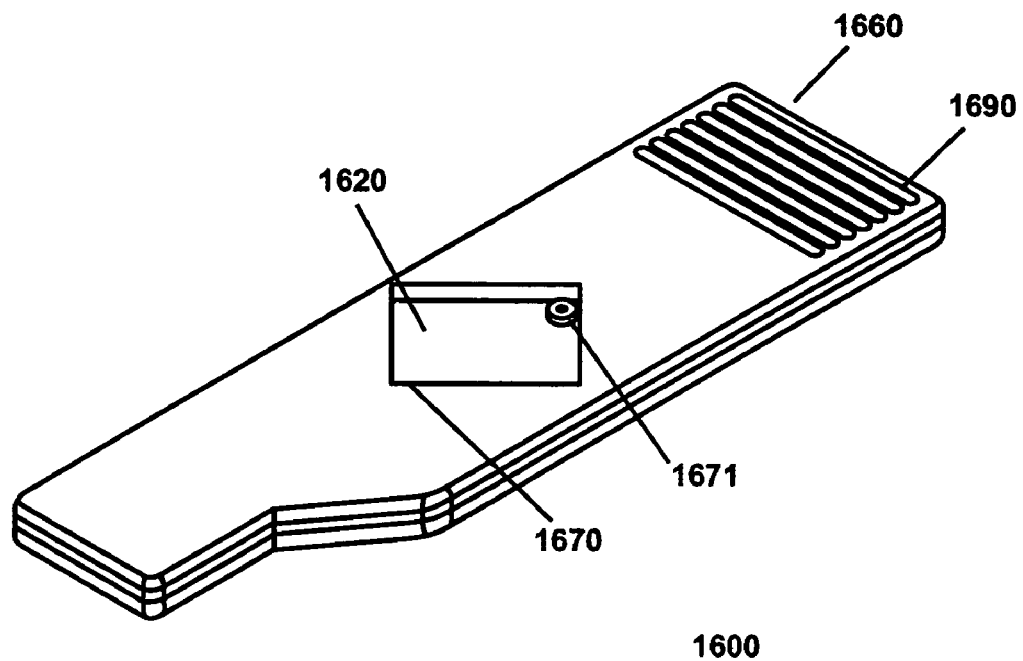

FIGS. 16a-16b illustrate an alternative embodiment of the package. FIG. 16a shows a top view and FIG. 16b shows a bottom view. As shown in FIG. 16a, a cavity 1620 is located on a top surface 1610 of the package body 1600. The body includes alignment holes 1621 and 1622 that are used, for example, in mating the chip to the package. Optionally, a plurality of ridges 1690 is located at end 1660 of the body. The friction created by ridges 1690 allows the package to be handled easily without slippage.

The body also includes two substantially parallel edges 1630 and 1640. As shown, edge 1640 is narrowed at end 1665 to create an uneven edge 1645. The asymmetrical design of the body facilitates correct orientation when mounted onto detection systems. For example, detection systems may contain a holder, similar to that of an audio cassette tape, in which end 1665 is inserted.

Referring to FIG. 16b, ports 1670 and 1671 communicate with cavity 1620. A seal is provided for each port to retain fluids in the cavity. Similar to the top surface, the bottom surface may optionally include a plurality of ridges 1690 at end 1660.

Figure 17B:
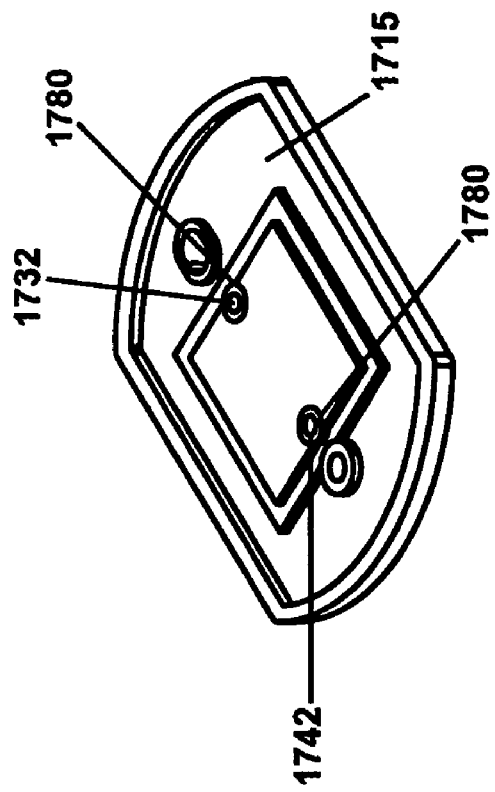
FIGS. 17a-17b illustrate another embodiment of a packaging device.
Figure 17A:
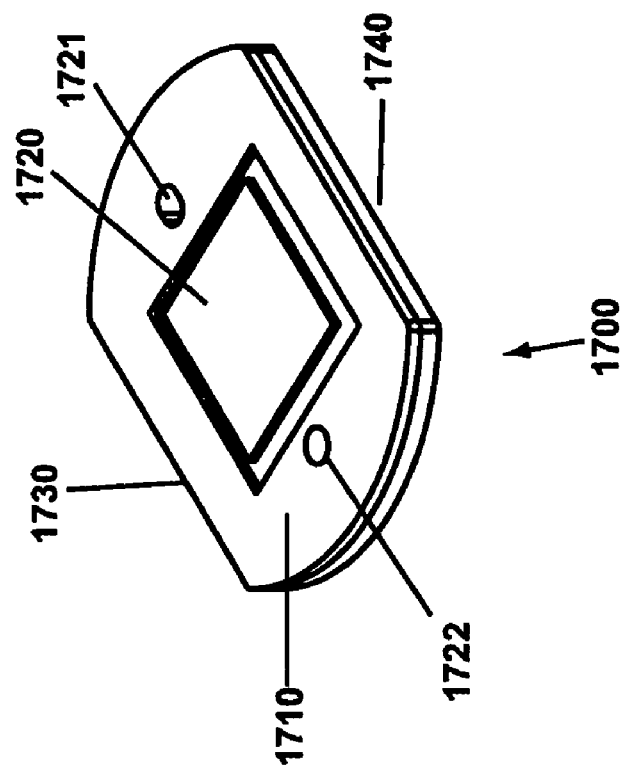

FIGS. 17a-17b illustrate an alternative embodiment of the package. FIG. 17a shows a top view and FIG. 17b shows a bottom view. Referring to FIG. 17a, a cavity 1720 is located on a top surface 1710 of the package body 1700. The body may be formed in the shape of a disk with two substantially parallel edges 1730 and 1740. Alignment holes 1721 and 1722, which may be different in size or shape, are located on the body. In some embodiments, the package is inserted like an audio cassette tape into detection systems in a direction parallel to edges 1730 and 1740. Edges 1730 and 1740 and alignment holes prevent the package from being inserted incorrectly into the detection systems.

As shown in FIG. 17b, ports 1730 and 1740 are located on the bottom surface 1715 of the package. Ports 1730 and 1740 communicate with cavity 1720 and each include a seal 1780 for sealing fluids in the cavity.

b. Chip Attachment

Figure 18:
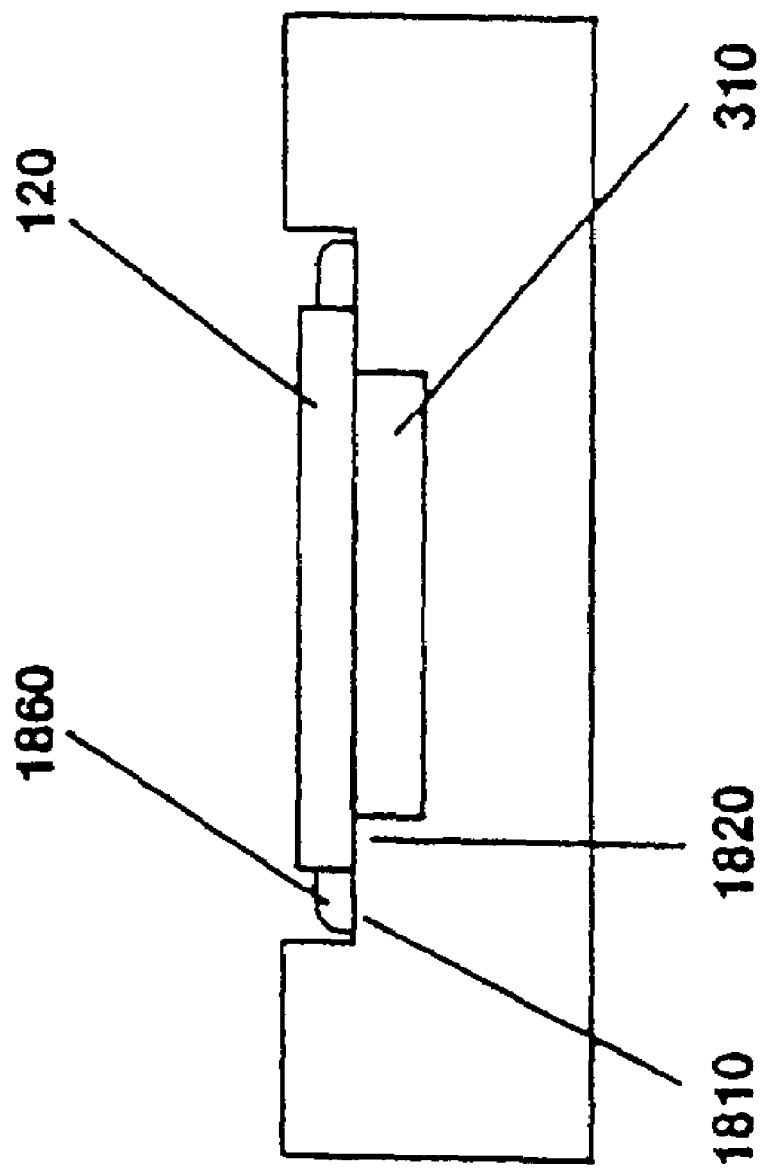
FIG. 18 illustrates an alternative embodiment for attaching the chip to the packaging device.

FIG. 18 illustrates an alternative embodiment for attaching the chip to the package. As shown, two concentric ledges 1810 and 1820 surround the perimeter of cavity 310. Ledge 1820 supports the chip 120 when mounted above cavity 310. Ledge 1810, which extends beyond chip 120, receives an adhesive 1860 such as ultraviolet cured silicone, cement, or other adhesive for attaching the chip thereto.

FIG. 19 illustrates another embodiment for attaching the chip to the package. According to this embodiment, a ledge 1910 is formed around cavity 310. Preferably, the ledge is sufficiently large to accommodate an adhesive 1920 such as an adhesive film, adhesive layer, tape, or any other adhesive layer. Chip 120 attaches to the package when it contacts the adhesive film.

Figure 20A:
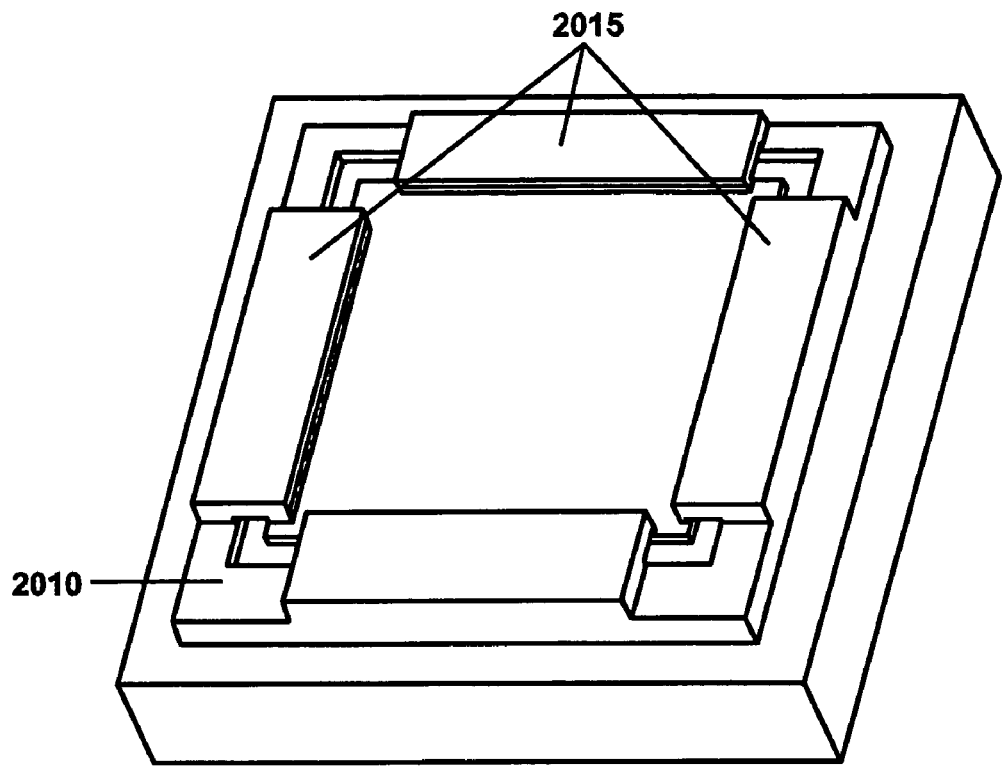
FIGS. 20a-20b illustrate yet another embodiment for attaching the chip to the packaging device.
Figure 20B:
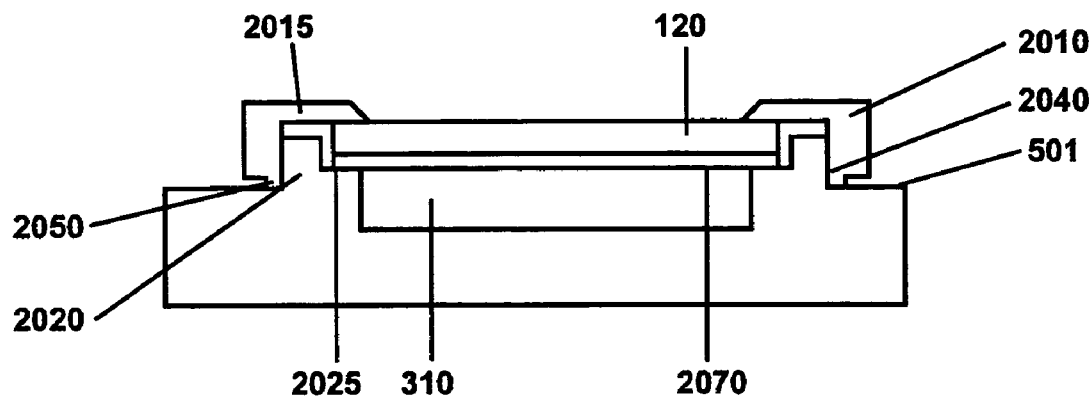

FIG. 20a illustrates yet another embodiment for attaching a chip to the package. As shown, a clamp 2010, such as a frame having a plurality of fingers 2015, attaches the chip to the package. FIG. 20b illustrates a cross sectional view. A ridge 2020 on surface 501 surrounds cavity 310. The ridge includes a ledge 2025 upon which chip 120 rests. Optionally, a gasket or a seal 2070 is located between the ledge and chip to ensure a tight seal around cavity 310. Clamp 2010 is attached to side 2040 of ridge 2020 and surface 501. In some embodiments, clamp 2010 is acoustically welded to the body. Accordingly, clamp 2010 includes energy directors 2050 located at its bottom. Alternatively, screws, clips, adhesives, or other attachment techniques may be used to mate clamp 2010 to the package. When mated, fingers 2015 secure chip 120 to the package.

Figure 21:
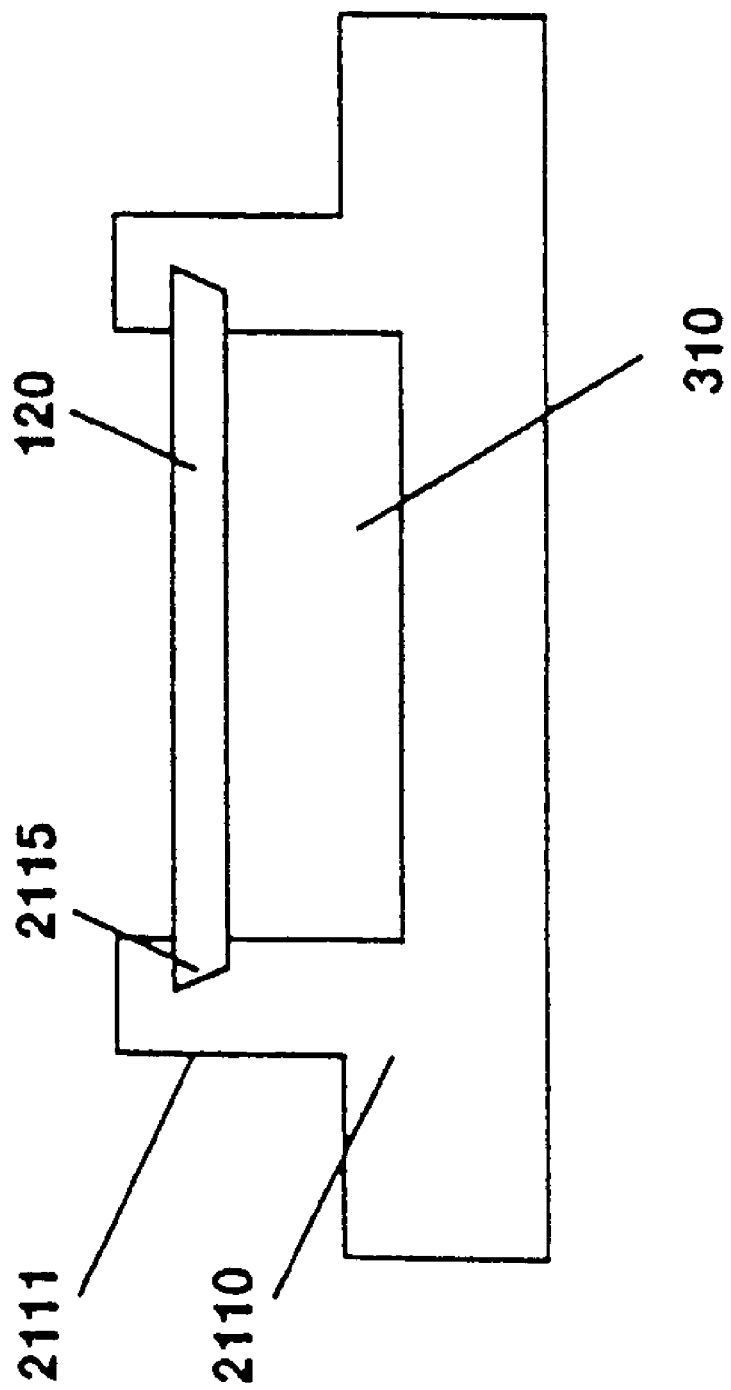
FIG. 21 illustrates an alternative embodiment for attaching the chip to the packaging device.

FIG. 21 illustrates an alternative embodiment for attaching the chip to the package. A ridge 2110, having a notch 2115 at or near the top of ridge 2110, encompasses the cavity 310. Chip 120 is wedged and held into position by notch 2115. Thereafter, a process known as heat staking is used to mount the chip. Heat staking includes applying heat and force at side 2111 of ridge, thus forcing ridge tightly against or around chip 120.

Figure 22:
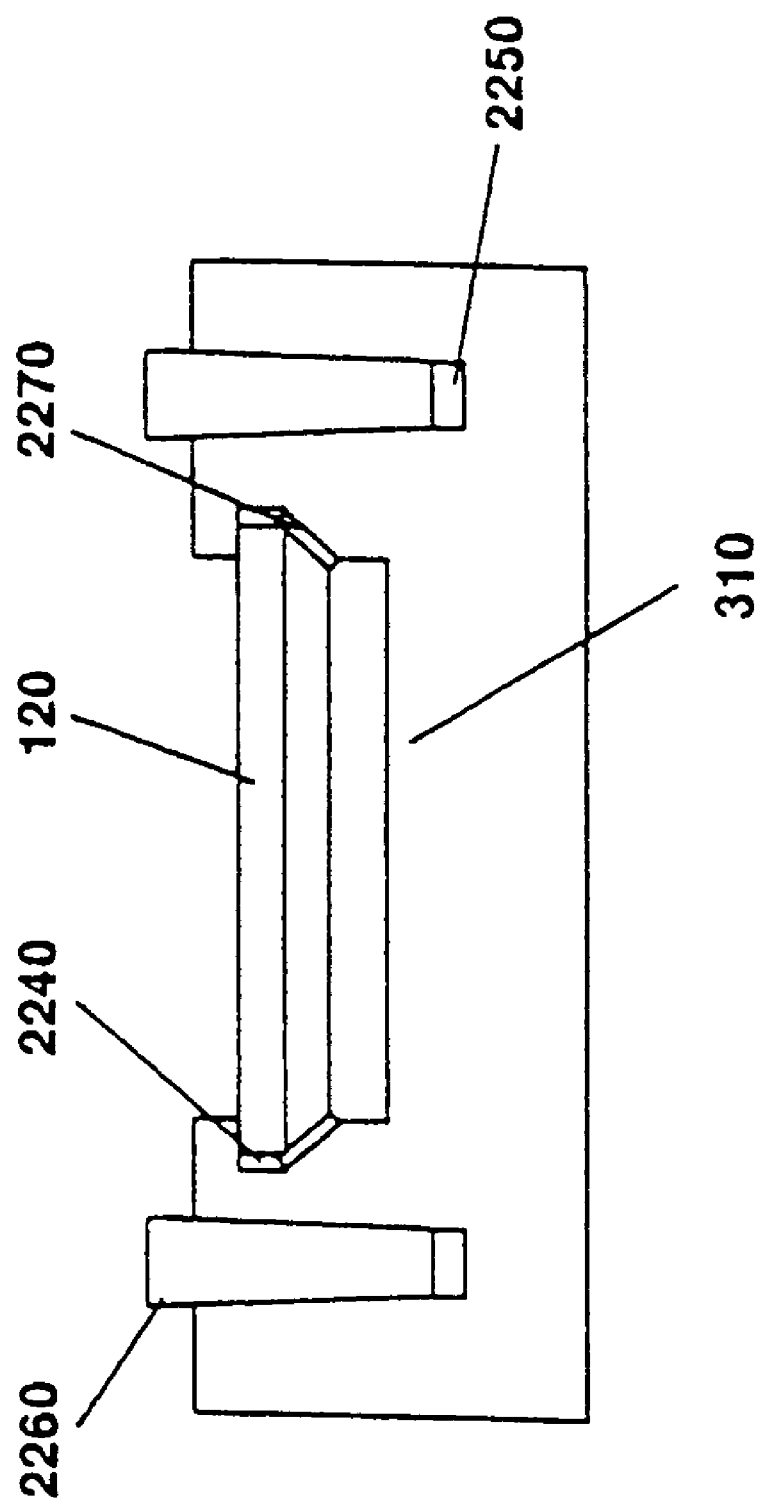
FIG. 22 illustrates another embodiment for attaching the chip to the packaging device.

FIG. 22 shows another embodiment of attaching a chip onto a package. As shown, a channel 2250 surrounds cavity 310. A notch 2240 for receiving the chip 120 is formed along or near the top of the cavity 310. In some embodiments, a gasket or seal 2270 is placed at the bottom of the notch to ensure a tight seal when the chip is attached. Once the chip is located at the notch, a V-shaped wedge 2260 is inserted into channel 2250. The wedge forces the body to press against chip's edges and seal 2260, thus mating the chip to the package. This process is known as compression sealing.

Other techniques such as insert molding, wave soldering, surface diffusion, laser welding, shrink wrap, o-ring seal, surface etching, or heat staking from the top may also be employed.

c. Fluid Retention

Figure 23:
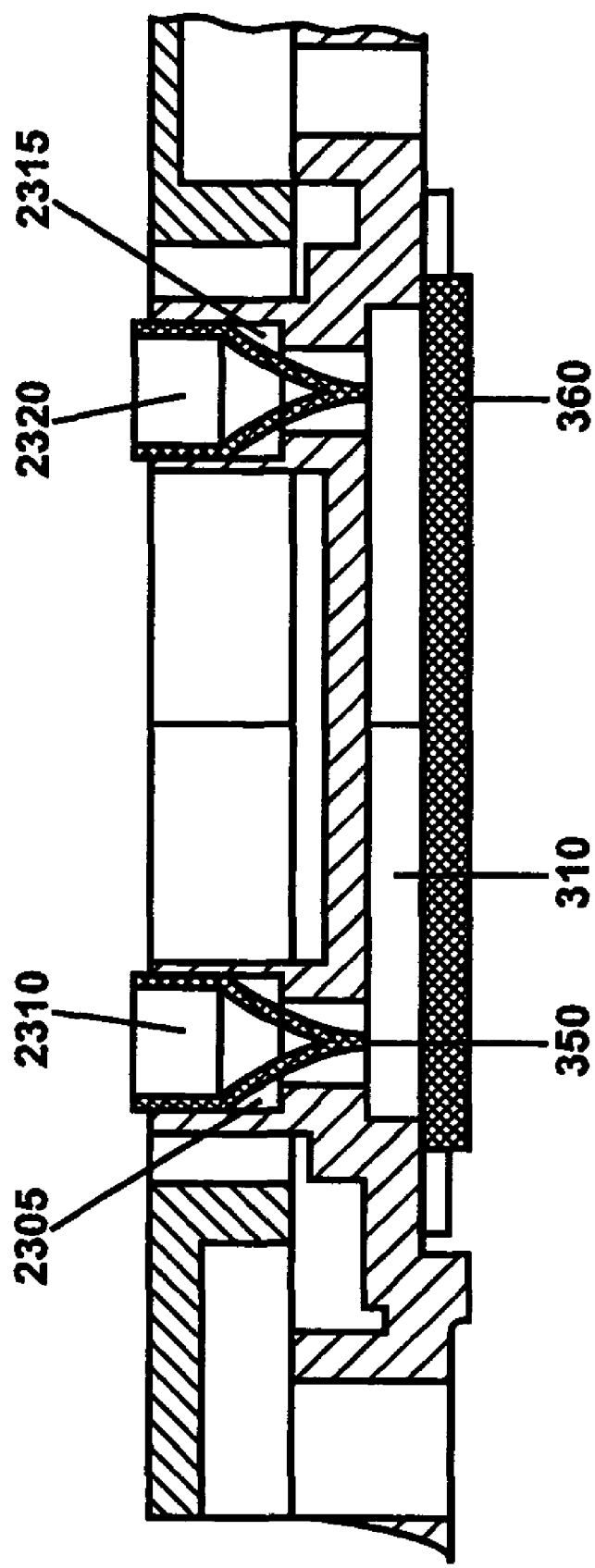
FIG. 23 illustrates an alternative embodiment for sealing the cavity on the packaging device.

FIG. 23 shows an alternative embodiment of package that employs check valves to seal the inlets. As shown, depressions 2305 and 2315 communicate with cavity 310 through inlets 350 and 360. Check valves 2310 and 2320, which in some embodiments may be duck-billed check valves, are seated in depressions 2305 and 2315. To introduce a fluid into the cavity, a needle is inserted into the check valve. When the needle is removed, the check valve reseals itself to prevent leakage of the fluid.

Figure 24:
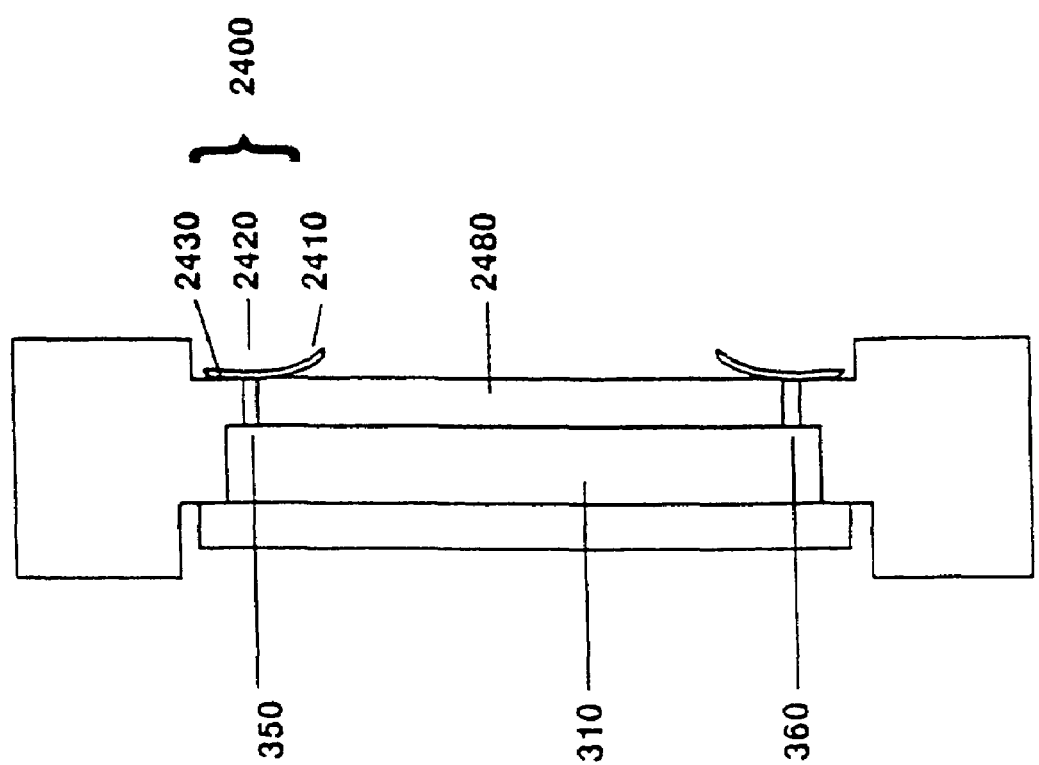
FIG. 24 illustrates another alternative embodiment for sealing the cavity on the packaging device.

FIG. 24 illustrates another package that uses reusable tape for sealing the cavity 310. As shown, a tape 2400 is located above inlets 350 and 360. Preferably, end 2430 of tape is permanently fixed to surface 2480 while end 2410 remains unattached. The mid section 2420 of the tape is comprised of non-permanent adhesive. This design allows inlets to be conveniently sealed or unsealed without completely separating the tape from the package.

Figure 25:
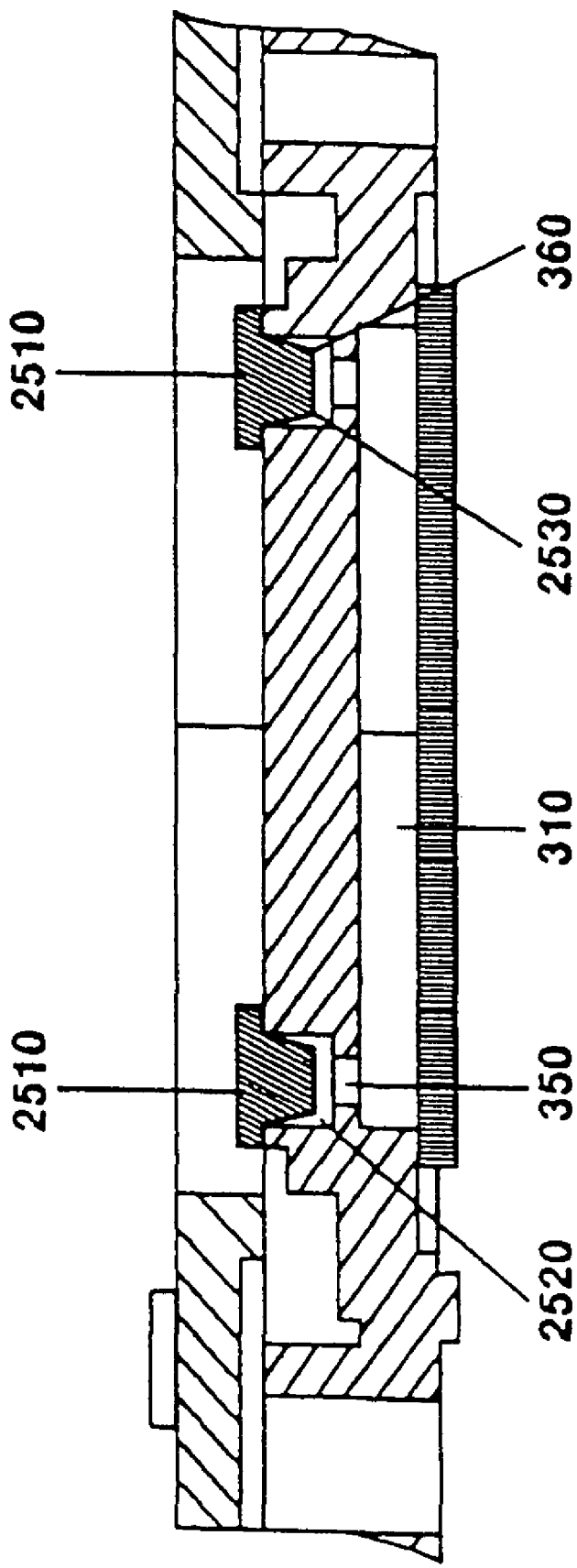
FIG. 25 illustrates yet another embodiment for sealing the cavity on the packaging device.

FIG. 25 illustrates yet another embodiment of the package that uses plugs to retain fluids within the cavity. As shown, depressions 2520 and 2530 communicate with cavity 310 via inlets 350 and 360. A plug 2510, which in some embodiment may be composed of rubber or other sealing material, is mated to each of the depressions. Plugs 2510 are easily inserted or removed for sealing and unsealing the cavity during the hybridization process.

Figure 26A:
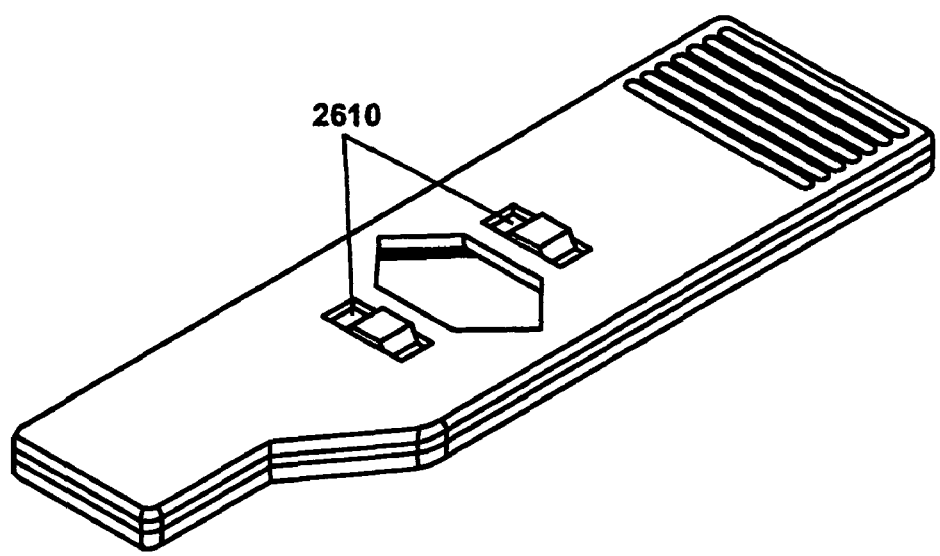
FIGS. 26a-26b illustrate an alternative embodiment for sealing the cavity on the packaging device.
Figure 26B:
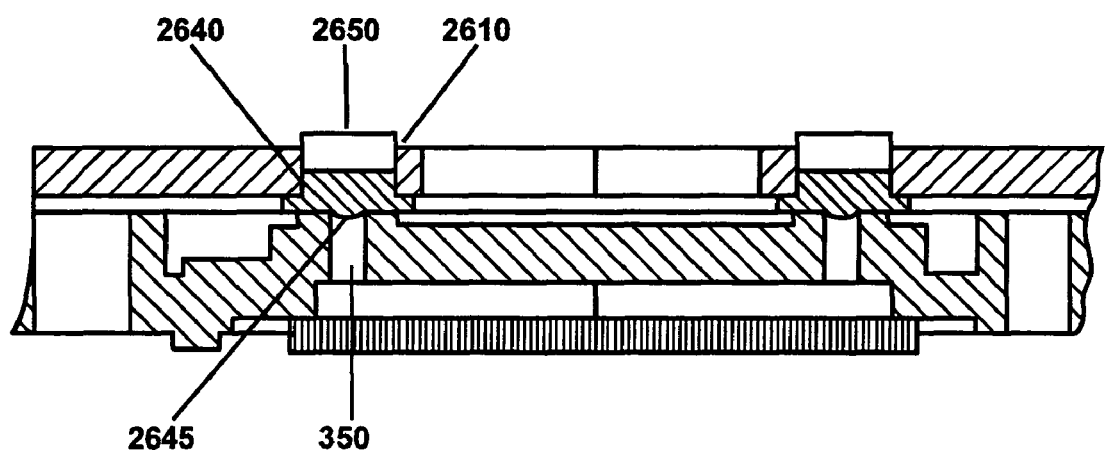

FIG. 26a illustrates a package utilizing sliding seals for retaining fluids within the cavity. The seals are positioned in slots 2610 that are located above the inlets. The slots act as runners for guiding the seals to and from the inlets. FIG. 26b illustrates the seal in greater detail. Seal 2640, which may be composed of rubber, teflon rubber, or other sealing material, is mated to each slot 2610. The seal includes a handle 2650 which extends through the slot. Optionally, the bottom of the seal includes an annular protrusion 2645 to ensure mating with inlet 350. The inlet is sealed or unsealed by positioning the seal appropriately along the slot. Alternatively, spring loaded balls, rotary ball valves, plug valves, or other fluid retention techniques may be employed.

d. Chip Orientation

Figure 27B:
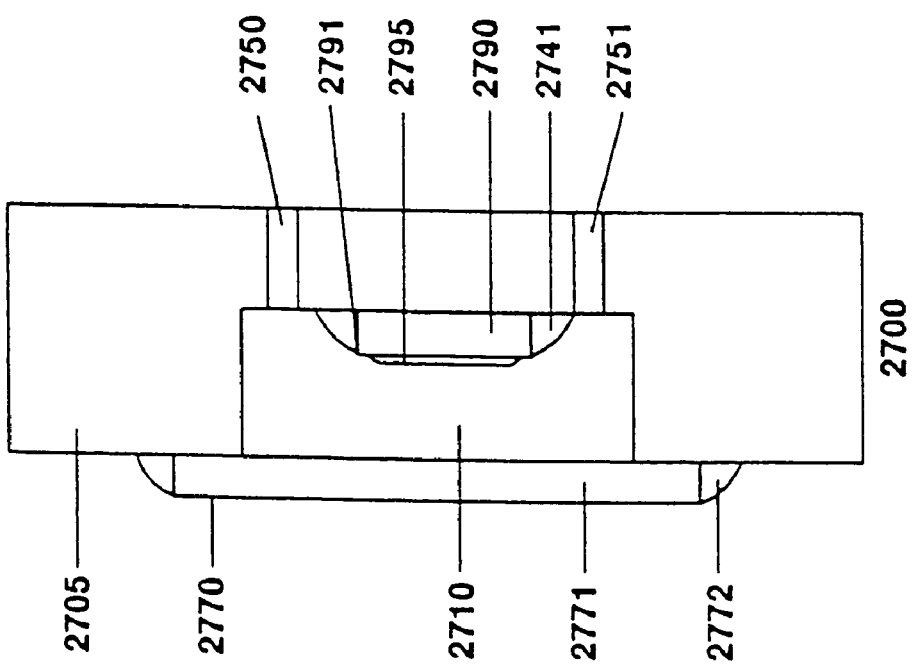
FIGS. 27a-27b illustrate an alternative embodiment for mounting the chip.
Figure 27A:
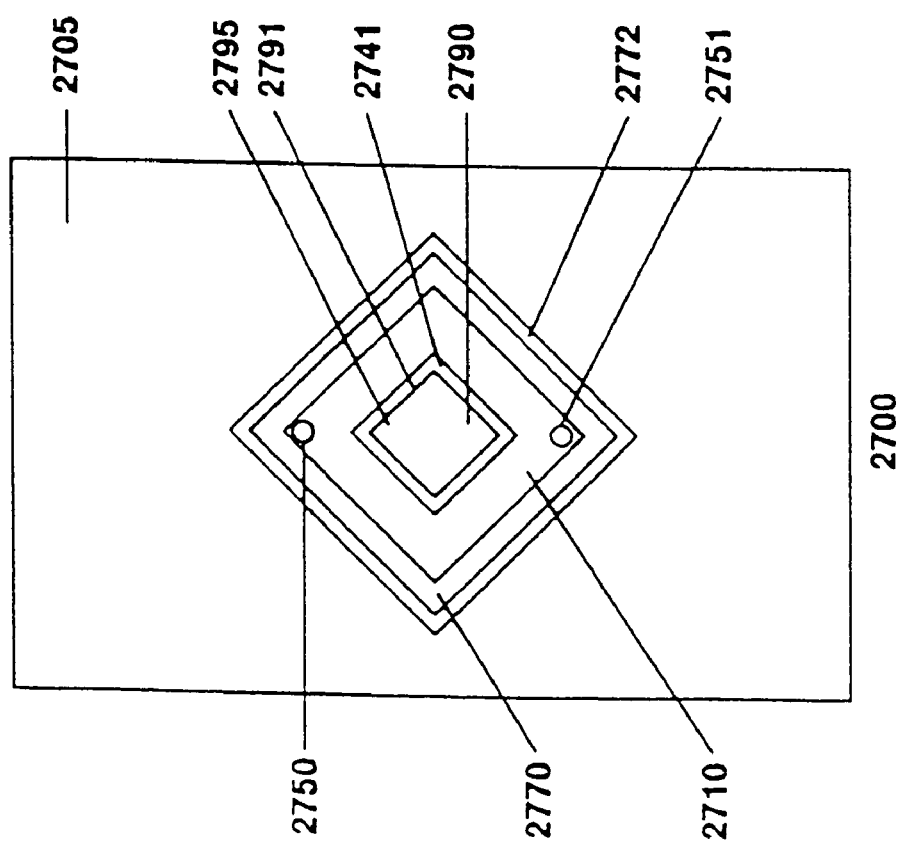

FIGS. 27a-27b illustrate an alternative embodiment of the package. FIG. 27a illustrates a top view and FIG. 27b shows a cross sectional view. As shown, package 2700 includes a cavity 2710 on a surface 2705. A chip 2790 having an array of probes 2795 on surface 2791 is mated to the bottom of cavity 2710 with an adhesive 2741. The adhesive, for example, may be silicone, adhesive tape, or other adhesive. Alternatively, clips or other mounting techniques may be employed. Optionally, the bottom of the cavity may include a depression in which a chip is seated.

This configuration provides several advantages such as: 1) permitting the use of any type of substrate (i.e., non-transparent or non-translucent), 2) yielding more chips per wafer since the chip does not require an edge for mounting, and 3) allowing chips of various sizes or multiple chips to be mated to the package.

A cover 2770 is mated to the package for sealing the cavity. Preferably, cover 2770 is composed of a transparent or translucent material such as glass, acrylic, or other material that is penetrable by light. Cover 2270 may be mated to surface 2705 with an adhesive 2772, which in some embodiments may be silicone, adhesive film, or other adhesive. Optionally, a depression may be formed around the cavity such that surface 2271 of the cover is at least flush with surface 2705. Alternatively, the cover may be mated to surface 2705 according to any of the chip attachment techniques described herein.

Inlets 2750 and 2751 are provided and communicate with cavity 2710. Selected fluids are circulated through the cavity via inlets 2750 and 2751. To seal the fluids in the cavity, a septum, plug, or other seal may be employed. In alternative embodiments, any of the fluid retention techniques described herein may be utilized.

e. Parallel Hybridization and Diagnostics

In an alternative embodiment, the body is configured with a plurality of cavities. The cavities, for example, may be in a 96-well micro-titre format. In some embodiments, a chip is mounted individually to each cavity according to the methods described above. Alternatively, the probe arrays may be formed on the wafer in a format matching that of the cavities. Accordingly, separating the wafer is not necessary before attaching the probe arrays to the package. This format provides significant increased throughput by enabling parallel testing of a plurality of samples.

V. DETAILS OF AN AGITATION SYSTEM

Figure 28:
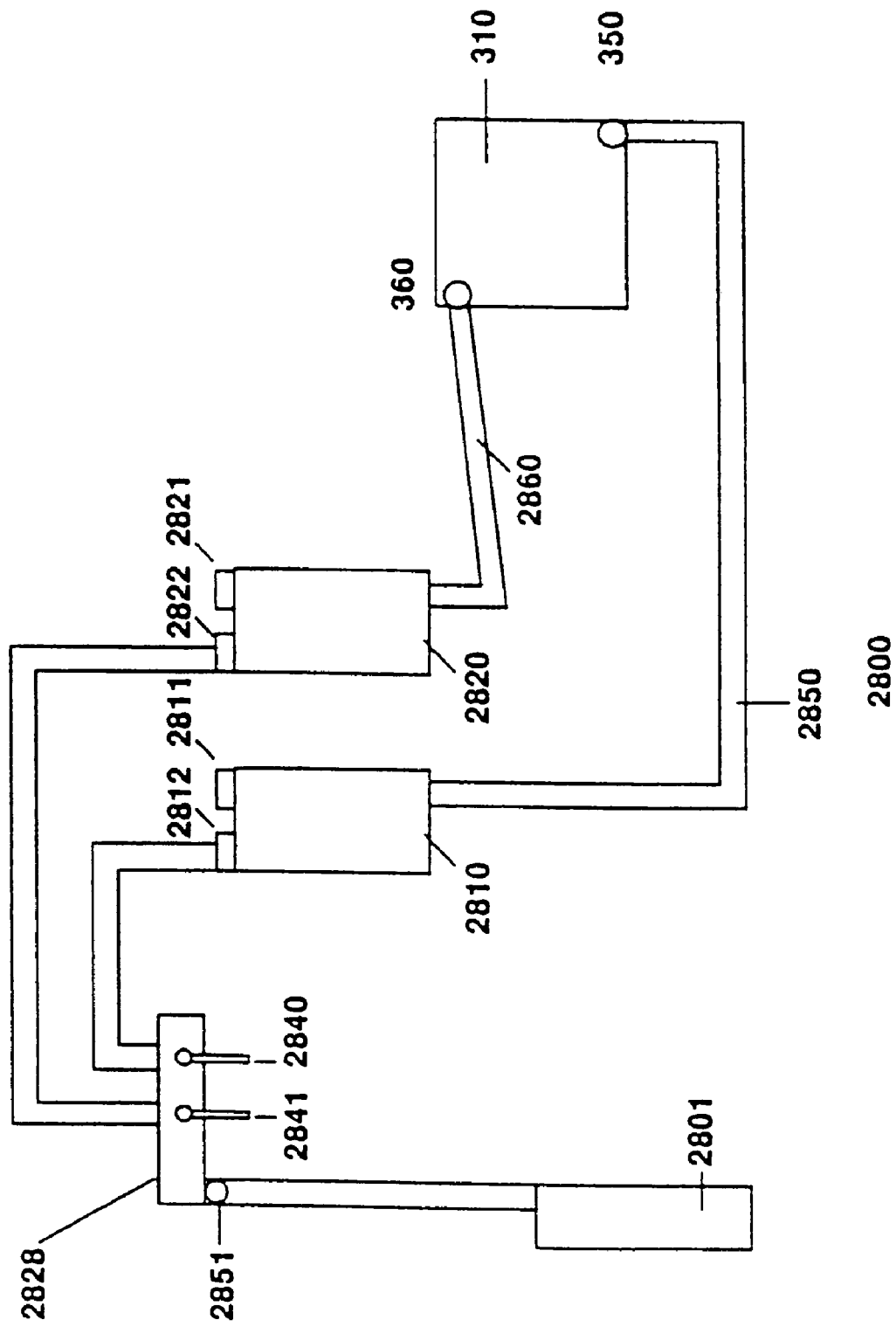
FIG. 28 illustrates an agitation system.

FIG. 28 illustrates an agitation system in detail. As shown, the agitation system 2800 includes two liquid containers 2810 and 2820, which in the some embodiments are about 10 milliliters each. Container 2810 communicates with port 350 via tube 2850 and container 2820 communicates with port 360 via tube 2860. An inlet port 2812 and a vent port 2811 are located at or near the top of container 2810. Container 2820 also includes an inlet port 2822 and a vent 2821 at or near its top. Port 2812 of container 2810 and port 2822 of container 2820 are both connected to a valve assembly 2828 via valves 2840 and 2841. An agitator 2801, which may be a nitrogen gas (N$_2$) or other gas, is connected to valve assembly 2828 by fitting 2851. Valves 2840 and 2841 regulate the flow of N$_2$ into their respective containers. In some embodiments, additional containers (not shown) may be provided, similar to container 2810, for introducing a buffer and/or other fluid into the cavity.

In operation, a fluid is placed into container 2810. The fluid, for example, may contain targets that are to be hybridized with probes on the chip. Container 2810 is sealed by closing port 2811 while container 2820 is vented by opening port 282 1. Next, N$_2$ is injected into container 2810, forcing the fluid through tube 2850, cavity 310, and finally into container 2820. The bubbles formed by the N$_2$ agitate the fluid as it circulates through the system. When the amount of fluid in container 2810 nears empty, the system reverses the flow of the fluid by closing valve 2840 and port 2821 and opening valve 2841 and port 2811. This cycle is repeated until the reaction between the probes and targets is completed.

In some applications, foaming may occur when N$_2$ interacts with the fluid. Foaming potentially inhibits the flow of the fluid through the system. To alleviate this problem, a detergent such as CTAB may be added to the fluid. In one embodiment, the amount of CTAB added is about 1 millimolar. Additionally, the CTAB affects the probes and targets positively by increasing the rate at which they bind, thus decreasing the reaction time required.

The system described in FIG. 28 may be operated in an alternative manner. According to this technique, back pressure formed in the second container is used to reverse the flow of the solution. In operation, the fluid is placed in container 2810 and both ports 2811 and 2821 are closed. As N$_2$ is injected into container 2810, the fluid is forced through tube 2850, cavity 310, and finally into container 2820. Because the vent port in container 2820 is closed, the pressure therein begins to build as the volume of fluid and N2 increases. When the amount of fluid in container 2810 nears empty, the flow of N$_2$ into container 2810 is terminated by closing valve 2840. Next, the circulatory system is vented by opening port 2811 of container 2810. As a result, the pressure in container 2820 forces the solution back through the system toward container 2810. In one embodiment, the system is injected with N$_2$ for about 3 seconds and vented for about 3 seconds. This cycle is repeated until hybridization between the probes and targets is completed.

Figure 29:
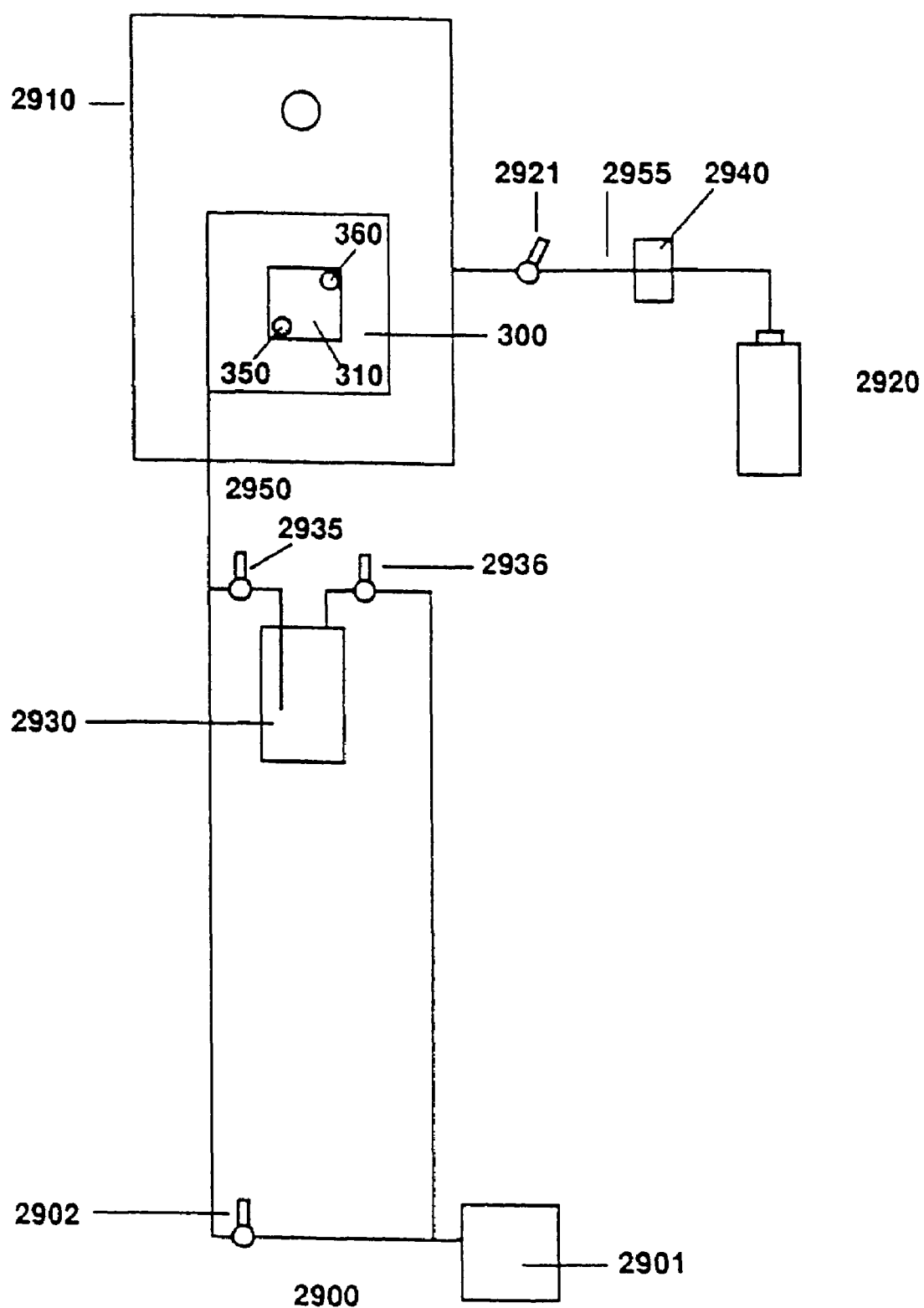
FIG. 29 illustrates an alternative embodiment of the agitation system.

FIG. 29 illustrates an alternative embodiment of the agitation system. System 2900 includes a vortexer 2910 on which the chip package 300 is mounted. A container 2930 for holding the fluid communicates with inlet 350 via tube 2950. A valve 2935 may be provided to control the flow of solution into the cavity. In some embodiments, circulator 2901, which may be a N$_2$ source or other gas source, is connected to container 2930. Alternatively, a pump or other fluid transfer device may be employed. The flow of N$_2$ into container 2930 is regulated by a valve 2936. Circulator 2901 is also connected to inlet tube 2950 via a valve 2902.

A waste container 2920 communicates with port 360 via outlet tube 2955. In one embodiment, a liquid sensor 2940 may be provided for sensing the presence of liquid in outlet tube 2955. Access to the waste container may be controlled by a valve 2921. Optionally, additional containers (not shown), similar to container 2930, may be employed for introducing a buffer or other fluid into the cavity.

The system is initialized by closing all valves and filling container 2930 with, for example, a fluid containing targets. Next, valves 2936, 2935, and 2955 are opened. This allows N$_2$ to enter container 2930 which forces the fluid to flow through tube 2950 and into the cavity. When the cavity is filled, valves 2935, 2936, and 2955 are closed to seal the fluid in the cavity. Next, the vortexer is activated to vibrate the chip package, similar to a paint mixer. In some embodiments, the vortexer may vibrate the package at about 3000 cycles per minutes. The motion mixes the targets in the fluid, shortening the incubation period. In some embodiments, the vortexer rotates the chip package until hybridization is completed. Upon completion, valve 2902 and 2955 are opened to allow N$_2$ into the cavity. The N$_2$ empties the fluid into waste container 2920. Subsequently, the cavity may be filled with a buffer or other fluid.

Figure 30:
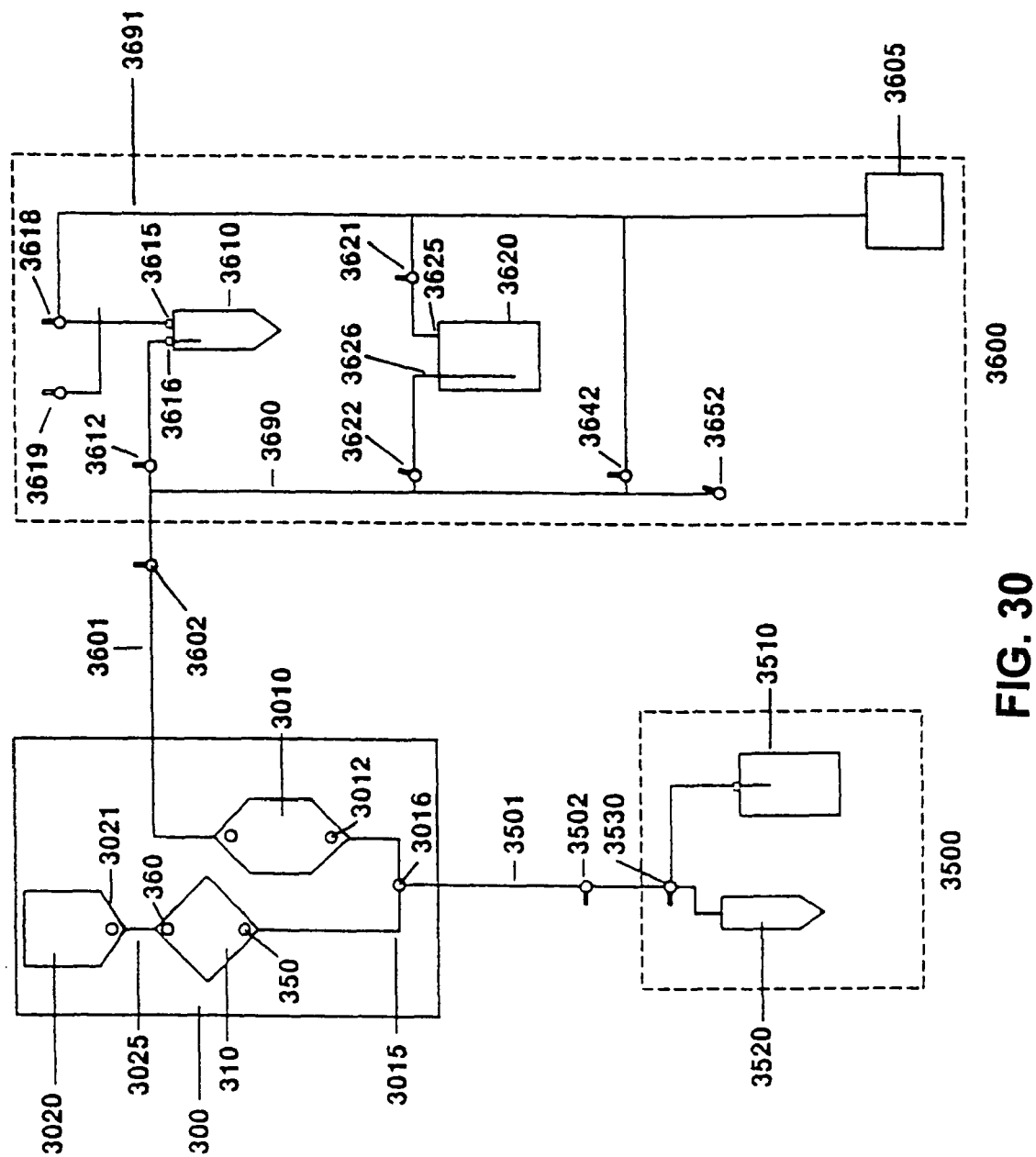
FIG. 30 illustrates another embodiment of the agitation system.

FIG. 30 illustrates an alternative embodiment in which the agitation system is partially integrated into the chip package. As shown, chip package 300 includes a cavity 310 on which the chip is mounted. Cavity 310 is provided with inlets 360 and 350. The package also includes chambers 3010 and 3020. A port 3021 is provided in chamber 3010 and is connected to inlet 360 by a channel 3025.

Chamber 3010 is equipped with ports 3011 and 3012. Port 3012 communicates with inlet 350 through a channel 3015. Channel 3015 is provided with a waste port 3016 that communicates with a fluid disposal system 3500 via a tube 3501. A valve 3502 regulates the flow of fluids into the disposal system. In some embodiments, the disposal system includes a waste container 3510 and fluid recovery container 3520 which are connected to tube 3501. A valve 3530 is provided to direct the flow of fluids into either the waste container or recovery container.

Port 3011 is coupled to a fluid delivery system 3600 through a tube 3601. Fluids flowing into chamber 3010 from the fluid delivery system are regulated by a valve 3602. The fluid delivery system includes fluid containers 3610 and 3620 that are interconnected with a tube 3690. Container 3610, which may hold a fluid containing targets, includes ports 3616 and 3615. Port 3616 is connected to tube 3690. A valve 3612 controls the flow of the fluid out of container 3610. A circulator 3605, which may be a N$_2$ source, is connected to port 3615 of container 3610. Alternatively, any type of gas, pump or other fluid transfer device may be employed. The flow of N$_2$ into container 3610 is controlled by a valve 3618. A valve 3619 may also be provided to vent container 3610.

Container 3620, which may hold a buffer, is provided with ports 3625 and 3626. Circulator 3605 is connected to port 3625. A valve 3621 is provided to control the flow of N$_2$ into container 3620. Port 3626 is connected to tube 3690 via a valve 3622. Valve 3622 regulates the flow of the buffer out of container 3620. Optionally, additional containers (not shown), similar to container 3620, may be configured for introducing other fluids into the cavity. A valve 3690 connects circulator 3605 to tube 3690 for controlling the flow of N$_2$ directly into the package. A valve 3652 is provided for venting the fluid delivery system.

In the initial operating state, all valves are shut. To start the hybridization process, a fluid containing targets is introduced into chamber 301 by opening valves 3602, 3612 and 3618. This injects N$_2$ into container 3610 which forces the fluid to flow through 3601 and into chamber 3010. When chamber 3010 is filled, valves 3612 and 3618 are closed. Next, valve 3642 is opened, allowing N$_2$ to flow directly into chamber 3010. The N$_2$ agitates and circulates the fluid into cavity 310 and out to chamber 3020. As the volume of fluid and N$_2$ in chamber 3020 increase, likewise does the pressure therein. When chamber 3020 approaches its capacity, valve 3642 is closed to stop the fluid flow. Thereafter, the system is vented by opening valve 3652. Venting the system allows the back pressure in chamber 3020 to reverse the flow of fluids back into chamber 3010. When chamber 3010 is filled, valve 3652 is closed and valve 3642 is opened to reverse the fluid flow. This cycle is repeated until hybridization is completed.

When hybridization is completed, the system may be drained. This procedure depends on which chamber the fluid is located in. If the fluid is located in chamber 3020, then valve 3502 is opened, while valve 3530 is positioned to direct the fluid into the appropriate container (recovery or waste). The pressure in chamber 3020 forces the fluid through port 3016, tube 3501, and into the disposal system. If the fluid is in chamber 3010, then valve 3502 and 3642 are opened. As a result, $N_2$ forces the fluid in chamber 3010 through port 3501 and into the disposal system.

Once the system is emptied, all valves are closed. A buffer or other fluid may be introduced into the cavity. For example, the cavity may be filled with a buffer by opening valves 3601, 3621, and 3622. This injects $N_2$ into container 3620 which forces the buffer therein to flow through the system until it fills cavity 310. In the alternative, ultrasonic radiation, heat, magnetic beads, or other agitation techniques may be employed.

The present inventions provide commercially feasible devices for packaging a probe chip. It is to be understood that the above description is intended to be illustrative and not restrictive. Many embodiments will be apparent to those skilled in the art upon reviewing the above description. Merely as an example, the package may be molded or machined from a single piece of material instead of two. Also, other asymmetrical designs may be employed to orient the package onto the detection systems.

The scope of the invention should, therefore, be determined not with reference to the above description, but instead should be determined with reference to the appended claims along with their full scope of equivalents.

What is claimed is:

1. An apparatus for mixing a fluid, the apparatus comprising:
   a first substrate comprising a first inner surface functionalized with a microarray of reactive moieties;
   a substantially parallel second substrate also comprising a second inner surface, wherein said first and second inner surfaces bound a closed chamber there between, said chamber adapted to retain a quantity of fluid so that the fluid is in contact with both surfaces;
   at least one bubble disposed within said chamber; and
   means for moving the chamber so that the bubble moves relative to the fluid so effect mixing of the fluid.

2. The apparatus of claim 1, wherein the closed chamber has a thickness of less than about 2 millimeters.

3. The apparatus of claim 1, wherein the bubble comprises a gas.

4. The apparatus of claim 1, wherein the bubble comprises nitrogen.

5. The apparatus of claim 1, wherein the babble is produced by introducing a volume of the fluid that is Jess than she total volume of the closed chamber.

6. The apparatus of claim 1, further including a flexible seal between the inner surface of the first substrate and the inner surface of the second substrate.

7. The apparatus of claim 1, further comprising means for introducing fluid into the closed chamber.

8. The apparatus of claim 1, wherein the first substrate and the second substrate are individually comprised of a material selected from the group consisting of glass, silicon, fused silica, plastic and a combination thereof.

9. The apparatus of claim 1, wherein the first substrate is comprised of glass.

10. The apparatus of claim 1, wherein the means for moving the bubble is selected from the group consisting of rotating the apparatus about an axis, rolling the apparatus, and reciprocally shaking the apparatus.

11. A method for mixing a fluid, comprising: providing an apparatus according to claim 1, introducing a fluid into the closed chamber; introducing a bubble within the fluid; and moving the bubble in the fluid to effect mixing of the fluid.

12. A method for mixing a fluid, comprising: providing an apparatus according to claim 2, introducing a fluid into the closed chamber, introducing a bubble within the fluid; and moving the bubble in the fluid to effect mixing of the fluid.

13. A method for mixing a fluid, comprising: providing an apparatus according to claim 3, introducing a fluid into the closed chamber; introducing a bubble within the fluid; and moving the bubble in the fluid to effect mixing of the fluid.

14. A method for mixing a fluid, comprising: providing an apparatus according to claim 10, introducing a fluid into the closed chamber; introducing a bubble within the fluid; and moving the bubble in the fluid to effect mixing of the fluid.

15. An apparatus for mixing a fluid, the apparatus comprising:
   a first substrate comprising a first inner surface functionalized with an array of reactive moieties;
   a substantially parallel second substrate also comprising a second inner surface, wherein said first and second inner surfaces bound a closed chamber there between, said chamber adapted to retain a quantity of fluid so that the fluid is in contact with both surfaces;
   at least one bubble disposed within said chamber; and
   means for moving the chamber so that the bubble moves relative to the fluid to effect mixing of the fluid.

16. The apparatus of claim 15, wherein the closed chamber has a thickness of less than about 2 millimeters.

17. The apparatus of claim 15, wherein the bubble comprises a gas.

18. The apparatus of claim 15, wherein the bubble comprises a gas selected from the group consisting of air, nitrogen, argon, or oxygen.

19. The apparatus of claim 15, wherein the bubble is produced by introducing a volume of the fluid that is less than the total volume of the closed chamber.

20. The apparatus of claim 15, further including a flexible seal between the inner surface of the first substrate and the inner surface of the second substrate.

21. The apparatus of claim 15, further comprising means for introducing fluid into the closed chamber.

22. The apparatus of claim 15, wherein the first substrate and The second substrate are individually comprised of a material selected from the group consisting of glass, silicon, fused silica, plastic, ceramic, and metal, and a combination thereof.

23. The apparatus of claim 15, wherein the first substrate and the second substrate are individually comprised of glass.

24. The apparatus of claim 15, wherein the means for moving the babble is selected from the group consisting of rotating the apparatus about an axis, rolling the apparatus, and reciprocally shaking the apparatus.

25. A method for mixing a fluid, comprising: providing an apparams according to claim 15, introducing a fluid into the closed chamber; introducing a bubble within the fluid; and moving the bubble in the fluid to effect mixing of the fluid.

26. A method for mixing a fluid, comprising: providing an apparatus according to claim 16, introducing a fluid into the closed chamber; introducing a bubble within the fluid; and moving the bubble in the fluid to effect mixing of the fluid.

27. A method for mixing a fluid, comprising: providing an apparatus according to claims 17, introducing a fluid into the closed chamber; introducing a bubble within the fluid; and moving the bubble in the fluid to effect mixing of the fluid.

28. A method for mixing a fluid, comprising: providing an apparatus according to claim 24, introducing a fluid into the closed chamber; introducing a bubble within the fluid; and moving the bubble in the fluid to effect mixing of the fluid.

* * * * *